(12) United States Patent
Zhang et al.

(10) Patent No.: US 12,104,169 B2
(45) Date of Patent: Oct. 1, 2024

(54) CHEMICAL REPROGRAMMING TO GENERATE NEURONAL CELLS

(71) Applicant: The J. David Gladstone Institutes, a testamentary trust established under the Will of J. David Gladstone, San Francisco, CA (US)

(72) Inventors: Mingliang Zhang, San Francisco, CA (US); Sheng Ding, Orinda, CA (US)

(73) Assignee: The J. David Gladstone Institutes, a testamentary trust established under the Will of J. David Gladstone, San Francisco, CA (US)

( * ) Notice: Subject to any disclaimer, the term of this patent is extended or adjusted under 35 U.S.C. 154(b) by 0 days.

(21) Appl. No.: 17/587,116

(22) Filed: Jan. 28, 2022

(65) Prior Publication Data

US 2022/0243173 A1     Aug. 4, 2022

Related U.S. Application Data

(63) Continuation of application No. 15/750,570, filed as application No. PCT/US2016/045290 on Aug. 3, 2016, now abandoned.

(60) Provisional application No. 62/202,443, filed on Aug. 7, 2015.

(51) Int. Cl.
*C12N 5/0793* (2010.01)
*A61K 35/30* (2015.01)

(52) U.S. Cl.
CPC ............ *C12N 5/0619* (2013.01); *A61K 35/30* (2013.01); *C12N 2501/065* (2013.01); *C12N 2501/115* (2013.01); *C12N 2501/15* (2013.01); *C12N 2501/155* (2013.01); *C12N 2501/385* (2013.01); *C12N 2501/415* (2013.01); *C12N 2501/999* (2013.01); *C12N 2506/1307* (2013.01)

(58) Field of Classification Search
None
See application file for complete search history.

(56) References Cited

U.S. PATENT DOCUMENTS

| | | |
|---|---|---|
| 2011/0275157 A1 | 11/2011 | You et al. |
| 2013/0059385 A1 | 3/2013 | Li et al. |
| 2014/0220681 A1 | 8/2014 | Valamehr et al. |
| 2015/0010515 A1 | 1/2015 | Schoeler et al. |
| 2015/0175962 A1 | 6/2015 | Zhu et al. |
| 2019/0010451 A1 | 1/2019 | Zhang et al. |

FOREIGN PATENT DOCUMENTS

| | | |
|---|---|---|
| EP | 3331988 B1 | 9/2023 |
| WO | 2011066430 | 6/2011 |
| WO | 2015013653 | 1/2015 |
| WO | 2015041809 | 3/2015 |
| WO | 2017027280 | 2/2017 |

OTHER PUBLICATIONS

"International Application Serial No. PCT US2016 045290, International Search Report mailed Oct. 21, 2016", 3 pgs.
"International Application Serial No. PCT US2016 045290, Written Opinion mailed Oct. 21, 2016", 5 pgs.
"International Application Serial No. PCT US2016 045290, International Preliminary Report on Patentability mailed Feb. 22, 2018", 7 pgs.
"European Application Serial No. 16835648.3, Extended European Search Report mailed Dec. 17, 2018", 9 pgs.
"European Application Serial No. 16835648.3, Response filed Jul. 1, 2019 to Extended European Search Report mailed Dec. 17, 2018", 24 pgs.
"U.S. Appl. No. 15/750,570, Restriction Requirement mailed Nov. 27, 2019", 7 pgs.
"U.S. Appl. No. 15/750,570, Response filed Feb. 27, 2020 to Restriction Requirement mailed Nov. 27, 2019", 7 pgs.
"U.S. Appl. No. 15/750,570, Non Final Office Action mailed Jun. 11, 2020", 10 pgs.
"European Application Serial No. 16835648.3, Communication Pursuant to Article 94(3) EPC mailed Sep. 10, 2020", 4 pgs.
"U.S. Appl. No. 15/750,570, Response filed Dec. 11, 2020 to Non Final Office Action mailed Jun. 11, 2020", 13 pgs.
"European Application Serial No. 16835648.3, Response filed Dec. 23, 2020 to Communication Pursuant to Article 94(3) EPC mailed Sep. 10, 2020", w English Claims, 5 pgs.
"U.S. Appl. No. 15/750,570, Final Office Action mailed Apr. 1, 2021", 14 pgs.
"U.S. Appl. No. 15/750,570, Response filed Jul. 1, 2021 to Final Office Action mailed Apr. 1, 2021", 11 pgs.
"European Application Serial No. 16835648.3, Communication Pursuant to Article 94(3) EPC mailed Sep. 30, 2021", 5 pgs.
"U.S. Appl. No. 15/750,570, Non Final Office Action mailed Oct. 28, 2021", 11 pgs.
"European Application Serial No. 16835648.3, Response filed Jan. 24, 2022 to Communication Pursuant to Article 94(3) EPC mailed Sep. 30, 2021", 204 pgs.
Dhruba, Biswas, "Chemically Induced Reprogramming of Somatic Cells to Pluripotent Stem Cells and Neural Cells", International Journal of Molecular Sciences, vol. 17, No. 2, (Feb. 6, 2016), 13 pgs.
Maetzel, "Genetic and Chemical Correction of Cholesterol Accumulation and Impaired Autophagy in Hepatic and Neuronal Cells Derived from Niemann-Pick Type C Patient-Speciic iPS Cells", Supp. Info., Stem Cell Reports, vol. 2, (2014), 15 pgs.
Pan, "Autophagic control of cell 'sternness'", EMBO Molecular Medicine, vol. 5, (2013), 327-331 pgs.

(Continued)

*Primary Examiner* — Teresa E Knight
(74) *Attorney, Agent, or Firm* — Schwegman Lundberg & Woessner, P.A.

(57) ABSTRACT

Compositions and methods are described herein for chemically inducing cells to change their differentiation state and become neuronal cells.

7 Claims, 27 Drawing Sheets

Specification includes a Sequence Listing.

(56) References Cited

OTHER PUBLICATIONS

Zhang, Mingliang, "Pharmacological Reprogramming of Fibroblasts into Neural Stem Cells by Signaling-Directed Transcriptional Activation", Cell Stem Cell, Elsevier, Cell Press, Amsterdam, NL, vol. 18, No. 5, (Apr. 28, 2016), 16 pgs.

Zheng, Jie, "A combination of small molecules directly reprograms mouse fibroblasts into neural stem cells", Biochemical and Biophysical Research Ommunications, Elsevier, Amsterdam, NL, vol. 476, No. 1, (May 17, 2016), 42-48.

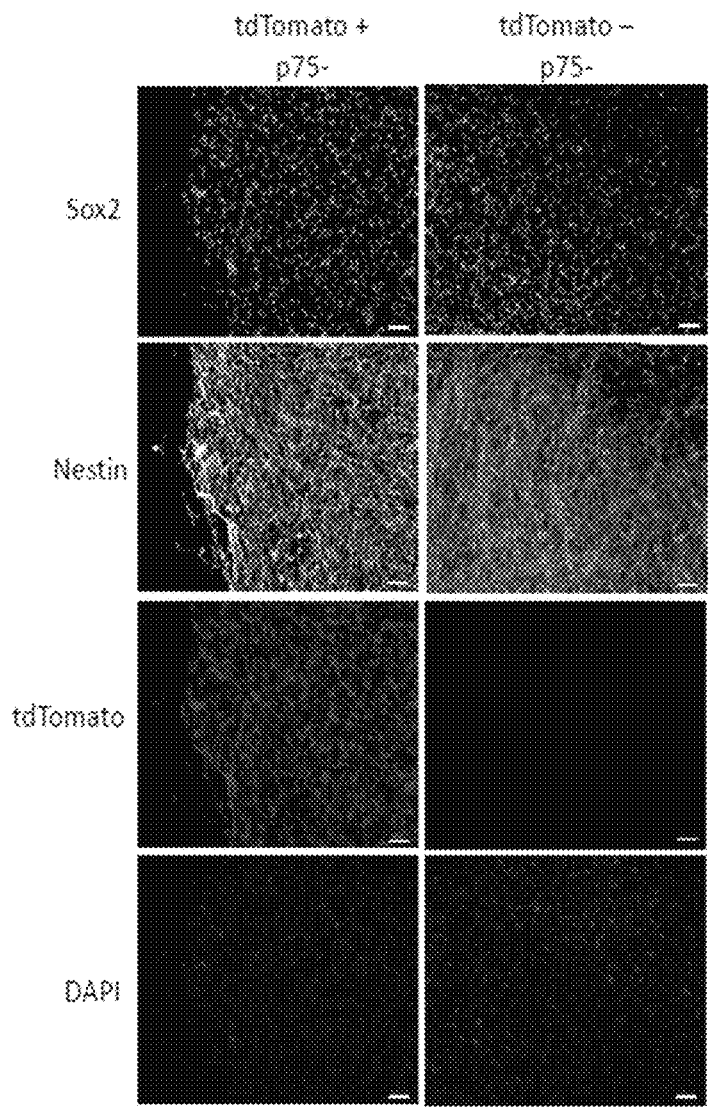
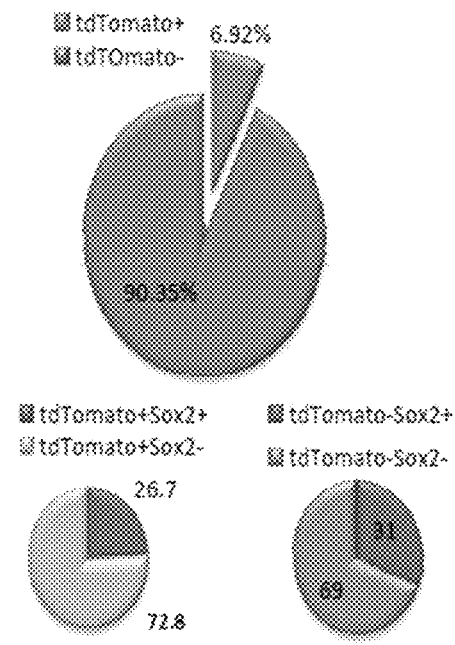
FIG. 6B
FIG. 6A

CHEMICAL REPROGRAMMING TO GENERATE NEURONAL CELLS

CROSS REFERENCE TO RELATED APPLICATIONS

This application claims benefit of the priority filing date of U.S. Provisional patent Application Ser. No. 62/202,443, entitled "Chemical Reprogramming to Generate Neuronal Cells," filed Aug. 7, 2015, the disclosure of which is incorporated herein by reference in its entirety.

GOVERNMENT SUPPORT

This invention was made with government support under R01EY021374 awarded by the National Institutes of Health. The government has certain rights in the invention.

BACKGROUND

Generation of expandable neural stem cells (NSCs) from fibroblasts with full developmental potential represents a promising therapeutic approach for treating neurodegenerative diseases or injuries. However, the differentiated cell state has traditionally been considered stable and resistant to changes in lineage identity. Scientists have reprogrammed differentiated somatic cell types from humans and other organisms to the pluripotent state ("pluripotent reprogramming") by forced expression of a set of transcription factors (Takahashi, K. et al. *Induction of pluripotent stem cells from adult human fibroblasts by defined factors*. Cell 131, 861-872 (2007)), somatic cell nuclear transfer (Campbell et al., *Sheep cloned by nuclear transfer from a cultured cell line*. Nature 380: 64-66 (1996); Gurdon et al., *Sexually mature individuals of Xenopus laevis from the transplantation of single somatic nuclei*, Nature 182, 64-65 (1958)) or cell fusion (Cowan et al., Nuclear reprogramming of somatic cells after fusion with human embryonic stem cells, Science (New York, N.7309, 1369-1373 (2005); Tada et al., *Nuclear reprogramming of somatic cells by in vitro hybridization with ES cells*. Curr Biol 11: 1553-1558 (2001)). In addition, some studies indicate that ectopic expression of selected genes or cell fusion may be employed to convert an adult cell type to another adult cell type (Cobaleda et al., *Conversion of mature B cells into T cells by dedifferentiation to uncommitted progenitors*, Nature 449, 473-477 (2007); Davis et al., *Expression of a single transfected cDNA converts fibroblasts to myoblasts*, Cell 51, 987-1000 (1987); Feng, et al. *PU. l and C/EBPalpha/beta convert fibroblasts into macrophage-like cells*, Proc. Nat. Acad. Sci. USA 105, 6057-6062 (2008); Ieda et al. *Direct reprogramming of fibroblasts into functional cardiomyocytes by defined factors*, Cell 142, 375-386 (2010), Zhou et al., *In vivo reprogramming of adult pancreatic exocrine cells to beta-cells*, Nature 455, 627-632 (2008); and Zhou, Q. & Melton, D. A. *Extreme makeover: converting one cell into another*, Cell Stem Cell 3: 382-388 (2008)). This process is termed trans-differentiation or lineage reprogramming.

However, major challenges remain due to the low efficiency and slow reprogramming process. A more significant challenge is how to accomplish cell reprogramming without the need for genetic changes in the reprogrammed cells, because such genetic changes give rise to concerns about introduced mutations at the insertion site of expression cassettes encoding pluripotency factors.

In addition, most previous studies of reprogramming to generate neural stem cells have started with mouse embryonic fibroblasts (MEFs). However, the MEFs are an inherently heterogeneous population containing non-fibroblast precursor cell types that may be specified into neural lineage via processes other than bona fide reprogramming. To unambiguously define the origin of the cells that are reprogrammed into neural stem cells, genetic lineage tracing of the starting fibroblasts would be required, especially for conditions using combinations of small molecules given the indirect induction mechanisms of reprogramming and differentiation.

SUMMARY

The compositions and methods described herein can accomplish reprogramming of differentiated, non-neuronal cells to generate neural progenitor and mature neuronal cells by chemical means and without the need for genetic engineering. Concerns about introduced genetic mutations are obviated when the compositions and methods described herein are employed. Moreover, use of the compositions and methods described herein is less labor intensive, and less time consuming, than previously available methods.

One aspect of the invention is a composition that includes at least four of the following active agents: a BMP type I receptor ALK2/3 inhibitor, a TGF-beta inhibitor, a WNT inhibitor, a neuronal differentiation enhancer, a SMO agonist, a retinoic acid receptor γ agonist, a DNA methyltransferase inhibitor, a histone demethylase inhibitor, an autophagy regulator, or any combination thereof. For example, the composition can contain active agents CHIR99021; LDN193189; A83-01; Hh-Ag1.5; retinoic acid; SMER28; RG108, parnate, and bFGF, as well as other ingredients. The other ingredients can be a pharmaceutically acceptable carrier (if the composition is administered to a subject), or cell culture media ingredients, if the composition is part of a cell culture medium.

Another aspect is a method of generating a reprogrammed neuronal progenitor cell or a reprogrammed neuronal cell that involves contacting a selected cell with the composition, to thereby generate a reprogrammed neuronal progenitor cell or a reprogrammed neuronal cell.

Another aspect is a method that involves administering the composition to a subject. For example, the subject can suffer, or may be suspected of suffering, from Amyotrophic lateral sclerosis (ALS), Alzheimer's disease, Parkinson's disease, multiple sclerosis, Primary lateral sclerosis (PLS), Progressive bulbar palsy, Pseudobulbar palsy, Progressive muscular atrophy, Spinal muscular atrophy (SMA), including Type I (also called Werdnig-Hoffmann disease), Type II, Type III (Kugelberg-Welander disease), Fazio-Londe disease, Huntington's disease, Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, stroke, head trauma, spinal cord injury, or a combination thereof.

Another aspect is a kit that includes the composition, and instructions for using the composition. Such a kit can also include components for in vitro cell culture of a selected cell. In some cases the kit can contain a diluent, a pharmaceutically acceptable carrier, a syringe, a catheter, or a device for delivery of cells or of the composition to a subject. The kit can also contain antibodies, probes, or primers for detection of one or more neuronal progenitor cell marker or one or more neuronal cell marker.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A shows a schematic diagram (top) illustrating a cell lineage tracing strategy that generates fibroblast cells that express the tdtomato marker and that are converted to ciNSLCs by the chemical reprogramming protocol described herein (summarized below the schematic diagram of chemically induced cell lineage progression). As shown, the chemical reprogramming protocol involves culturing cells in medium containing fetal bovine serum (FBS) for about 24 hours, followed by incubation of the cells in medium containing CHIR99021, LDN193189, A83-01, Hh-Ag1.5, retinoic acid, SMER28, RG108, parnate, and bFGF for about ten days. FIG. 1B shows four images of the same ciNSLC colony that was derived from tdtomato-expressing mouse embryonic fibroblasts (tdMEFs). The top left panel shows tdtomato expression in the colony; the top right image shows Sox2 expression in the colony; the bottom left panel shows Nestin expression in the colony; and the bottom right panel shows DAPI staining of the colony nuclei. Scale bar is 100 µm. FIG. 1C graphically illustrates expression levels of the neural stem cells genes identified along the x-axis for three independent ciNSLC lines, and two primary neural progenitor cell (NPC) lines. The first bar on the left shows expression of ciNSLC line #1; the second bar from the left shows expression of ciNSLC line #2; the third bar from the left shows expression of ciNSLC line #3; the fourth bar from the left shows expression by a tdtomato-expressing neural progenitor cell (tdNPC); and the rightmost bar shows expression by a Tau-GFP and tdtomato-expressing neural progenitor cell (Tau-GFP tdNPC). ciNSLC lines #1 and #2 were derived from tdMEFs, and ciNSLC line #3 was from tdtomato-expressing mouse tail-tip fibroblasts (tdTTFs), Gene expression was detected by qRT-PCR and is shown relative to control neural stem cell line, SCR029, FIG. 1D shows images of expanded ciNSLC colonies derived from tdtomato-expressing mouse embryonic fibroblasts (td-MEFs). The left column of images show the expression of the genes listed to the left ("target"); the middle column of images show expression of tdtomato; and the third column of images show the merged expression of the target genes and tdTomato. Expression is shown of target genes Sox2 (top row of panels), Nestin (second row of panels), Olig2 (third row of panels), N-Cad (fourth row of panels), and BrdU (bottom row of panels). Scale bar is 50 µm. FIG. 1E shows paired scatter plots comparing the global gene expression pattern of ciNSLC with tdMEF (left) and SCR029 (right). FIG. 1F graphically illustrates the reprogramming efficiency as calculated by Sox2 and Nestin expression of batches tdMEF #1 and tdMEF #2, Tau-GFP MEF, NGFP MEF, and tdTTF. Total cell number was determined by DAPI staining. Error bars, s.d., based on triplicates for FIG. 1C and FIG. 1F. FIGS. 1G-1I illustrate isolation and characterization of tdMEF cells. FIG. 1G illustrates isolation of the tdTomato+/p75− cell population by FACS. FIG. 1H shows that the tdTomato+/p75−MEF cell population used as a starting cell population does not express neural genes Sox2, Hes5, Ascl1, Gfap, Oli2, or Gaphh as detected by RT-PCR analysis. The neural stem cell (NSC) line SCR029 was used as a positive control. FIG. 1I also shows that the tdTomato+/p75− MEF cell population does not express Sox2, Pax6, Olig2, Nestin, GFAP and NG2 as detected by immunostaining. The left column of images show the expression of tdTomato; the middle column of images shows expression of the genes listed to the left ("target"); and the third column of images shows DAPI staining of nuclei. Expression is shown of target genes Sox2 (top row of panels), Pax6 (second row of panels), Olig2 (third row of panels), Nestin (fourth row of panels), GFAP (fifth row of panels), and NG2 (bottom row of panels).

FIG. 2A shows images of tdTomato-expressing ciNSLCs that were immunostained for Tuj1, Map2, O4, or GFAP, illustrating that ciNSLCs can differentiate into Tuj1-positive and Map2-positive neurons (top, scale bar is 100 µm), O4-positive oligodendrocytes (middle, scale bar is 50 µm), and GFAP-positive astrocytes (bottom, scale bar is 100 µm). FIG. 2B graphically illustrates the percentage of vGlut1-positive glutamatergic neurons and GABA-positive GABAergic neurons, normalized to the total number of Tuj1-positive neurons, in ciNSLCs that were further differentiated in vitro under the typical neuronal differentiation conditions (Kim et al. *Proc Natl Acad Sci USA* 108: 7838-7843 (2011). FIG. 2C graphically illustrates the percentage of Tuj-positive neurons and GFAP-positive astrocytes in the total population of spontaneously differentiated ciNSLCs. FIG. 2D shows representative traces of membrane potentials of ciNSLC-derived neurons in responses to step-current injections. FIG. 2E shows spontaneous synaptic network activities of ciNSLC-derived neurons. FIG. 2F shows ciNSLCs differentiated into NeuN-positive neurons (left panel), Olig2-positive oligodendrocytes (middle panel), and GFAP-positive astrocytes (right panel) four weeks after injection of ciNSLCs into newborn mouse brain cortex. Expression of these genes was detected by immunostaining and DAPI was used to stain the brain section of injected site. Scale bar is 50 µm. FIGS. 2G-2L illustrate further characteristics of the M9 cocktail and of ciNSLCs generated by use of this M9 cocktail. FIG. 2G graphically illustrates the relative reprogramming efficiency of the M9 cocktail without one of its components compared to the M9 cocktail with all components. The reprogramming efficiency of each of the indicated treatments was calculated and normalized with that of M9. The use of a negative sign "−" means that the indicated molecule was not present in the M9 cocktail employed. DMSO was negative control. The symbol * means that P<0.01. FIG. 2H shows images of tdMEF-derived small clusters (upper three panels) and tdMEF-derived colonies (bottom three panels) at day 6 of M9 treatment. FIG. 2I shows images of tdMEF colonies at day 6 of treatment with the M9 cocktail. FIG. 2J show images of tdMEF-derived colonies exhibiting alkaline phosphatase (ALP) activity (darker staining). FIG. 2K shows electrophoretically separated products of RT-PCR analysis of the neural gene expression in two independent lines of ciNSLC (#1 and #2), in comparison to parental tdMEF cells and positive control SCR029 cells, illustrating expressing Pax6, Sox2, Asch1, and Olig2. FIG. 2L graphically illustrates the relative reprogramming efficiency for tdMEFs treated with M9, VCR, or DMSO control. VCR is a cocktail of valproic acid, CHIR99021, and RepSox.

FIG. 3A graphically illustrates expression of Sox1, Sox2, Pax6, Olig2, Hes5, and Ascl1 during neural reprogramming of cells on day 0 (D0, first bar to the left with barely discernible expression, day 4 (D4, second bar from the left), day 8 (D8, third bar from the left), and day 12 (D12, fourth bar from the left; highest bar for Pax6). The ciNSLC (fifth bar from the left) exhibit the highest expression of the different cell types for Sox1, Sox2 and Hes1. The NSC line SCR029 (rightmost bar) was used as a positive control. Expression levels were detected by qRT-PCR, and the fold enrichment was assessed relative to tdMEF cells. Error bars, s.d., based on triplicates. FIG. 3B shows a heatmap of differentially expressed genes at indicated time points (day 0, day 4, day 8, and day 12) of neural reprogramming (left panel) with lists of GO terms (middle panel) and representative genes (right panel) for each block (1 to 5, as labeled). Red and blue colors in the original indicate upregulate and downregulated genes, respectively. In black and white images the maximal expression is shown by the darker shades. For example, ciNSLC and SCR029 exhibit maximal expression at the top right, but the Day 0 (D0) cells exhibit the maximal expression at the bottom left. FIG. 3C illustrates principle component analysis at the indicated time points (day 0, day 4, day 8, and day 12) of neural reprogramming. FIG. 3D schematically illustrates unsupervised hierarchical clustering of cells undergoing neural reprogramming at the indicated times (day 0, day 4, day 8, and day 12). FIG. 3E is a heatmap illustrating the expression of neural stem cell-enriched genes (Aschl1, Olig2, Olig1, Sox2, Nrcam, Shh, Grh13, Zic2, and Pax2) and fibroblast-enriched genes (Thy1, S100α4, and Periostin), with lists of representative genes for each group (right panel). Red and blue colors indicate upregulation and downregulated genes, respectively. In black and white images the maximal expression is shown by the darker shades. For example, ciNSLC and SCR029 exhibit maximal expression of neural genes (top right), but the Day 0 (D0, fibroblasts) cells exhibit the maximal expression of Thy1, S100α4, and Periostin (bottom left). FIG. 3F illustrates the average transcription activity of genes under GO terms for the ectoderm, mesoderm, endoderm development, stem cell maintenance, and fibroblasts, at day 0 (D0) and day 4 (D4) of reprogramming. FIG. 3G shows images of ciNSLC cells in a monolayer culture (left) of ciNSLC and as ciNSLC neurospheres formed in suspension culture (right) at passage 5. Scale bar is 50 µm. FIG. 3H shows images of ciNSLC cells in a monolayer culture (left) of ciNSLC and as ciNSLC neurospheres formed in suspension culture (right) at passage 10. Scale bar is 100 µm.

FIG. 4A graphically illustrates the reprogramming efficiency of cells analyzed at day 10 with the M9 composition and when one small molecule inhibitor of the corresponding signaling pathway was added (+) or removed (−). The efficiency of M9-induced reprogramming was assigned as "1". DMSO was used as negative control. FIG. 4B also graphically illustrates the reprogramming efficiency of cells analyzed at day 10 when a small molecule inhibitor of the corresponding signaling pathway was added (+) or removed (−). The efficiency of M9-induced reprogramming was assigned as "1". DMSO was used as negative control. FIG. 4C shows a schematic diagram (top panel) of the Sox2 regulatory regions SRR1, SRR2 and promoter (Pro). The bottom left panel of FIG. 4C graphically illustrates the relative binding of Elk1 at the Sox2 SRR1, SRR2 and promoter regulatory regions at the indicated time points. The bottom right panel of FIG. 4C shows the relative binding of Gli2 at the Sox2 SRR1, SRR2 and promoter regulatory regions at the indicated time points. Relative binding was relative to binding by an IgG control. TSS refers to transcription starting site, and Pro refers to promoter. FIG. 4D graphically illustrates the relative reprogramming efficiency assessed when Elk1 expression was knocked down by Elk1 shRNA at the indicated time points (day 1, day 4, or day 8). FIG. 4E graphically illustrates the relative reprogramming efficiency assessed when Gli2 expression was knocked down by Gli2 shRNA at the indicated time points (day 1, day 4, or day 8). FIG. 4F graphically illustrates the relative reprogramming efficiency assessed when EMI is over-expressed or when Gli2 is over-expressed. The acronyms have the following meaning: wt, wild type; KD, shRNA-mediated gene knockdown; o e, overexpression. FIG. 4G is a schematic diagram of a model interpreting M9-induced neural reprogramming through activating intrinsic neural program. Error bars, s.d., based on triplicates for FIG. 4A-F. *, P<0.01. FIG. 4H shows images ciNSLC-derived neurons illustrating the morphology of the neurons at day 3 (left), day 6 (middle), and day 10 (right) of differentiation. Scale bar is 10 µm. FIG. 4I shows images of images ciNSLC-derived neurons illustrating differentiation into Map-positive and NeuN-positive neurons Scale bar is 100 µm. FIG. 4J shows images of images ciNSLC-derived neurons illustrating differentiation into vGLUT1-positive and Map2-positive neurons. Scale bar is 50 µm. FIG. 4K shows images of images ciNSLC-derived neurons illustrating differentiation into GABA-positive and Map2-positive neurons. Scale bar is 50 µm, FIG. 4L shows images of images ciNSLC-derived neurons illustrating differentiation into Synapsin-positive neurons. Scale bar is 50 µm.

FIG. 5A shows current traces of ciNSLC-derived neurons in response to 80 pA current injection. FIG. 5B shows representative traces of whole-cell current in the voltage-clamp mode. An inward current was observed that could be blocked by tetrodotoxin (TTX) FIG. 5C shows representative traces of whole-cell current in the voltage-clamp mode. An outward current was observed that could be blocked by tetraethylammonium (TEA). FIG. 5D shows excitatory postsynaptic currents observed in cells damped at −70 mV in response to L-glutamate puffs. FIG. 5E show inhibitory postsynaptic currents in cells clamped at 0 mV in response to GABA puffs.

FIG. 6A-6B further illustrate conversion of different populations into ciNSLC by the M9 cocktail composition. FIG. 6A shows that tdTomato-positive and tdTomato-negative populations can be converted into Sox2⁻/Nestin⁻ ciNSLC by the M9 cocktail, as detected by immunostaining. FIG. 6B shows pie-charts illustrating the efficiency of conversion of tdTomato-positive and tdTomato-negative populations. The larger top pie-chart shows the tdTomato positive and negative cells in original MEF population, where tdTomato-positive cells constitute 6.92% of the population and tdTomato-negative cells are 90.35% of the population. The two pie charts at the bottom show the reprogramming efficiency for both populations, where 26.7% of tdTomato-positive cells became Sox2⁻ cells, and where 31% of the tdTomato-negative cells became Sox2⁻ cells. The expression of Sox2 was used as marker for reprogramming.

FIG. 7A shows the expression of Sox2 as detected by immunostaining and the percentage of cells expressing Sox2 at the indicated times (day 4, day 8, day 12, and passage 1 (P1)), Total cell number was determined by DAPI staining. Scale bar is 20 µm for day 4 and P1, 50 µm for day 8, and 100 µm for day 12. Inset images at the left of most panel are expanded images of the field within the rectangle. FIG. 7B graphically illustrates expression levels of 16 neural genes as determined by RNA-sect analysis at the indicated time points (day 0, day 4, day 8, day 12). The NSC line SCR029 was used as a positive control. FIG. 7C graphically illustrates percent Sox2 promoter chromatin immunoprecipitated by antibodies against H3K27me3, H3K4me3, and H3K27 Ac as detected by ChiP-qPCR analysis. The relative abundance of chromatin immunoprecipitation was normalized to Input. Error bars, s.d., based on triplicates.

FIG. 8A graphically illustrates the types of gene transcripts enriched in ciNSLC versus the NSC line SCR029, which was used as a positive control. FIG. 8B graphically illustrates the types of gene upregulated during reprogramming (day 4 versus day 0).

DETAILED DESCRIPTION

Figure 1A:
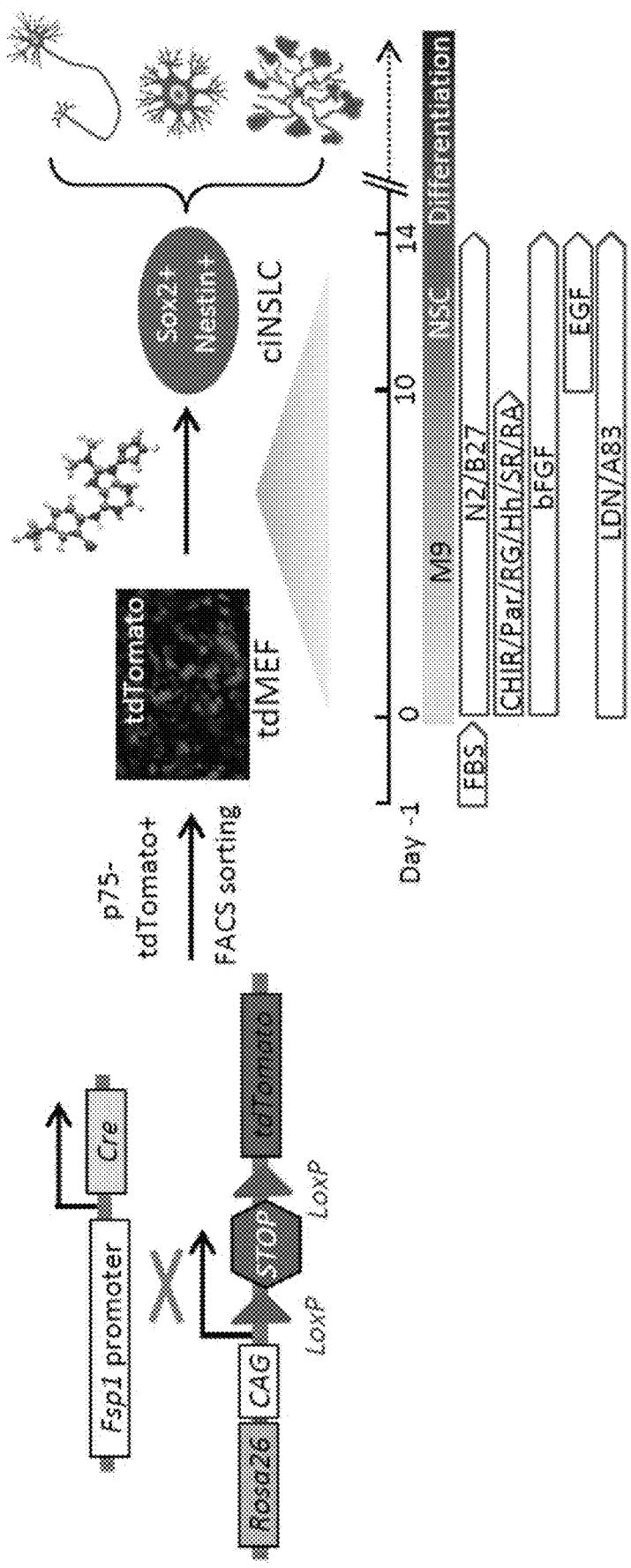
FIG. 1A-1I illustrate conversion of adult cells into chemically induced neural stem cell-like cells (ciNSLCs) using a chemical approach.

As described herein, differentiated non-neuronal, mammalian cells can be reprogrammed to cross lineage boundaries and to directly convert into neuronal progenitor cells or mature functional neuronal cells, without genetic manipulation. Instead, a differentiated non-neuronal cell can simply be treated with a composition of chemical compounds to change that cell into a neuronal cell.

A composition of nine components is described herein that can be used to convert a differentiated non-neuronal cell convert into neuronal progenitor cells or mature functional neuronal cells, without genetic manipulation. The composition includes at least one BMP type I receptor ALK2/3 inhibitor, at least one TGF-beta inhibitor, at least one WNT inhibitor, at least one neuronal differentiation enhancer, at least one SMO agonist, at least one retinoic acid receptor γ agonist, at least one DNA methyltransferase inhibitor, at least one histone demethylase inhibitor, and at least one autophagy regulator.

Although one or more recombinantly introduced transcription factors can be used if desired, differentiated mammalian cells can be converted into the neuronal cell lineage without such genetic manipulation. Instead, the composition of chemical compounds can be administered to a subject, or differentiated (e.g., non-neuronal) cells from the subject can be incubated with such a composition to convert the subject's cells to a neuronal cell type.

Compared to the genetic approach, small molecule-based chemical strategies may have several important advantages. Small molecules are relatively easy to apply, optimize and manufacture, and they can be more readily developed into conventional pharmaceuticals. Unlike the reprogramming mediated by pioneer transcription factors, the chemical-induced cellular reprogramming represents a different process. Mechanistically, small molecules interact with and modulate endogenously expressed proteins of the starting (i.e., selected) cell type, and indirectly and ultimately gain and establish target cell type specificity. Therefore, achieving chemical reprogramming would provide a novel approach and process to investigate the underlying mechanism of cell fate conversion.

However, introduction of expression cassettes encoding the Elk-1 transcription activator and/or the Gli2 zinc-finger transcription factor can increase the proportion of cells that are reprogrammed to cross lineage boundaries and converted into neuronal progenitor cells or mature functional neuronal cells.

The components used in the compositions and methods are described in more details below.

BMP Type I Receptor ALK2/3 Inhibitors

As illustrated herein use of one or more BMP type I receptor ALK2/3 inhibitors can facilitate conversion of differentiated cells into the neuronal cell lineage.

ALK2 (activin A receptor type I) can transduce signals for a variety of members of the transforming growth factor beta superfamily of ligands. ALK3 (bone morphogenetic protein receptor, type IA) is a regulator of cell fate decisions during embryogenesis and tissue homeostasis.

BMP type I receptor ALK2/3 inhibitors are available. For example, the methods and compositions described herein can include any of the following:
- 4-(6-(4-(piperazin-1-yl)phenyl)pyrazolo[1,5-a]pyrimidin-3-yl)quinoline (LDN-193189) available from Miltenyi Biotec,
- 6-[4-[2-(1-Piperidinyl)ethoxy]phenyl]-3-(4-pyridinyl)-pyrazolo[1,5-a]pyrimidine dihydrochloride (Dorsomorphin dihydrochloride; also called compound C, or BML-275), available from Tocris Bioscience;
- 3-(6-amino-5-(3,4,5-trimethoxyphenyl)pyridin-3-yl)phenol (K02288), available from Tocris Bioscience.

In some embodiments, the BMP type I receptor ALK2/3 inhibitor(s) can be 4-(6-(4-(piperazin-1-yl)phenyl)pyrazolo[1,5-a]pyrimidin-3-yl)quinoline (LDN-193189)

The BMP type I receptor ALK2/3 inhibitor(s) can be used in various concentrations. For example, the BMP type I receptor ALK2/3 inhibitor(s) can be employed at a concentration of about 0.1 nanomolar to about 1 micromolar, or about 1 nanomolar to about 700 nanomolar, or about 10 nanomolar to about 500 nanomolar, or about 50 nanomolar to about 200 nanomolar, or about 100 nanomolar in a solution. In a dry formulation, BMP type I receptor ALK2/3 inhibitors can be present in amounts of about 0.01 mg to about 2000 mg, or about 0.1 mg to about 1000 mg, or about 1 mg to about 500 mg.

Cells can be incubated in a medium containing one or more BMP type I receptor ALK2/3 inhibitor (e.g., LDN-193189) for varying amounts of time. For example, the cells can be incubated in a medium containing a BMP type I receptor ALK2/3 inhibitor until at least some of the cells express neural progenitor markers such as Sox2⁻ and/or Nkx6.1⁻. The incubation time can vary, for example, from about 1 day to about 30 days, or from about 2 days to about 25 days, or from about 4 day to about 20 days, or about 10 days.

TGF-Beta Inhibitors

As illustrated herein use of one or more transforming growth factor-beta (TGF-β) inhibitors can facilitate conversion of differentiated cells into the neuronal cell lineage.

There are about thirty members of the transforming growth factor-beta (TGF-β) superfamily, including activin, Nodal, and BMPs. These TGF-β family members elicit their responses through a variety of cell surface receptors that activate Smad protein signaling cascades.

A TGF-beta inhibitor can directly or indirectly, negatively regulate TGF-beta signaling. In some embodiments, one or more TGF-beta inhibitors binds to and reduces the activity of one or more serine/threonine protein kinases selected from the group consisting of ALK5, ALK4, TGF-beta receptor kinase 1 and ALK7, ALK4, ALK5 and ALK7 are all closely related receptors of the TGF-beta superfamily. Desirable TGF-beta inhibitors can bind to and reduce the activity of ALK4, ALK5 (TGF-beta receptor kinase 1) and/or ALK7. In another embodiment, the TGF-beta receptor binds to and reduces the activity of a Smad protein, for example R-SMAD or SMAD1-5 (i.e. SMAD 1, SMAD 2, SMAD 3, SMAD 4 or SMAD 5).

Examples of TGF-β inhibitors include, but are not limited to:

- 3-(6-Methyl-2-pyridinyl)-N-phenyl-4-(4-quinolinyl)-1H-pyrazole-1-carbothioamide (also known as A83-01 available from Tocris Bioscience; a selective inhibitor of TGF-β type I receptor ALK5 kinase, type I activin/nodal receptor ALK4 and type I nodal receptor ALK7 (IC50 values can, e.g., be 12, 45 and 7.5 nM respectively);
- 4-[4-(1,3-benzodioxol-5-yl)-5-(2-pyridinyl)-1H-imidazol-2-yl]benzamide (also known as SB 431542 from Tocris Bioscience; a potent and selective inhibitor of TGF-β type I receptor activin receptor-like kinase ALK5 (e.g., with $IC_{50}$=94 nM), and its relatives ALK4 and ALK7);
- 2-(3-(6-Methylpyridine-2-yl)-1H-pyrazol-4-yl)-1,5-naphthyridine (also known as SJN 2511 from Tocris Bioscience; selective inhibitor of the TGF-β type I receptor ALK5 (IC50 values can, e.g., be 0.004 and 0.023 µM for ALK5 autophosphorylation and ALK5 binding, respectively);
- 4-[4-(2,3-Dihydro-1,4-benzodioxin-6-yl)-5-(2-pyridinyl)-1H-imidazol-2-yl]benzamide (also known as D 4476 from Tocris Bioscience; a selective inhibitor of casein kinase 1 (CK1) and TGF-β type-1 receptor (ALK5) that displays greater than 20-fold selectivity over SAPK2/p38);
- 4-[3-(2-Pyridinyl)-1H-pyrazol-4-yl]-quinoline (also known as LY 364947 from Tocris Bioscience; a selective inhibitor of TGF-β type-1 receptor (TGF-β R1, TGFR-I, TβR-1, ALK-5) (IC50 values can, e.g., be 59, 400 and 1400 nM for TGR-β RI, TGF-β RII and MLK-7K respectively);
- 2-(4-(benzo[d][1,3]dioxol-5-yl)-2-tert-butyl-1H-imidazol-5-yl)-6-methylpyridine (also known as SB505124, and available from Selleckchem.com; a selective inhibitor of ALK4 and ALK5 (e.g., with IC50 of 129 nM and 47 nM, respectively);
- 6-[2-(1,1-Dimethylethyl)-5-(6-methyl-2-pyridinyl)-1H-imidazol-4-yl]quinoxaline (also known as SB 525334 from Sigma-Aldrich; a selective inhibitor of transforming growth factor-β receptor I (ALK5, TGF-(βRI), with IC50=14.3 nM, for example);
- 2-(5-Chloro-2-fluorophenyl)-4-[(4-pyridyl)amino]pteridine (also known as SD 208 from Tocris Bioscience; a potent, orally active ATP-competitive transforming growth factor-n receptor 1 (TGF-βRI) inhibitor, e.g., with IC50=49 nanomolar); and
- any combination thereof.

Various methods for determining if a substance is a TGF-beta inhibitor are known. For example, a cellular assay may be used in which cells are stably transfected with a reporter construct that includes the human PAI-1 promoter or Smad binding sites, driving a luciferase reporter gene. Inhibition of luciferase activity relative to control groups can be used as a measure of compound activity (De Gouville et al., *Br J Pharmacol*, 2005 May; 145(2): 166-177). Another example is the ALPHASCREEN® phosphosensor assay for measurement of kinase activity (Drew A E et al., Comparison of 2 Cell-Based Phosphoprotein Assays to Support Screening and Development of an ALK Inhibitor *J Biomol Screen* 16(2) 164-173, 2011).

The inhibitor that directly or indirectly negatively regulates TGF-beta signaling can, for example, be selected from the group consisting of A83-01, SB-431542, SJN-2511, LY-36494, SB-505124, SB-525334, and SD-208. In some embodiments, the inhibitor that directly or indirectly negatively regulates TGF-beta signaling can inhibit ALK4, ALK5 and/or ALK7. For example, the inhibitor that directly or indirectly negatively regulates TGF-beta signaling can be A83-01.

The TGF-beta inhibitor can be employed in the compositions and methods described herein in a variety of amounts and/or concentrations. For example, the TGF-beta inhibitor can be employed at a concentration of about 0.001 micromolar to about 20 micromolar, or about 0.01 micromolar to about 10 micromolar, or about 0.05 micromolar to about 5 micromolar, or about 0.1 micromolar to about 1 micromolar, or about 0.5 micromolar in a solution. In a dry formulation, the TGF-beta inhibitor can be present in amounts of about 0.01 mg to about 1000 mg, or about 0.05 mg to about 500 mg, or about 0.1 mg to about 50 mg.

The time of contacting or mixing TGF-beta inhibitor (s) with a population of cells (to generate neural cells) can vary, for example, from about 1 day to about 30 days, or from 2 days to about 25 days, or from 3 days to about 20 days, or from 5 days to about 15 days, or from 7 days to about 14 days, or about 10 days.

WNT Activators

As illustrated herein use of one or more WNT activator can facilitate conversion of differentiated cells into the neuronal cell lineage.

The WNT signaling pathway includes a series of events that occur when a WNT protein binds to a cell-surface receptor of a Frizzled receptor family member. Such events result in the activation of Dishevelled family proteins which inhibit a complex of proteins that includes axin, GSK-3, and the protein APC to degrade intracellular beta-catenin. The resulting enriched nuclear beta-catenin enhances transcription by TCF/LEF family transcription factors. A WNT activator can therefore include an agent that activates TCF/LEF-mediated transcription in a cell. WNT activators can be selected from true WNT agonists that bind and activate a Frizzled receptor family member including any and all of the WNT family proteins, an inhibitor of intracellular beta-catenin degradation, activators of TCF/LEF, and inhibitors of GSK-3.

Examples of WNT activators that can be employed include one or more of the following compounds:

- CHIR99021 (6-(2-(4-(2,4-dichlorophenyl)-5-(4-methyl-1H-imidazol-2-yl)pyrimidin-2-ylamino)ethylamino) nicotinonitrile);
- 1-azakenpaullone (9-Bromo-7,12-dihydro-pyrido[3',2':2,3]azepino[4,5-b]indol-6(5H)-one), BIO ((2'2,3'E)-6-Bromoindirubin-3'-oxime);
- AR-A014418 (N-(4-Methoxybenzyl)-N'-(5-nitro-1,3-thiazol-2-yl)urea);
- Indirubin-3'-monoxime;
- 5-Iodo-indirubin-3'-monoxime;
- kenpaullone (9-Bromo-7,12-dihydroindolo-[3,2-d][1]benzazepin-6(5H)-one);
- SB-415286 (3-[[(3-Chloro-4-hydroxyphenyl)amino]-4-(2-nitro-phenyl)-1H-pyrrole-2,5-dione);
- SB-216763 (3-(2,4-Dichlorophenyl)-4-(1-methyl-1H-indol-3-yl)-1H-pyrrole-2,5-dione);
- Maybridge SEW00923SC (2-anilino-5-phenyl-1,3,4-oxadiazole);
- (Z)-5-(2,3-Memylenedioxyphenyl)imidazolidine-2,4-dione,
- TWS119 (3-(6-(3-aminophenyl)-7H-pyrrolo[2,3-d]pyrimidin-4-yloxy)phenol);
- CHIR98014 (N2-(2-(4-(2,4-dichlorophenyl)-5-(1H-imidazol-1-yl)pyrimidin-2-ylamino)ethyl)-5-nitropyridine-2,6-diamine);

SB415286 (3-(3-chloro-4-hydroxyphenyl amino)-4-(2-nitrophenyl)-1H-pyrrole-2,5-dione);

Tideglusib (also known as NP031112, or NP-12; 1,2,4-Thiadiazolidine-3,5-dione, 2-(1-naphthalenyl)-4-(phenylmethyl)), LY2090314 (1H-Pyrrole-2,5-dione, 3-imidazo[1,2-a]pyridin-3-yl-4-[1,2,3,4-tetrahydro-2-(1-piperidinylcarbonyl)pyrrolo[3,2,1-jk][1,4]benzodiazepin-7-yl]);

lithium salt (e.g., LiCl); or any combination thereof.

WNT activators can also include small-interfering RNAs (siRNA, Cell Signaling) that act as GSK-inhibitors, lithium (Sigma), kenpaullone (Biomol International, Leost, Metal (2000) *Eur J Biochem* 267, 5983-5994), 6-Bromoindirubin-30-acetoxime (Meyer, L et al (2003) *Chem Biol* 10, 1255-1266), SB 216763 and SB 415286 (Sigma-Aldrich), and FRAT-family members and FRAT-derived peptides that prevent interaction of GSK-3 with axin. An overview is provided by Meijer et al, (2004) *Trends in Pharmacological Sciences* 25, 471-480, which is hereby incorporated by reference in its entirety. WNT activators (GSK3 inhibitors) that can be used in the compositions and methods described herein can also include those disclosed in US 20120329152 by Pera et al., which is specifically incorporated herein in its entirety.

The WNT activators can, for example, be CHIR99021, SB216763, TWS119, CHIR98014, Tideglusib, SB415286, LY2090314, or any combination thereof. In some embodiments, the WNT activators can be CHIR99021, whose structure is shown below.

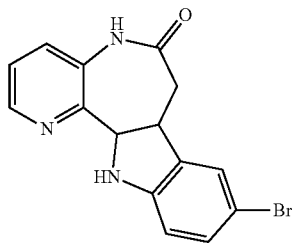 [SMILES: O=C1CC2c3cc(Br)ccc3NC2c2ncccc2N1]

The WNT activators can also be in the form of a salt or hydrate of any of the foregoing compounds.

To increase the proportion of cells that express markers indicative of a neural phenotype, a selected population of cells is contacted or mixed with one or more WNT activators for a time and at a concentration sufficient to differentiate or re-direct the cells to neural lineage.

The WNT activators can be employed in the compositions and methods described herein in a variety of amounts and/or concentrations. For example, the WNT activators can be employed at a concentration of about 0.01 micromolar to about 1 millimolar in a solution, or about 0.1 micromolar to about 100 micromolar in a solution, or about 0.5 micromolar to about 10 micromolar in a solution, or about 1 micromolar to about 5 micromolar in a solution. In a dry formulation, the WNT activators can be present in amounts of about 0.01 mg to about 1000 mg, or about 1 mg to about 100 mg, or about 1 mg to about 10 mg can be present in amounts of about 0.01 mg to about 1000 mg, or about 0.1 mg to about 100 mg, or about 1 mg to about 10 mg.

WNT activators can be added to a selected starting cell population during induced pluripotency and while directing the cells into the neural lineage. WNT activators can also be added to a neural cell population to be converted to neural cells.

The time of contacting or mixing WNT activator(s) with a population of cells (to generate neural cells) can vary, for example, from about 1 day to about 30 days, or from 2 days to about 25 days, or from 3 days to about 20 days, or from 5 days to about 15 days, or from 7 days to about 14 days, or about 10 days.

Methods and assays for determining a level of WNT activation or GSK-3 inhibition are available to a skilled person and include, for example, the methods and assays described in Liao et al., *Endocrinology*, 145(6): 2941-2949 (2004), and in U.S. Pat. No. 8,323,919, both of which are specifically incorporated by reference herein in their entireties.

Neuronal Differentiation Enhancers

As illustrated herein use of one or more neuronal differentiation enhancers can facilitate conversion of differentiated cells into the neuronal cell lineage. For example, experimental data described herein shows that neuronal differentiation enhancers can facilitate neuronal conversion of fibroblasts to the neuronal lineage.

A variety of neuronal differentiation enhancers can be used in the compositions and methods described herein. For example, neuronal differentiation enhancers can include:

basic fibroblast growth factor (bFGF; also known as FGF2), wherein human basic fibroblast growth factor is described, for example, by Abraham et al., *EMBO J.* 5: 2523-2528 (1986), the contents of which are incorporated herein by reference in its entirety; and where sequence information for human basic fibroblast growth factor is available as Genbank Accession No. NP-001997;

KHS2 (also known as SID 26759233, Neuropathiazol; ethyl 4-(methyl(2-phenyl-4,5-dihydrothiazol-4-yl)amino)benzoate);

fibroblast growth factor-8 (FGF-8; see, e.g., Gemel, J., *Genomics* 35: 253-257, (1996); Yoshiura, K., *Am. J. Med Genet.* 72: 354-362 (1997), the contents of each of which are incorporated herein by reference in its entirety); sequence information for human fibroblast growth factor 8 is available as Genbank Accession Nos. P55075, NP-149355, NP-006110, NP-149353, and NP-149354;

brain-derived neurotrophic factor (BDNF; see, e.g., Maisonpierre, P. C., *Genomics* 10: 558-568 (1991), the contents of which are incorporated herein by reference in its entirety); sequence information for human brain-derived neurotrophic factor is available as Genbank Accession No. P23560, Sonic Hedgehog (SHH), see, e.g., Marigo, *Genomics* 28: 44-51 (1995), the contents of which are incorporated herein by reference in its entirety); sequence information for human sonic hedgehog is available as Genbank Accession No. Q15465;

N2 Supplement® (available from Gibco (Catalog No. 17502048, containing recombinant human insulin, human transferrin (iron-saturated), sodium selenite, putrescine and progesterone in Phosphate Buffered Saline); or any combination thereof.

In some embodiments, the neuronal differentiation factor is basic fibroblast growth factor (bFGF).

The amounts of neuronal differentiation factors in the compositions and methods provided herein can vary, for example, depending on the number of cells to be treated, the extent of conversion to the neuronal lineage (e.g., as assessed using neuronal cell markers), and the size and duration of the culture. Concentrations can range, for example, between 0.1-200 ng/mL, 0.5-100 ng/mL, 1-50 ng/mL, 2-25 ng/mL, 3-20 ng/mL, 5-15 ng/mL, or 10 ng/mL. In a specific embodiment, 10 ng/mL bFGF is used. Suitable concentrations can be determined by assaying the differentiation potential of cells having undergone the methods described herein Neuronal differentiation factors can be added to a selected starting cell population while directing the cells into the neural lineage. Neuronal differentiation factors can also be added to a neural progenitor cell population to be converted to neural cells.

The time of contacting or mixing neuronal differentiation factors with a population of cells (to generate neural cells) can vary, for example, from about 1 day to about 30 days, or from 2 days to about 25 days, or from 3 days to about 20 days, or from 5 days to about 15 days, or from 7 days to about 14 days, or about 10 days.

SMO Agonist

The 7-pass transmembrane protein Smoothened (Smo) acts as a positive regulator of Hedgehog signaling. Hedgehog genes encode secreted proteins that undergo post-translational modifications, including autocatalytic cleavage and lipid modification (palmitoylation) at the N-terminus and cholesterol modification of the C-terminus. Patched (etch) acts as negative regulator of Hedgehog signaling and at resting state free Ptch (i.e., unbound by Hedgehog) suppresses pathway activity that has been induced by Smo (Taipale et al. (2002) Nature 418: 892). Upon binding of ligand to Hedgehog protein, however, repression of Smo is relieved, and the resulting signaling cascade leads to the activation and nuclear translocation of Gli transcription factors (Gli1, Gli2 and Gli3).

Agonists of Smo include the following:
- 3-chloro-4,7-difluoro-N-(4-(methylamino)cyclohexyl)-N-(3-(pyridin-4-yl)benzyl)benzo[b]thiophene-2-carboxamide (also called Hh-Ag1.5) is a small-molecule chemical agonist of Smoothened (Smo) receptor and is an activator of sonic hedgehog (Shh) signaling. It is available from Cellagen Technology (see, e.g., website at cellagentech.com/hh-ag1-5/);
- (3β)-Cholest-5-ene-3,20-diol activates Hedgehog (Hh) signaling ($EC_{50}$~3 μM);
- 3-Chloro-N-[trans-4-(methylamino)cyclohexyl]-N-[[3-(4-pyridinyl)phenyl]methyl]benzo[b]thiophene-2-carboxamide (also called SAG) is a potent Smoothened (Smo) receptor agonist ($K_d$=59 nM) and it potently activates the Hedgehog signaling pathway in Shh-light 2 cells ($EC_{50}$~3 nM). Induces pathway activation independently of Ptch proteins.

In some embodiments, the SMO agonist is Hh-Ag1.5.

The amounts of SMO agonist in the compositions and methods provided herein can vary, for example, depending on the number of cells to be treated, the extent of conversion to the neuronal lineage (e.g., as assessed using neuronal cell markers), and the size and duration of the culture. For example, the SMO agonists can be employed at a concentration of about 0.01 micromolar to about 1 millimolar in a solution, or about 0.1 micromolar to about 100 micromolar in a solution, or about 0.5 micromolar to about 10 micromolar in a solution, or about 1 micromolar to about 5 micromolar in a solution. In a dry formulation, the SMO agonist can be present in amounts of about 0.01 mg to about 1000 mg, or about 1 mg to about 100 mg, or about 1 mg to about 10 mg can be present in amounts of about 0.01 mg to about 1000 mg, or about 0.1 mg to about 100 mg, or about 1 mg to about 10 mg.

SMO agonists can be added to a selected starting cell population while directing the cells into the neural lineage. SMO agonists can also be added to a neural progenitor cell population to be converted to neural cells.

The time of contacting or mixing SMO agonists with a population of cells (to generate neural cells) can vary, for example, from about 1 day to about 30 days, or from 2 days to about 25 days, or from 3 days to about 20 days, or from 5 days to about 15 days, or from 7 days to about 14 days, or about 10 days.

Retinoic Acid Receptor-Gamma (BART) Agonists

As illustrated herein use of one or more agonists of retinoic acid receptor-gamma can facilitate conversion of differentiated cells into the neuronal cell lineage. Agonists of RARγ stimulate the receptor to activate transcription of various genes.

A variety of RARγ agonists can be used in the compositions and methods described herein. For example, RARγ agonists can include:
- Retinoic acid;
- CD1530 (4-(6-hydroxy-7-tricyclo[3.3.1.13,7]dec-1-yl-2-naphthalenyl)benzoic acid);
- CD666 (also known as SureCN12572388, CHEMBL97080, 4-[(E)-3-hydroxy-3-(5,5,8,8-tetramethyl-6,7-dihydronaphthalen-2-yl)prop-1-enyl]benzoic Acid),
- NRX204647 (4-((1E,3E)-3-(hydroxyimino)-3-(5,5,8,8-tetramethyl-5,6,7,8-tetrahydronaphthalen-2-yl)prop-1-en-1-yl)benzoic acid);
- retinoic acid;
- all-trans retinoic acid (ATRA);
- 9-cis retinoic acid;
- all-trans 3-4 didehydro-retinoic acid
- 4-oxo retinoic acid;
- Retinol;
- 4-[(E)-2-(5,6,7,8-tetrahydro-5,5,8,8-tetramethyl-2-naphthalenyl)-1-propenyl]benzoic acid;
- 4-(5-methoxymethyl-5-methyl-2,3,4,5-tetrahydro-1-benzo[b]oxepin-8-yl-ethynyl)-benzoic acid;
- 4-(5-ethoxymethyl-5-methyl-2,3,4,5-tetrahydrobenzo[b]oxepin-8-ylethynyl)-benzoic acid;
- 4-(5-methyl-5-propoxymethyl-2,3,4,5-tetrahydrobenzo[b]oxepin-8-ylethynyl)-benzoic acid;
- (E)-4-[2-(5-methoxymethyl-5-propyl-2,3,4,5-tetrahydrobenzo[b]oxepin-8-yl)-vinyl]-benzoic acid;
- (E)-4-[2-(5-methoxymethyl-5-methyl-2,3,4,5-tetrahydrobenzo[b]oxepin-8-yl)-vinyl]-benzoic acid;
- (E)-4-[2-(5-methyl-5-propoxymethyl-2,3,4,5-tetrahydrobenzo[b]oxepin-8-yl)-vinyl]-benzoic acid;
- 4-(5-methoxymethyl-5-methyl-2,3,4,5-tetrahydrobenzo[b]thiepin-8-ylethynyl)-benzoic acid;
- 4-(5-ethoxymethyl-5-methyl-2,3,4,5-tetrahydrobenzo[b]thiepin-8-ylethynyl)-benzoic acid;
- (E)-4-[2-(5-ethoxymethyl-5-methyl-2,3,4,5-tetrahydrobenzo[b]thiepin-8-yl) vinyl]-benzoic acid;
- (E)-4-[2-(5-methoxymethyl-5-propyl-2,3,4,5-tetrahydrobenzo[b]thiepin-8-yl)-vinyl]-benzoic acid;
- 4-(4-methoxymethyl-4-methyl-chroman-6-ylethynyl)-benzoic acid;
- (E)-4-[2-(4-methoxymethyl-4-methyl-chroman-6-yl)-vinyl]-benzoic acid; or
- any combination thereof.

Additional RARγ agonists are described in WO 2001030326; WO 2001014360; and Shimono et al. (Nat.

Med. 17: 454-460 (2011)), which are specifically incorporated herein by reference in their entireties.

Agonists of RARγ can be identified or evaluated by transactivation assays. The term "transactivation" refers to the ability of a retinoid to activate the transcription of a gene where the gene transcription is initiated by the binding of a ligand (e.g., agonist) to the RARγ. Determining the ability of a compound to transactivate a retinoic acid receptor can be performed by methods known to those of skill in the art. Examples of such methods are found in Bernard et al, *Biochem. Biophys. Res. Commun.*, 186: 977-983 (1992) and C. Apfel et al, *Proc. Nat. Sci. Acad. (USA)*, 89: 7129-7133 (1992).

The RARγ agonist can, for example, be retinoic acid.

The amounts of RARγ agonists in the compositions and methods provided herein can vary, for example, depending on the number of cells to be treated, the extent of conversion to the neuronal lineage (e.g., as assessed using neuronal cell markers), and the size and duration of the culture. For example, the RARγ agonists can be employed at a concentration of about 0.01 micromolar to about 1 millimolar in a solution, or about 0.1 micromolar to about 100 micromolar in a solution, or about 0.5 micromolar to about 10 micromolar in a solution, or about 1 micromolar to about 5 micromolar in a solution. In a dry formulation, the RARγ agonists can be present in amounts of about 0.01 mg to about 1000 mg, or about 1 mg to about 100 mg, or about 1 mg to about 10 mg can be present in amounts of about 0.01 mg to about 1000 mg, or about 0.1 mg to about 100 mg, or about 1 mg to about 10 mg.

RARγ agonists can be added to a selected starting cell population while directing the cells into the neural lineage. RARγ agonists can also be added to a neural progenitor cell population to be converted to neural cells.

The time of contacting or mixing RARγ agonists with a population of cells (to generate neural cells) can vary, for example, from about 1 day to about 30 days, or from 2 days to about 25 days, or from 3 days to about 20 days, or from 5 days to about 15 days, or from 7 days to about 14 days, or about 10 days.

DNA Methyltransferase (DNMT) Inhibitors

As illustrated herein use of one or more DNA methyltransferase (DNMT) inhibitors can facilitate conversion of differentiated cells into the neuronal cell lineage.

DNA methyltransferases are enzymes that transfer methyl groups to DNA. Inhibitors of DNA methyltransferases can reactivate the expression of genes that have been repressed by DNA methylation. As illustrated herein, DNA methyltransferase inhibitors can improve the conversion of selected starting cells to neuronal cells.

Exemplary DNA methyltransferase inhibitors can include antibodies that bind to DNA methyltransferases, dominant negative variants of DNA methyltransferases, and siRNA and antisense nucleic acids that suppress expression of DNMT. DNA methyltransferase inhibitors include, but are not limited to, RG108 (N-Phthalyl-L-tryptophan, available, e.g., from Sigma-Aldrich), 5-aza-C(5-azacitidine or azacitidine) (see, e.g., Schermelleh, et al., *Nature Methods* 2:751-6 (2005)), 5-aza-2'-deoxycytidine (5-aza-CdR) (see, e.g., Zhu, *Clinical Medicinal Chemistry* 3(3):187-199 (2003)), decitabine (see, e.g., Gore, *Nature Clinical Practice Oncology* 2:S30-S35 (2005)), doxorubicin (see, e.g., Levenson, *Molecular Pharmacology* 71:635-637 (2007)), EGCG ((−)-epigallocatechin-3-gallate) (see, e.g., Fang, et al., *Cancer Research* 63:7563-7570 (2003)), RG108 (see, e.g., Carninci, et al., WO2008/126932, incorporated herein by reference) and zebularine (see, Carninci, supra).

In some embodiments, the DNA methyltransferase inhibitor is RG108, which has the following structure.

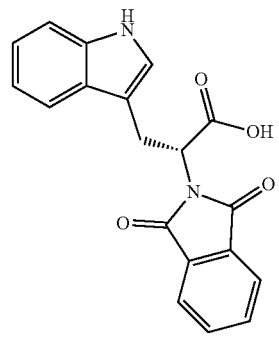 [SMILES: O=C(O)[C@@H](Cc1c[nH]c2ccccc12)N1C(=O)c2ccccc2C1=O]

The amounts of DNA methyltransferase inhibitors in the compositions and methods provided herein can vary, for example, depending on the number of cells to be treated, the extent of conversion to the neuronal lineage (e.g., as assessed using neuronal cell markers), and the size and duration of the culture. For example, the DNA methyltransferase inhibitors can be employed at a concentration of about 0.01 micromolar to about 1 millimolar in a solution, or about 0.1 micromolar to about 100 micromolar in a solution, or about 0.5 micromolar to about 50 micromolar in a solution, or about 1 micromolar to about 25 micromolar in a solution, or about 10 micromolar. In a dry formulation, the DNA methyltransferase inhibitors can be present in amounts of about 0.01 mg to about 1000 mg, or about 1 mg to about 100 mg, or about 1 mg to about 10 mg can be present in amounts of about 0.01 mg to about 1000 mg, or about 0.1 mg to about 100 mg, or about 1 mg to about 10 mg.

DNA methyltransferase inhibitors can be added to a selected starting cell population while directing the cells into the neural lineage. DNA methyltransferase inhibitors can also be added to a neural progenitor cell population to be converted to neural cells.

The time of contacting or mixing DNA methyltransferase inhibitors with a population of cells (to generate neural cells) can vary, for example, from about 1 day to about 30 days, or from 2 days to about 25 days, or from 3 days to about 20 days, or from 5 days to about 15 days, or from 7 days to about 14 days, or about 10 days.

Histone Demethylase Inhibitors

As illustrated herein use of one or more histone demethylase inhibitors can facilitate conversion of differentiated cells into the neuronal cell lineage.

Histone demethylases remove methyl groups from histone. The lysine-specific demethylase 1 (LSD1, also called KDM1, AOF2, or BHC110) is a histone demethylase that suppresses gene expression by converting di-methylated lysines on histone H3 to monomethylated and unmethylated lysines. Histone methylation can influence epigenetic patterns of gene expression due to association with active promoters. As illustrated herein use of one or more inhibitors of histone demethylase enzymes can facilitate conversion of differentiated cells into the neural lineage.

Exemplary inhibitors of histone demethylase include, but are not limited to, parnate (also called tranylcypromine sulfate) or an equivalent salt of parnate, and phenelzine (Nardil, 2-phenylethylhydrazine). See, also, Huang et al., *Proc Natl Acad Sci USA.* 104(19): 8023-8028 (2007); Bi, X. et al., *Bioorg. Med. Chem. Lett.* 16:3229-3232 (2006);

International Patent Application Nos. WO2007/021839 and WO2008/127734. MAO inhibitors can also serve as epigenetic modulators.

In some embodiments, the histone demethylase inhibitor is parnate.

The amounts of histone demethylase inhibitors in the compositions and methods provided herein can vary, for example, depending on the number of cells to be treated, the extent of conversion to the neuronal lineage (e.g., as assessed using neuronal cell markers), and the size and duration of the culture. For example, the histone demethylase inhibitors can be employed at a concentration of about 0.01 micromolar to about 1 millimolar in a solution, or about 0.01 micromolar to about 50 micromolar in a solution, or about 0.1 micromolar to about 25 micromolar in a solution, or about 0.5 micromolar to about 10 micromolar in a solution, or about 2 micromolar. In a dry formulation, the histone demethylase inhibitors can be present in amounts of about 0.01 mg to about 1000 mg, or about 1 mg to about 100 mg, or about 1 mg to about 10 mg can be present in amounts of about 0.01 mg to about 1000 mg, or about 0.1 mg to about 100 mg, or about 1 mg to about 10 mg.

Histone demethylase inhibitors can be added to a selected starting cell population while directing the cells into the neural lineage. Histone demethylase inhibitors can also be added to a neural progenitor cell population to be converted to neural cells.

The time of contacting or mixing histone demethylase inhibitors with a population of cells (to generate neural cells) can vary, for example, from about 1 day to about 30 days, or from 2 days to about 25 days, or from 3 days to about 20 days, or from 5 days to about 15 days, or from 7 days to about 14 days, or about 10 days.

Autophagy Regulator

As illustrated herein use of one or more autophagy regulators can facilitate conversion of differentiated cells into the neuronal cell lineage.

Examples of autophagy regulators include SMER28, apigenin, berberine, beta-elemene, capsaicin, curcumin, genistein, kaempferol, oridonin, paclitaxel, quercetin, resveratrol, silybin, triptolide, and ursolic acid.

In some embodiments, the autophagy regulator is SMER28.

In addition to regulating autophagy, SMER28 (6-bromo-N-2-propenyl-4-quinazolinamine) enhances A53T alpha-synuclein clearance in PC-12 cells independent of rapamycin treatment. It appears to act independent of the mTOR pathway, but combined treatment with saturating rapamycin concentration enhances the effect of either compound alone on A53T alpha-synuclein clearance; autophagy inducers may prove useful in the treatment of neurodegenerative and infectious diseases and cancer.

The amounts of autophagy regulators in the compositions and methods provided herein can vary, for example, depending on the number of cells to be treated, the extent of conversion to the neuronal lineage (e.g., as assessed using neuronal cell markers), and the size and duration of the culture. For example, the autophagy regulators can be employed at a concentration of about 0.01 micromolar to about 500 micromolar in a solution, or about 0.1 micromolar to about 100 micromolar in a solution, or about 0.5 micromolar to about 50 micromolar in a solution, or about 1 micromolar to about 25 micromolar in a solution, or about 10 micromolar. In a dry formulation, the autophagy regulators can be present in amounts of about 0.01 mg to about 1000 mg, or about 1 mg to about 100 mg, or about 1 mg to about 10 mg can be present in amounts of about 0.01 mg to about 1000 mg, or about 0.1 mg to about 100 mg, or about 1 mg to about 10 mg.

Autophagy regulators can be added to a selected starting cell population while directing the cells into the neural lineage. Autophagy regulators can also be added to a neural progenitor cell population to be converted to neural cells.

The time of contacting or mixing autophagy regulators with a population of cells (to generate neural cells) can vary, for example, from about 1 day to about 30 days, or from 2 days to about 25 days, or from 3 days to about 20 days, or from 5 days to about 15 days, or from 7 days to about 14 days, or about 10 days.

Transcription Factor/Transcriptional Activators

Figure 4A:
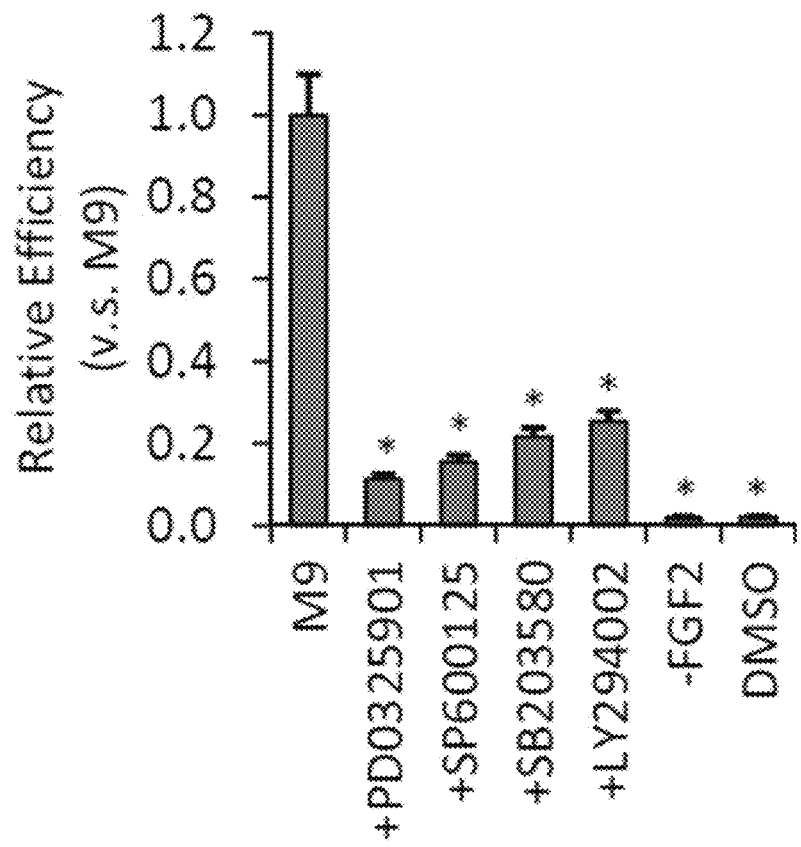
FIG. 4A-4L illustrates establishment of neural fate by chemically inducing an intrinsic neural program.
Figure 4B:
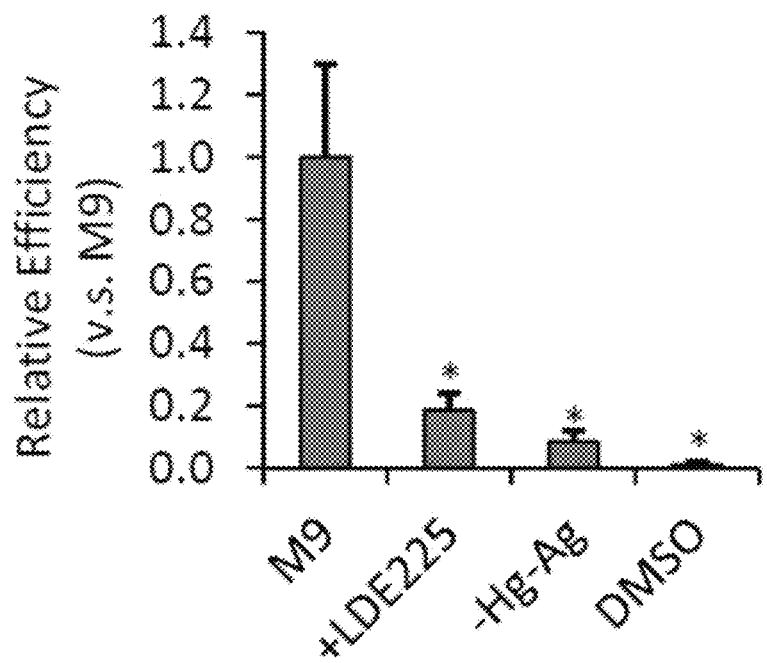
Figure 4C:
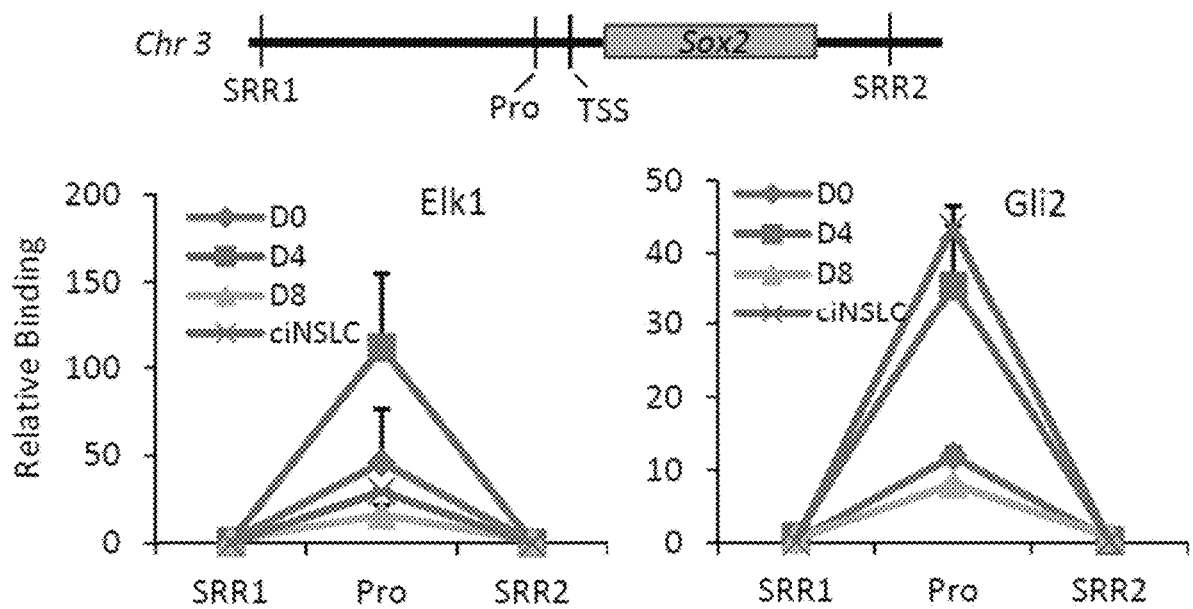
Figure 4D:
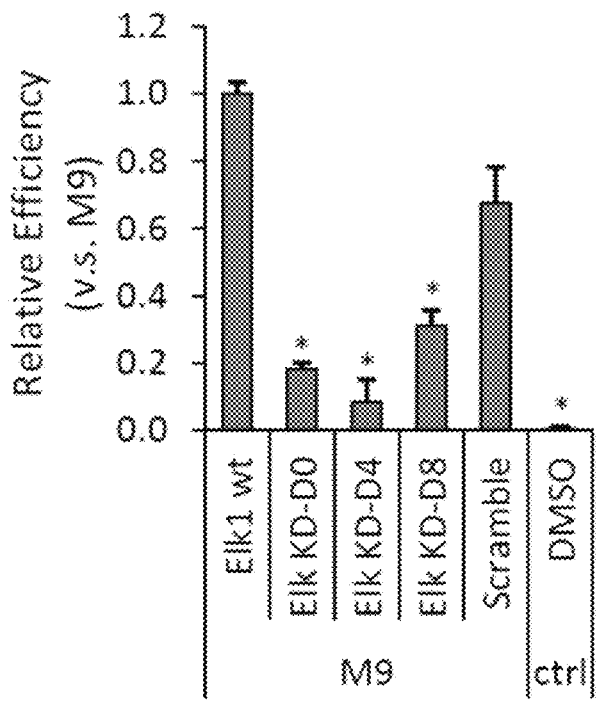
Figure 4E:
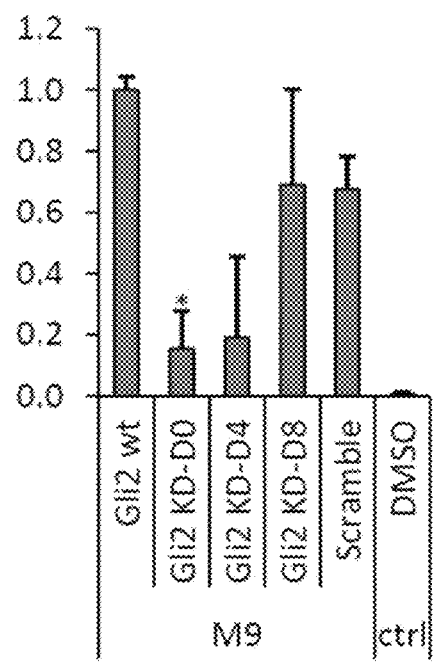
Figure 4F:
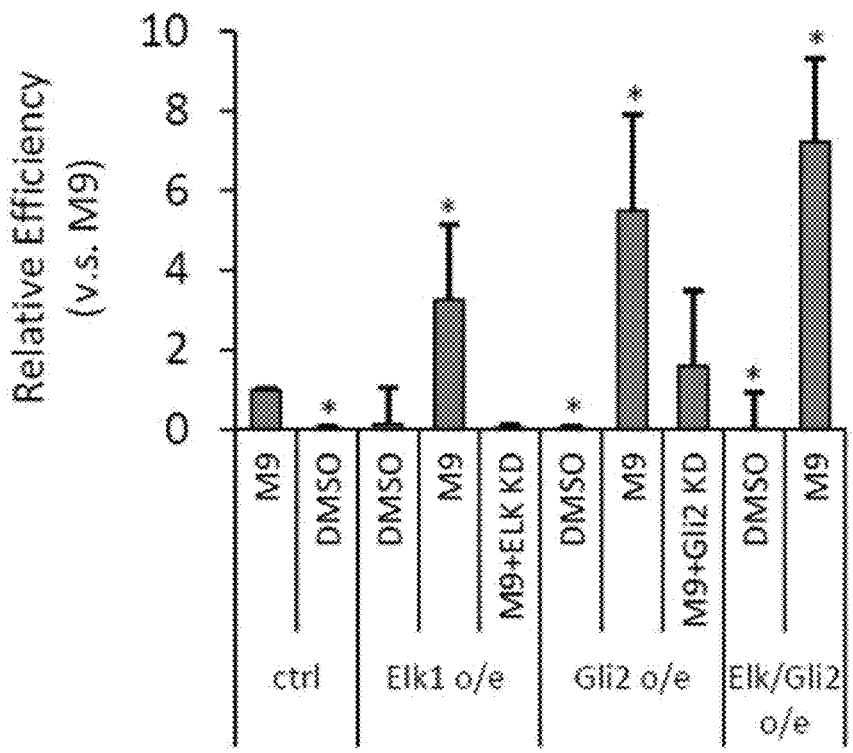
Figure 4G:
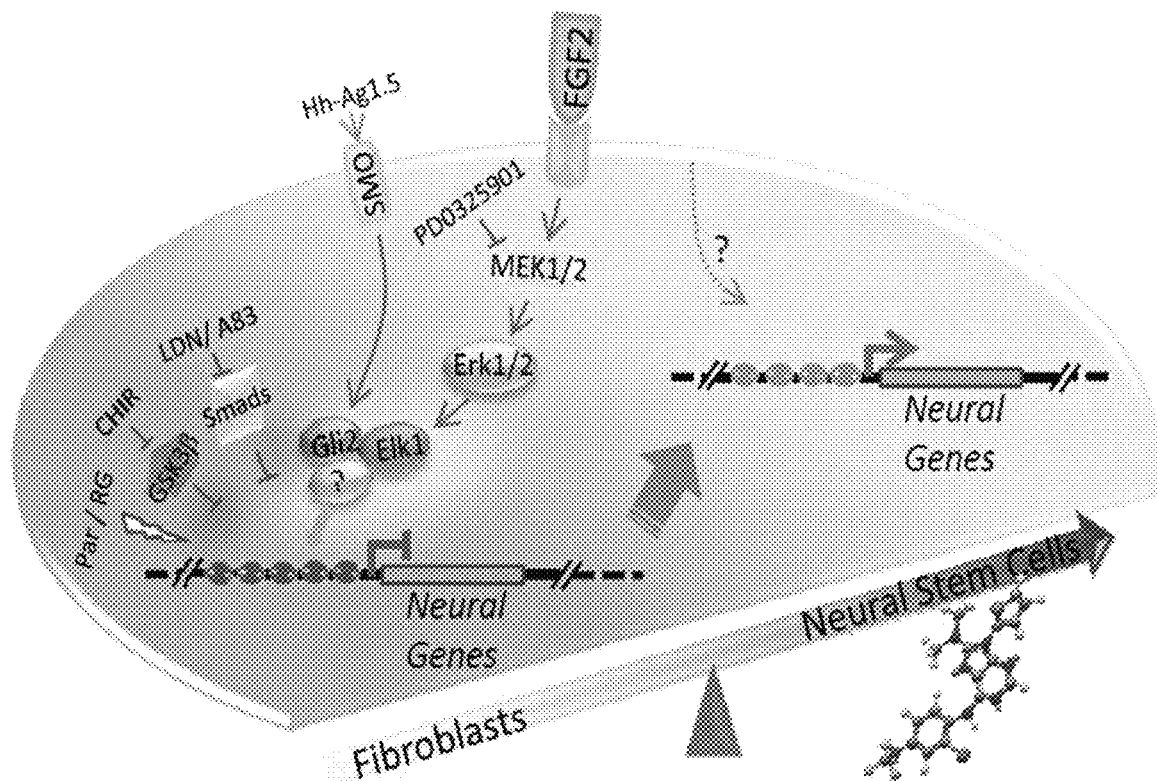

As illustrated herein, expression of Gli2 and/or Elk2 transcription factors/activators increases the proportion of cells that are reprogrammed to cross lineage boundaries and converted into neuronal progenitor cells or mature functional neuronal cells (see e.g., FIGS. 4D-4F).

An exemplary sequence for a human Gli2 protein is shown below (SEQ ID NO:1).

```
   1    METSASATAS  EKQEAKSGIL  EAAGFPDPGK  KASPLVVAAA
  41    AAAAVAAQGV  PQHLLPPFHA  PLPIDMRHQE  GRYHYEPHSV
  81    HGVHGPPALS  GSPVISDISL  IRLSPHPAGP  GESPFNAPHP
 121    YVNPHMEHYL  RSVHSSPTLS  MISAARGLSP  ADVAQEHLKE
 161    RGLFGLPAPG  TTPSDYYHQM  TLVAGHPAPY  GDLLMQSGGA
 201    ASAPHLHDYL  NPVDVSRFSS  PKVTPRLSRK  RALSISPLSD
 241    ASLDLQRMIR  TSPNSLVAYI  NNSRSSSAAS  GSYGHLSAGA
 281    LSPAFTFPHP  INPVAYQQIL  SQQRGLGSAF  GHTPPLIQPS
 321    PTFLAQQPMA  LTSINATPTQ  LSSSSNCLSD  TNQNKQSSES
 361    AVSSTVNPVA  IHKRSKVKTE  PEGLRPASPL  ALTQGQVSGH
 401    GSCGCALPLS  QEQLADLKED  LDRDDCKQEA  EVVIYETNCH
 441    WEDCTKEYDT  QEQLVHHINN  EHIHGEKKEF  VCRWQACTRE
 481    QKPFKAQYML  VVHMRRHTGE  KPHKCTFEGC  SKAYSRLENL
 521    KTHLRSHTGE  KPYVCEHEGC  NKAFSNASDR  AKHQNRTHSN
 561    EKPYICKIPG  CTKRYTDPSS  LRKHVKTVHG  PDAHVTKKQR
 601    NDVHLRTPLL  KENGDSEAGT  EPGGPESTEA  SSTSQAVEDC
 641    LHVRAIKTES  SGLCQSSPGA  QSSCSSEPSP  LGSAPNNDSG
 681    VEMPGTGPGS  LGDLTALDDT  PPGADTSALA  APSAGGLQLR
 721    KHMTTMHRFE  QLKKEKLKSL  KDSCSWAGPT  PHTRNTKLPP
 761    LPGSGSILEN  FSGSGGGPA   GLLPNPRLSE  LSASEVTMLS
 801    QLQERRDSST  STVSSAYTVS  RRSSGISPYF  SSRRSSEASP
 841    LGAGRPHNAS  SADSYDPIST  DASRRSSEAS  QCSGGSGLLN
 881    LTPAQQYSLR  AKYAAATGGP  PPTPLPGLER  MSLRTRLALL
 921    DAPERTLPAG  CPRPLGPRRG  SDGPTYGHGH  AGAAPAFPHE
 961    APGGGARRAS  DPVRRPDALS  LPRVQRFHST  HNVNPGPLPP
1001    CADRRGLRLQ  SHPSTDGGLA  RGAYSPRPPS  ISENVAMEAV
1041    AAGVDGAGPE  ADLGLPEDDL  VLPDDVVQYI  KAHASGALDE
```

-continued

```
1081    GTGQVYPTES  TGFSDNPRLP  SPGLHGQRRM  VAADSNVGPS

1121    APMLGGCQLG  FGAPSSLNKN  NMPVQWNEVS  SGTVDALASQ

1161    VKPPPFPQGN  LAVVQQKPAF  GQYPGYSPQG  LQASPGGLDS

1201    TQPHLQPRSG  APSQGIPRVN  YMQQLRQPVA  GSQCPGMTTT

1241    MSPHACYGQV  HPQLSPSTIS  GALNQFPQSC  SNMPAKPGHL

1281    GHPQQTEVAP  DPTTMGNRHR  ELGVPDSALA  GVPPPHPVQS

1321    YPQQSHHLAA  SMSQEGYHQV  PSLLPARQPG  FMEPQTGPMG

1361    VATAGFGLVQ  PRPPLEPSPT  GRHRGVRAVQ  QQLAYARATG

1401    HAMAAMPSSQ  ETAEAVPKGA  MGNMGSVPPQ  PPPQDAGGAP

1441    DHSMLYYYGQ  IHMYEQDGGL  ENLGSCQVMR  SQPPQPQACQ

1481    DSIQPQPLPS  PGVNQVSSTV  DSQLLEAPQI  DFDAIMDDGD

1521    HSSLFSGALS  PSLLHSLSQN  SSRLTTPRNS  LTLPSIPAGI

1561    SNMAVGDMSS  MLTSLAEESK  FLNMMT
```

An exemplary sequence for a human Elk1 protein is shown below (SEQ ID NO:2).

```
  1     MDPSVTLWQF  LLQLLREQGN  GHIISWTSRD  GGEFKLVDAE

41     EVARLWGLRK  NKTNMNYDKL  SRALRYYDK   NIIRKVSGQK

81     FVYKFVSYPE  VAGCSTEDCP  PQPEVSVTST  MPNVAPAAIH

121     AAPGDTVSGK  PGTPKGAGMA  GPGGLARSSR  NEYMRSGLYS

161     TFTIQSLQPQ  PPPHPRPAVV  LPNAAPAGAA  APPSGSRSTS

201     PSPLEACLEA  EEAGLPLQVI  LTPPEAPNLK  SEELNVEPGL

241     GRALPPEVKV  EGPKEELEVA  GERGFVPETT  KAEPEVPPQE

281     GVPARLPAVV  MDTAGQAGGH  AASSPEISQP  QKGRKPRDLE

321     LPLSPSLLGG  PGPERTPGSG  SGSGLQAPGP  ALTPSLLPTH

361     TLTPVLLTPS  SLPPSIHFWS  TLSPIAPRSP  AKLSFQFPSS

401     GSAQVHIPSI  SVDGLSTPVV

421     LSPGPQKP
```

Accordingly, the methods described herein can include expression of the Gli2 and/or Elk1 protein with treatment that includes the compositions described herein. Such proteins can be expressed from a transgene or expression cassette that includes a promoter that is operably linked to a nucleic acid segment that encodes the Gli2 or Elk1 protein. The promoter can be a heterologous promoter, meaning that the promoter is not the promoter that naturally drives expression of the Gli2 or Elk1 protein. Alternatively, the promoter can be the natural promoter that does drive expression of the Gli2 or Elk1 protein.

Expression vectors (plasmids) for overexpression of Elk1 (e.g., addgene 27156) or G/12 (e.g., addgene 37671) can also be obtained from Addgene and used for increasing the expression of the Gli2 and/or Elk1 proteins.

The transcription factors/activators that can increase the proportion of cells that are reprogrammed to cross lineage boundaries and that are converted into neuronal progenitor cells or mature functional neuronal cells includes related transcription factors with at least 70%, or at least 75%, or at least 80%, or at least 85%, or at least 90%, or at least 95%, or at least 97% sequence identity to SEQ ID NO:1 or 2.

Selected Starting Cells

A selected starting population of cells may be derived from essentially any source, and may be heterogeneous or homogeneous. The term "selected cell" or "selected cells" is also used to refer to starting cells. In certain embodiments, the selected starting cells to be treated as described herein are adult cells, including essentially any accessible adult cell type(s). In other embodiments, the selected starting cells treated according to the invention are adult stem cells, progenitor cells, or somatic cells. In still other embodiments, the selected starting cells treated with any of the compositions and/or methods described herein include any type of cell from a newborn, including, but not limited to newborn cord blood, newborn stem cells, progenitor cells, and tissue-derived cells (e.g., somatic cells). In some embodiments, the starting population of cells does not include pluripotent stem cells. In other embodiments, the starting population of cells can include pluripotent stem cells. Accordingly, a starting population of cells that is reprogrammed by the compositions and/or methods described herein, can be essentially any live cell type, particularly a somatic cell type.

As illustrated herein, fibroblasts can be reprogrammed to cross lineage boundaries and to be directly converted to other cell types such as neuronal progenitor or mature functional neuronal cell types. Various cell types from all three germ layers have been shown to be suitable for somatic cell reprogramming by genetic manipulation, including, but not limited, to liver and stomach (Aoi et al., Science 321 (5889):699-702 (2008); pancreatic β cells (Stadtfeld et al., Cell Stem Cell 2: 230-40 (2008); mature B lymphocytes (Hanna et al., Cell 133: 250-264 (2008); human dermal fibroblasts (Takahashi et al., Cell 131, 861-72 (2007); Yu et al., Science 318(5854) (2007); Lowry et al., Proc Natl Acad Sci USA 105, 2883-2888 (2008); Aasen et al., Nat Biotechnol 26(11): 1276-84 (2008); meningiocytes (Qin et al., J Biol Chem 283(48):33730-5 (2008); neural stem cells (DiStefano et al., Stem Cells Devel. 18(5): (2009); and neural progenitor cells (Eminli et al., Stem Cells 26(10): 2467-74 (2008). Any such cells can be reprogrammed and/or programmed by use of the compositions and methods described herein.

The cells can be autologous or allogeneic cells (relative to a subject to be treated or who may receive the cells).

Reprogramming Methods

Selected starting cells are treated for a time and under conditions sufficient to convert the starting cells across lineage and/or differentiation boundaries to form neuronal progenitor cells or mature functional neuronal cells.

Selected starting cells can be incubated with a composition that includes at least one BMP type 1 receptor ALK2/3 inhibitors, at least one TGF-beta inhibitor, at least one WNT inhibitor, at least one neuronal differentiation enhancer, at least one SMO agonist, at least one retinoic acid receptor γ agonist, at least one DNA methyltransferase inhibitor, at least one histone demethylase inhibitor, at least one autophagy regulator, or any combination thereof. The composition can contain at least two of the agents, or at least three of the agents, or at least four of the agents, or at least five of the agents, or at least six of the agents, or at least seven of the agents, or at least eight of the agents. This composition is referred to herein as the M9 cocktail.

The time for conversion of starting cells into neuronal progenitor and mature neuronal cells can vary. For example, the starting cells can be incubated with the M9 reprogramming cocktail until neuronal cell markers are expressed. Such neuronal cell markers can include Tuj1, Map2, NeuN, Sox2, synapsins (e.g., Syn1 and Syn2), synaptophysin, synaptotagmins (e.g., Syt1, Syt4, Sytl3, Sytl6), NeuroD, Is11, and cholineacetyltransferase (ChAT, e.g., vascular ChAT (VChAT)). The starting cells can be incubated with the M9 reprogramming cocktail until oligodendrocyte markers are expressed, such as O4. In some cases, starting cells can be incubated with the M9 reprogramming cocktail until astrocyte markers are expressed, such as GFAP. In other cases, starting cells can be incubated with the M9 reprogramming cocktail until vGlut1-positive glutamatergic neurons and/or GABA-positive GABAergic neurons are detected Neuronal progenitor cells can, for example, be detected by observing expression of Tuj1, a neuron-specific class III beta-tubulin. Human β-Tubulin 3 is a 50,432 Dalton structural protein (450 amino acid) expressed in neurons of the peripheral and central nervous systems. It contributes to microtubule stability in neuronal cell bodies and axons, and plays a rote in axonal transport.

The starting cell(s) can also be incubated with the reprogramming composition until a more mature neuronal cell marker is expressed by the cells. For example, the starting cell(s) can be incubated with the reprogramming composition until expression of the Tau marker is observed. TAU is a neuronal microtubule-associated protein found predominantly on axons. The starting cell(s) can be incubated with the reprogramming composition until expression of the NeuN marker is observed. NeuN (neuronal nuclei) is expressed by mature (post-mitotic) neurons throughout the nervous system. Similarly, the starting cell(s) can be incubated with the reprogramming composition until the more mature neuronal cell marker MAP2 is expressed by the cells. MAP2 is also a microtubule-associated protein with a role in neurogenesis.

The starting cell(s) can also be incubated with the reprogramming composition until the more mature neuronal cell marker Synapsin I is expressed by the cells. Synapsin I is a major phosphoprotein in synaptic terminals.

The time for conversion of starting cells into neuronal progenitor and mature neuronal cells can therefore vary. For example, the starting cells can be incubated with the composition under cell culture conditions for at least about 3 days, or for at least about 4 days, or for at least about 5 days, or for at least about 6 days, or for at least about 7 days, or for at least about 8 days, or for at least about 9 days, or for at least about 10 days, or for at least about 11 days, or for at least about 12 days, or for at least about 13 days, or for at least about 14 days, or for at least about 15 days, or for at least about 16 days, or for at least about 17 days, or for at least about 18 days, or for at least about 19 days.

In some embodiments, the starting cells can be incubated with the composition under cell culture conditions for about 3 days to about 30 days, or about 4 days to about 25 days, or about 5 days to about 20 days, or about 7 days to about 15 days, or about 8 days to about 12 days, or about 10 days.

As illustrated herein, a composition of nine chemical compounds (at least one BMP type I receptor ALK2/3 inhibitor, at least one TGF-beta inhibitor, at least one WNT inhibitor, at least one neuronal differentiation enhancer, at least one SMO agonist, at least one retinoic acid receptor γ agonist, at least one DNA methyltransferase inhibitor, at least one histone demethylase inhibitor, at least one autophagy regulator) was sufficient to efficiently induce over 25% human fibroblasts to form Sox2 Nestin double-positive cells after ten days of incubation. Semi-quantitative RT-PCR confirmed the expression of other neural stem cell genes, including Pax6, Sox2, Ascl1, and Olig2.

The starting cells can be incubated with the M9 cocktail that is combined with a cell culture medium.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are available to those skilled in the art.

Examples of cell culture media that can be employed Dulbecco's modified Eagle's medium (e.g., supplemented with 10% fetal bovine serum, 0.1 mM nonessential amino acids, and 2 mM Glutamax), N2B27 medium (e.g., containing 50% Neural basal medium and 50% DMEM/F12 medium supplemented with 1% GlutaMax, 1% N2 (Life Technologies), 2% B27 (Gibco), and 0.1% BSA)), or neural stem cell medium (NSC medium, 50% Neural basal, 50% DMEM/F12/Glutamax, 1×N2, 1×B27 without vitamin A, 0.075% BSA, 0.1 mM nonessential amino acids, 20 ng/ml bFGF, 20 ng/ml EGF).

For example, when the medium contains the M9 cocktail, the composition can include 50% Neural basal, 50% DMEM/F12/Glutamax, 1×N2, 1×B27 without vitamin A, 0.075% BSA, 0.1 mM nonessential amino acids, CHIR99021 at 3 μM, LDN193189 at 100 nM, A83-01 at 0.5 μM, Hh-Ag1.5 at 0.5 retinoic acid at 1 μM, SMER28 at 10 μM, RG108 at 10 μM, Parnate at 2 μM, and bFGF at 10 ng/ml.

If more mature neuronal cells are desired the cells can be cultured within, or transferred after culture in the DMEM or N2B27 medium to a maturation medium. One example of a maturation medium is the N2B27 medium that contains 0.5% Albumin, plus 20 ng ml$^{-1}$ GDNF (R&D Systems), 10 ng ml$^{-1}$ BDNF (R&D Systems), 10 ng ml−1 NT3 (R&D Systems), and 3 μM Forskolin (Tocris).

Examples of commercially available media include, but are not limited to, Dulbecco's Modified Eagle's Medium (DMEM), Minimal Essential Medium (MEM), Basal Medium Eagle (BME), RPM1 1640, Ham's F-10, Ham's F-12, a-Minimal Essential Medium (aMEM), Glasgow's Minimal Essential Medium (G-MEM), Iscove's Modified Dulbecco's Medium, or a general purpose media modified for use with pluripotent cells, such as X-VIVO (Lonza) or a hematopoietic base media.

The starting cells can be dispersed in a cell culture medium that contains the M9 cocktail at a density that permits cell expansion. For example, about 1 to $10^{10}$ cells can be contacted with the M9 cocktail in a selected cell culture medium, especially when the cells are maintained at a cell density of about 1 to about $10^8$ cells per milliliter, or at a density of about 100 to about $10^7$ cells per milliliter, or at a density of about 1000 to about $10^6$ cells per milliliter.

Such methods can therefore be used to generate a population of neuronal cells that can be transplanted into a subject or used for experimentation.

In some embodiments, a reprogrammed population of cells can be frozen at liquid nitrogen temperatures, stored for periods of time, and then thawed for use at a later date. If frozen, a population of reprogrammed cells can be stored in a 10% DMSO, 50% FCS, 40% RPMI 1640 medium. Once thawed, the cells can be expanded by culturing the cells in an appropriate medium that can contain selected growth factors, vitamins, feeder cells, and other components selected by a person of skill in the art.

Treatment

The reprogrammed cells and/or compositions containing the M9 cocktail (with or without reprogrammed cells) described herein can also be employed in a method of treating a subject with a neuronal disease, condition, or injury. For example, the M9 cocktail can be administered to a patient to treat a neuronal disease, condition, or injury.

Examples of diseases, conditions, and injuries that can be treated using the reprogrammed cells and compositions (containing any of the compounds described herein with or without reprogrammed cells include Amyotrophic lateral sclerosis (ALS), Alzheimer's disease, Parkinson's disease, multiple sclerosis, Primary lateral sclerosis (PLS), Progressive bulbar palsy, Pseudobulbar palsy, Progressive muscular atrophy, Spinal muscular atrophy (SMA), including Type I (also called Werdnig-Hoffmann disease), Type II, Type III (Kugelberg-Welander disease), Fazio-Londe disease, Huntington's disease, Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, post-polio syndrome, stroke, head trauma, spinal cord injury, and the like.

Diseases and conditions that can be treated include those that occur as a consequence of genetic defect, physical injury, environmental insult or conditioning, bad health, obesity and other disease risk factors commonly known by a person of ordinary skill in the art.

Efficacy of treatment can be monitored by clinically accepted criteria and tests, which include for example, using electromyography (EMG), which is used to diagnose muscle and nerve dysfunction and spinal cord disease, and measure the speed at which impulses travel along a particular nerve. EMG records the electrical activity from the brain and/or spinal cord to a peripheral nerve root (found in the arms and legs) that controls muscles during contraction and at rest. One can also monitor efficacy of treatment using a nerve conduction velocity study to measure electrical energy to test the nerve's ability to send a signal, as well as laboratory screening tests of blood, urine, as well as magnetic resonance imaging (MRI), which uses computer-generated radio waves and a powerful magnetic field to produce detailed images of body structures including tissues, organs, bones, and nerves to detect and monitor degenerative disorders. In some embodiments, efficacy of treatment can also be assessed by a muscle or nerve biopsy, which can help confirm nerve disease and nerve regeneration. A small sample of the muscle or nerve is removed under local anesthetic and studied under a microscope. The sample may be removed either surgically, through a slit made in the skin, or by needle biopsy, in which a thin hollow needle is inserted through the skin and into the muscle. A small piece of muscle remains in the hollow needle when it is removed from the body. In some embodiments, efficacy of treatment can also be monitored by a transcranial magnetic stimulation to study areas of the brain related to motor activity.

Administration of Reprogrammed Cells

Reprogrammed cells generated as described herein can be employed for tissue reconstitution or regeneration in a human patient or other subjects in need of such treatment. The cells are administered in a manner that permits them to graft or migrate to a diseased or injured tissue site and to reconstitute or regenerate the functionally deficient area. Devices are available that can be adapted for administering cells, for example, into the spinal cord or other parts of the central or peripheral nervous system.

Reprogrammed cells can be administered to reconstitute the neuronal cell population in the spinal cord, brain, or at an alternative desired location. The cells may be administered to a recipient by local injection, or by systemic injection. In some embodiments, the cells can be administered parenterally by injection into a convenient cavity or by intramuscular injection.

Many cell types are capable of migrating to an appropriate site for regeneration and differentiation within a subject. To determine the suitability of cell compositions for therapeutic administration, the cells can first be tested in a suitable animal model. At one level, cells are assessed for their ability to survive and maintain their phenotype in vivo. Cells can also be assessed to ascertain whether they migrate to diseased or injured sites in vivo, or to determine an appropriate number of cells to be administered. Cell compositions can be administered to immunodeficient animals (such as nude mice, or animals rendered immunodeficient chemically or by irradiation). Tissues can be harvested after a period of regrowth, and assessed as to whether the administered cells or progeny thereof are still present, are alive, and/or have migrated to desired or undesired locations.

Injected cells can be traced by a variety of methods. For example, cells containing or expressing a detectable label (such as green fluorescent protein, or beta-galactosidase) can readily be detected. The cells can be pre-labeled, for example, with tdTomato, BrdU or [$^3$H] thymidine, or by introduction of an expression cassette that can express green fluorescent protein, or beta-galactosidase. Alternatively, the reprogrammed cells can be detected by their expression of a cell marker that is not expressed by the animal employed for testing (for example, a human-specific antigen or tdTomato). The presence and phenotype of the administered population of reprogrammed cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for human polynucleotides A number of animal models of motor neuron diseases are available for such testing, for example as the S0D1(G93A) mutant mouse and SMA (B6.129-Smnl$^{tm1jmel}$) mouse models from Jackson laboratories.

A reprogrammed population of cells can be introduced by injection, catheter, implantable device, or the like. A population of reprogrammed cells can be administered in any physiologically acceptable excipient or carrier that does not adversely affect the cells.

A population reprogrammed cells can be supplied in the form of a pharmaceutical composition. Such a composition can include an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The choice of the cellular excipient and any accompanying constituents of the composition that includes a population of reprogrammed cells can be adapted to optimize administration by the route and/or device employed.

A composition that includes a population of reprogrammed cells can also include or be accompanied by one or more other ingredients that facilitate engraftment or functional mobilization of the reprogrammed cells. Suitable ingredients include matrix proteins that support or promote adhesion of the reprogrammed cells, or complementary cell types, such as glial and/or muscle cells. In another embodiment, the composition may include physiologically acceptable matrix scaffolds, Such physiologically acceptable matrix scaffolds can be resorbable and/or biodegradable.

The population of reprogrammed cells generated by the methods described herein can include low percentages of non-neuronal cells (e.g., fibroblasts). For example, a population of reprogrammed cells for use in compositions and for administration to subjects can have less than about 90% non-neuronal cells, less than about 85% non-neuronal cells, less than about 80% non-neuronal cells, less than about 75% non-neuronal cells, less than about 70% non-neuronal cells, less than about 65% non-neuronal cells, less than about 60% non-neuronal cells, less than about 55% non-neuronal cells, less than about 50% non-neuronal cells, less than about 45% non-neuronal cells, less than about 40% non-neuronal cells, less than about 35% non-neuronal cells, less than about 30% non-neuronal cells, less than about 25% non-neuronal cells, less than about 20% non-neuronal cells, less than about 15% non-neuronal cells, less than about 12% non-neuronal cells, less than about 10% non-neuronal cells, less than about 8% non-neuronal cells, less than about 6% non-neuronal cells, less than about 5% non-neuronal cells, less than about 4% non-neuronal cells, less than about 3% non-neuronal cells, less than about 2% non-neuronal cells, or less than about 1% non-neuronal cells of the total cells in the cell population.

Pharmaceutical Compositions

The invention also relates to compositions containing a selection of some of the following chemical agents: at least one BMP type I receptor ALK2/3 inhibitor, at least one TGF-beta inhibitor, at least one WNT inhibitor, at least one neuronal differentiation enhancer, at least one SMO agonist, at least one retinoic acid receptor γ agonist, at least one DNA methyltransferase inhibitor, at least one histone demethylase inhibitor, and/or at least one autophagy regulator. For example, the composition can contain at least two of the agents, or at least three of the agents, or at least four of the agents, or at least five of the agents, or at least six of the agents, or at least seven of the agents, or at least eight of the agents. The compositions can also contain reprogrammed cells.

The compositions of the invention can be pharmaceutical compositions. In some embodiments, the compositions can include a pharmaceutically acceptable carrier. By "pharmaceutically acceptable" it is meant a carrier, diluent, excipient, and/or salt that is compatible with the other ingredients of the formulation, and not deleterious to the recipient thereof.

In some embodiments, the composition is a cell reprogramming composition.

The compositions can contain any of the agent(s) or compound(s) described herein in an amount sufficient to reprogram a cell into a neuronal cell type. For example, the compositions can contain any of the agent(s) or compound(s) described herein in an amount sufficient to induce a cell to express Sox2, Nestin, Pax6, Sox2, Ascl1, Olig2, or Tuj1, and/or in an amount sufficient to induce a cell to express Tan, and/or in an amount sufficient to induce a cell to express NeuN, and/or in an amount sufficient to induce a cell to express MAP2, and/or in an amount sufficient to induce a cell to express Synapsin. The cell contacted or treated by the compositions (whether in vitro or in vivo) can be any of the starting cells described herein. For example, the cell can be a non-neuronal cell and/or a differentiated cell.

In some embodiments, the therapeutic compositions are administered in a "therapeutically effective amount." Such a therapeutically effective amount is an amount sufficient to obtain the desired physiological effect, e.g., treatment of a condition, disorder, disease and the like or reduction in symptoms of the condition, disorder, disease and the like. For example, the therapeutic agents can be administered to treat a condition, disorder, or disease such Alzheimer's disease, Parkinson's disease, amyotrophic lateral sclerosis (ALS; Lou Gehrig's disease), multiple sclerosis, hereditary spastic paraplegia (HSP), primary lateral sclerosis, Huntington's disease, progressive pseudobulbar palsy, progressive muscular atrophy, progressive bulbar palsy, post-polio syndrome, stroke, head trauma, spinal cord injury, and the like.

To achieve the desired effect(s), the composition can be formulated in single or divided dosages. For example, at least one BMP type 1 receptor ALK2/3 inhibitor, at least one TGF-beta inhibitor, at least one WNT inhibitor, at least one neuronal differentiation enhancer, at least one SMO agonist, at least one retinoic acid receptor γ agonist, at least one DNA methyltransferase inhibitor, at least one histone demethylase inhibitor, and/or at least one autophagy regulator can be present in the composition in amounts specified above or in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to the combination of compounds chosen for administration, the disease, the weight, the physical condition, the health, and the age of the mammal. Such factors can be readily determined by the clinician employing animal models or other test systems that are available in the art.

Reprogrammed cells can be included in the compositions in varying amounts depending upon the disease or injury to be treated. For example, the compositions can be prepared in liquid form for local or systemic administration containing about $10^3$ to about $10^{12}$ reprogrammed cells, or about $10^4$ to about $10^{10}$ reprogrammed cells, or about $10^5$ to about $10^8$ reprogrammed cells. One or more of the following types of compounds can also be present in the composition with the cells: at least one BMP type I receptor ALK2/3 inhibitor, at least one TGF-beta inhibitor, at least one WNT inhibitor, at least one neuronal differentiation enhancer, at least one SMO agonist, at least one retinoic acid receptor γ agonist, at least one DNA methyltransferase inhibitor, at least one histone demethylase inhibitor, and/or at least one autophagy regulator.

Administration of the composition, or contacting cell(s) with the composition may be in a single dose, in multiple doses, in a continuous or intermittent manner, depending, for example, upon the recipient's physiological condition, whether the purpose of the administration is in response to traumatic injury or for more sustained therapeutic purposes, and other factors known to skilled practitioners. The administration or contacting of the compounds and compositions of the invention may be essentially continuous over a preselected period of time or may be in a series of spaced doses. Both local and systemic administration is contemplated.

To prepare the composition, the compounds are synthesized and/or the cells are generated, and the components are purified as necessary or desired. The compounds, cells, and/or other agents can be suspended in a pharmaceutically acceptable carrier. If the composition contains only compounds, without cells, the composition can be lyophilized. These compounds and cells can be adjusted to an appropriate concentration, and optionally combined with other agents. The absolute weight of a given compound and/or other agent included in a unit dose can vary widely. For example, about 0.01 to about 2 g, or about 0.1 to about 500 mg, of at least one compound can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the compounds can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

It will be appreciated that the amount of compounds and cells for use in treatment will vary not only with the particular carrier selected but also with the route of administration, the nature of the condition being treated and the age and condition of the patient. Ultimately, the attendant health care provider may determine proper dosage. A pharmaceutical composition may be formulated with the appropriate ratio of each compound in a single unit dosage form for administration with or without cells. Cells can be separately provided and either mixed with a liquid solution of the compound composition, or administered separately.

The compounds can also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

One or more suitable unit dosage forms containing the compounds and/or the reprogrammed cells can be administered by a variety of routes including parenteral (including subcutaneous, intravenous, intramuscular and intraperitoneal), intracranial, intraspinal, oral, rectal, dermal, transdermal, intrathoracic, intrapulmonary and intranasal (respiratory) routes.

The compositions of the invention may be prepared in many forms that include aqueous solutions, suspensions, tablets, hard or soft gelatin capsules, and liposomes and other slow-release formulations, such as shaped polymeric gels. However, administration of cells often involves parenteral or local administration in an aqueous solution. Similarly, compositions containing cells and/or compounds can be administered in a device, scaffold, or as a sustained release formulation.

Thus while compositions containing only compounds can be administered in an oral dosage form, compositions containing cells are administered locally or systemically as non-oral formulations. When compositions contain only compounds, those compositions can be formulated as an oral dosage form so that the compounds are released into the stomach for quick absorption or in the intestine after passing through the stomach. Different types of formulating procedures are described in U.S. Pat. No. 6,306,434 and in the references contained therein.

Liquid pharmaceutical compositions may be in the form of, for example, aqueous or oily suspensions, solutions, emulsions, syrups or elixirs, dry powders for constitution with water or other suitable vehicles before use. Such liquid pharmaceutical compositions may contain conventional additives such as suspending agents, emulsifying agents, non-aqueous vehicles (which may include edible oils), or preservatives.

Compounds and/or cells can be formulated for parenteral administration (e.g., by injection, for example, bolus injection or continuous infusion) and may be presented in unit dosage form in ampoules, prefilled syringes, small volume infusion containers or multi-dose containers with an added preservative. The pharmaceutical compositions can take the form of suspensions, solutions, or emulsions in oily or aqueous vehicles, and can contain formulatory agents such as suspending, stabilizing and/or dispersing agents. Suitable carriers include saline solution, phosphate buffered saline, and other materials commonly used in the art.

The compositions can also contain other ingredients such as agents useful for treatment of neuronal diseases and injuries, such as, for example, riluzole, ceftriaxone, lithium, xaliproden, pioglitazone, pyridostigmine, seligiline, RNA interference (RNAi) nucleic acids for reducing ALS susceptibility, Alzheimer's symptoms, or for reducing expression of mutated genes (e.g., RNAi of mutant SOD1 genes, or RNAi for any of the mutant NFH, dynactin, vesicular binding protein or ALSIN genes), neurotrophic factors (e.g., IGF-1, EPO, CTNF, BDNF, VEGF), anti-oxidative agents such as HIF-1α, amino acids, creatine, and other agents or stem cells, e.g., for the treatment of motor neuron diseases. Additional agents can also be included such as antibacterial agents, antimicrobial agents, anti-viral agents, biological response modifiers, growth factors; immune modulators, monoclonal antibodies and/or preservatives. The compositions of the invention may also be used in conjunction with other forms of therapy.

Supplementary factors can be included in the compositions and/or in a cell culture media containing any of the compositions, compounds or agents described herein. Examples of such supplementary factors include bone morphogenic protein (BMP)-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, brain derived neurotrophic factor, ciliary neutrophic factor, cytokine-induced neutrophil chemotactic factor 1, cytokine-induced neutrophil chemotactic factor 2α, cytokine-induced neutrophil chemotactic factor 2β, β endothelial cell growth factor, endothelin 1, epidermal growth factor, epithelial-derived neutrophil attractant, fibroblast growth factor (FGF) 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor (acidic), fibroblast growth factor (basic), growth related protein, growth related protein α, growth related protein β, growth related protein γ, heparin binding epidermal growth factor, hepatocyte growth factor, insulin-like growth factor I, insulin-like growth factor II, insulin-like growth factor binding protein, keratinocyte growth factor, leukemia inhibitory factor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, pre-B cell growth stimulating factor, stem cell factor, transforming growth factor a, transforming growth factor β, transforming growth factor β1, transforming growth factor 01.2, transforming growth factor 132, transforming growth factor β3, latent transforming growth factor β1, transforming growth factor β binding protein I, transforming growth factor β binding protein II, transforming growth factor β binding protein III, and vascular endothelial growth factor.

Exemplary cytokines can be included such as interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN), IFN-γ, tumor necrosis factor (TNF), TNF1, TNF2, TNF-α, macrophage colony stimulating factor (M-CSF), granulocyte-monocyte colony stimulating factor (GM-CSF), granulocyte colony stimulating factor (G-CSF), megakaryocyte colony stimulating factor (Meg-CSF)-thrombopoietin, stem cell factor, and erythropoietin. Chemokines can also be included such as IP-10 and Stromal Cell-Derived Factor 1α.

Exemplary hormones contemplated for inclusion in the compositions and/or cell culture media described herein can include, but are not limited to, steroid hormones and peptide hormones, such as insulin, somatostatin, growth hormone, hydrocortisone, dexamethasone, 3,3',5-Triiodo-L-thyronine, and L-Thyroxine.

Kits

A variety of kits are described herein that include any of the compositions, compounds and/or agents described herein. The compounds and/or agents described herein can be packaged separately into discrete vials, bottles or other containers. Alternatively, any of the compounds and/or agents described herein can be packaged together as a single composition, or as two or more compositions that can be used together or separately. The compounds and/or agents described herein can be packaged in appropriate ratios and/or amounts to facilitate conversion of selected cells across differentiation boundaries to form neuronal cells.

A kit is described herein for culture of cells in vitro that can include any of the compositions, compounds and/or agents described herein, as well as instructions for using those compositions, compounds and/or agents. Some kits can include a cell culture medium or a variety of cell culture media that includes any of the compositions, compounds and/or agents described herein. The kits can include one or more sterile cell collection devices such as a swab, skin scrapping device, a needle, a syringe, and/or a scalpel. The kits can also include antibodies for detection of neuronal cell markers such as antibodies against Sox2, Pax6, Tuj1, Tau, NeuN, MAP2, Ascl1, Olig2, Synapsin, or any combination thereof. The antibodies can be labeled so that a detectable signal can be observed when the antibodies form a complex with the neuronal cell marker(s).

The instructions can include guidance for culturing cells for a time and under conditions sufficient to convert a selected cell across differentiation boundaries and into the neuronal lineage. For example, the instructions can describe amounts of the compositions, compounds and/or agents described herein to add to cell culture media, times sufficient to convert cells to the neuronal lineage, maintenance of appropriate cell densities for optimal conversion, and the like. For example, the instructions can describe procedures for rehydration or dilution of the compositions, compounds and/or agents described herein. When a kit provides a cell culture medium containing some of the compositions, compounds and/or agents described herein, the instructions can describe how to add other compounds and/agents. The instructions can also describe how to convert the selected cells to neuronal progenitor cells or to mature neuronal cells.

The instructions can also describe procedures for detecting neuronal cell markers by use of the antibodies against those markers so that the extent of conversion and/or differentiation can be assessed.

Another kit is also described herein that includes any of the compositions, compounds and/or agents described herein for therapeutic treatment of a subject. For example, the kit can include the M9 cocktail. The kit can include any of the compositions, compounds and/or agents described herein, as well as instructions for administering those compositions, compounds and/or agents. Such instructions can provide the information described throughout this application. The kit can also include cells. For example, the kit can include chemically induced neuronal cells that have been treated by the methods described herein and that are ready for administration.

The cells, compositions and/or compounds can be provided within any of the kits in a delivery device. Alternatively a delivery device can be separately included in the kit(s), and the instructions can describe how to assemble the delivery device prior to administration to a subject. The delivery device can provide a scaffold for cell growth and/or a matrix for controlled release of any of the compositions, compounds or agents described herein.

Any of the kits can also include syringes, catheters, scalpels, sterile containers for sample or cell collection, diluents, pharmaceutically acceptable carriers, and the like.

The kits can provide other factors such as any of the supplementary factors described herein for the compositions in the preceding section.

Definitions

As used herein, the term "neuronal cell" refers to a cell of a neuronal lineage. Examples of neuronal cells include, but are not limited to, neurons, astrocytes, oligodendrocytes, and neural precursor cells.

As used herein, the term "mature neuron" refers to a differentiated neuron. In some embodiments, a neuron is said to be a mature neuron if it expresses one or more markers of mature neurons, e.g., microtubule-associated protein 2 (MAP2) and Neuronal Nuclei (NeuN).

As used herein, the term "functional neuron" refers to a differentiated neuron that is able to send or receive electrical signals. In some embodiments, a neuron is said to be a functional neuron if it exhibits electrophysiological properties (e.g., if the neuron produces excitatory postsynaptic currents, which are indicative of functional synapses, and/or produces whole-cell currents and/or neurotransmitter receptor-mediated currents) and/or if it expresses one or more markers of functional neurons, e.g., Synapsin, vesicular GABA transporter (VGAT), vesicular glutamate transporter (VGLUT), and gamma-aminobutyric acid (GABA).

As used herein, a "differentiated non-neuronal cell" may refer to a cell that is not able to differentiate into all cell types of an adult organism (i.e., is not a pluripotent cell), and which is of a cellular lineage other than a neuronal lineage (e.g., a hematopoietic lineage or a connective tissue lineage). Differentiated cells include, but are not limited to, multipotent cells, oligopotent cells, unipotent cells, progenitor cells, and terminally differentiated cells. In particular embodiments, a less potent cell is considered "differentiated" in reference to a more potent cell.

As used herein, a cell that differentiates into a mesodermal, ectodermal or endodermal lineage defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, that give rise to the lining of the intestine, and cells that give rise to pancreogenic and splanchogenic cells.

A "somatic cell" is a cell forming the body of an organism. Somatic cells include cells making up organs, skin, blood, bones and connective tissue in an organism, but not germ cells.

Cells can be from, e.g., human or non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human, an adult human, or non-human mammal.

As used herein, the term "totipotent" means the ability of a cell to form all cell lineages of an organism. For example, in mammals, only the zygote and the first cleavage stage blastomeres are totipotent.

As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm.

As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

As used herein, the term "oligopotent" refers to the ability of an adult stem cell to differentiate into only a few different cell types. For example, lymphoid or myeloid stem cells are capable of forming cells of either the lymphoid or myeloid lineages, respectively.

As used herein, the term "unipotent" means the ability of a cell to form a single cell type. For example, spermatogonial stem cells are only capable of forming sperm cells.

As used herein, the term "direct reprogramming" or "transdifferentiation" refers to the generation of a cell of a certain lineage (e.g., a neuronal cell) from a different type of cell (e.g., a fibroblast cell) without an intermediate process of de-differentiating the cell into a cell exhibiting pluripotent stem cell characteristics.

As used herein, the terms "subject" or "patient" refers to any animal, such as a domesticated animal, a zoo animal, or a human. The "subject" or "patient" can be a mammal like a dog, cat, bird, livestock, zoo animal, endangered species animal, or a human. Specific examples of "subjects" and "patients" include, but are not limited to, individuals with a neuronal disease or disorder, and individuals with neuronal disorder-related characteristics or symptoms.

As used herein, the term "neuronal disorder" or a "neuron disorder" refers to disorders of the nerves of the brain, spinal cord, or peripheral nervous system, including, but not limited to neurodegenerative/neurological disorders such as progressive deterioration of the nerves in the spinal cord and/or brain. Examples of neuron disorders include, but are not limited to, Alzheimer's disease, Parkinson's disease, amyotrophic lateral sclerosis (ALS; Lou Gehrig's disease), multiple sclerosis, hereditary spastic paraplegia (HSP), primary lateral sclerosis, Huntington's disease, progressive pseudobulbar palsy, progressive muscular atrophy, progressive bulbar palsy, post-polio syndrome, stroke, head trauma, spinal cord injury, and the like.

As used herein, the phrase "symptoms of neuron disorder" and "characteristics of neuron disorder" include, but are not limited to, lower extremity weakness, bladder disturbance, impaired position sense in the legs, and neurologic deficits, such as a decrease in the function of the brain, spinal cord, muscles, and/or nerves, for example, inability to speak, decreased sensation, loss of balance, weakness, cognitive dysfunction, visual changes, abnormal reflexes, and problems walking.

The following non-limiting Examples illustrate some of the experimental work involved in developing the invention.

Example 1: Materials and Methods

This Example describes some of the materials and methods employed in the devilment of the invention.

Mouse Cell Lines

Procedures involving mice were approved by the Institutional Animal Care and Use Committee at the University of California, San Francisco. Homozygous Tau-EGFP knock-in mice were purchased from the 6 Jackson Laboratory (Mapt$^{tm1(EGFP)klt}$/, stock number 004779); Fsp1-Cre mice were from the Jackson Laboratory (BALB/c-Tg (S100α4-cre) 1Egn/YunkJ) and were kindly provided by Dr. Deepak Srivastava at the Gladstone Institute of Cardiovascular Disease; ROSA26-tdTomato mice were from the Jackson Laboratory (Gt(ROSA)26Sortm14(CAG-tdTomato)Hze) and were kindly provided by Dr. Ken Nakamura at Gladstone Institute of Neurological Disease.

The chimera mouse embryos with Nanog-GFP were generated as described by Wernig et al. (*Nat Biotechnol* 26: 916-924 (2008)), with some modification. In brief the NGFP iPSCs cells were injected into blastocyst and transferred into recipient CD1 females. The genotype of all mouse lines was validated before breeding. The Tau-GFP mice were maintained as a homozygous line. The Fsp1-Cre/ROSA26$^{dtTomato}$ mice were obtained by crossing Fsp 1-Cre mice with ROASA26-tdTomato mice Mouse Embryonic Fibroblasts and Tail-Tip Fibroblasts Preparations Mouse embryonic fibroblasts (MEF) and mouse tail-tip fibroblast (TTF) preparations were obtained using methods similar to those described by Kim et al. (*Proc Natl Acad Sci USA* 108: 7838-7843 (2011)), with some modifications. Briefly, the mouse embryonic fibroblasts and mouse tail-tip fibroblasts of the desired genotype were obtained from E13.5 mouse embryos, or from 3-week postnatal mouse tail-tip tissues, respectively. To obtain fibroblasts, the E13.5 embryos or tail-tip tissues were sliced into small pieces, these small pieces were trypsinized, and the cells were plated in MEF medium. All fibroblasts were expanded for two passages before being used for experiments. To prepare the tdMEF or tdTTF, the resulting fibroblasts were sorted for tdTomato+/p75− by FACS.

Cell Culture Medium

All fibroblasts were cultured in MEF medium (Dulbecco's modified Eagle's medium supplemented with 10% fetal bovine serum, 0.1 mM nonessential amino acids, and 2 mM Glutamax) at 37° C. Medium was refreshed every other day. All neural stem cells, including primary neural stem cells and chemical-induced neural stem cells, were cultured in neural stem cell medium (NSC medium, 50% Neural basal, 50% DMEM/F12/Glutamax, 1×N2, 1×B27 without vitamin A, 0.075% BSA, 0.1 mM nonessential amino acids, 20 ng/ml bFGF, 20 ng/ml EGF). Medium was refreshed daily.

Chemical Conversion of Fibroblasts to ciNSLCs

To convert the fibroblasts into ciNSLCs, MEFs were seeded into Matrigel (Corning, 1:40 dilution)-coated 24-well plates at 15,000 per well, or 1-1.5 million in 15-cm dishes in MEF medium (Dulbecco's modified Eagle's medium supplemented with 10% FBS, 0.1 mM nonessential amino acids, and 2 mM Glutamax) for the first 24 hours. MEF cells were washed twice with 1×PBS before being cultured into medium containing the M9 mixture of compounds (50% Neural basal, 50% DMEM/F12/Glutamax, 1×N2, 1×B27 without vitamin A, 0.075% BSA, 0.1 mM nonessential amino acids, where the M9 mixture was: CHIR99021 at 3 μM, LDN193189 at 100 nM, A83-01 at 0.5 μM, Hh-Ag1.5 at 0.5 μM, retinoic acid at 1 μM, SMER28 at 10 μM, RG108 at 10 μM, Parnate 2 μM, bFGF 10 ng/ml) at 5% $O_2$ and 5% $CO_2$ incubator at 37° C. M9 medium was refreshed every other day. After a 10-day induction, cells were cultured in neural stem cells medium (NSC medium). Afterwards, the cells could be repeatedly propagated in NSC medium.

Immunocytochemistry

Cells were washed once with 1×PBS and fixed with 4% paraformaldehyde at room temperature for 10 minutes, followed by permeabilization with 0.2% Triton X-100 in 1×PBS for 10 min, and blocking with 7.5% BSA for at least 1 hour. All primary antibodies were diluted in 1×PBS with 7.5% BSA, and the incubation was performed at 4° C. overnight. The cells were washed with 1×PBS five times for 10 min each at room temperature. The secondary antibodies, labeled with Alexa-488, Alexa-555, and Alexa-647, were purchased from Invitrogen, and were diluted into 1×PBS with 7.5% BSA. Incubation with the secondary antibodies was for 1 hour at room temperature, followed by five 10-minute washes with 1×PBS. The nuclei were stained with DAPI. Living cell staining was used for cell-surface marker O4, as described by Najm et al. (*Nat. Biotechnol.* 31: 426-433 (2013)). Antibodies used in this study are listed below in Table 1.

TABLE 1

Antibodies Employed for Detecting Cells and Gene Expression

| Antigen | Antibody Type | Company | Cat No. |
|---|---|---|---|
| Tuj1 | mouse mAb | Covance | MMS-435P |
| MAP2 | rabbit | Millipore | AB5622 |
| Nestin | mouse IgG2a | R&D | MAB2736 |
| GFAP | rabbit | Dako | z0334 |
| Synapsin 1 | rabbit anti-serum | Millipore | AB1543 |
| N-Cad | mouse IgG1 | BD | 610920 |
| NeuN | mouse | Millipore | MAB377 |
| Olig2 | rabbit | Millipore | AB9610 |
| GABA | rabbit | Sigma | A2052 |
| vGluT1 | rabbit polyclonal | Synaptic Systems | 135 303 |
| Sox2 | rabbit | Stemgent | 09-0024 |
| O4 | mouse mAb | R&D | MAB1326 |
| NG2 | Rabbit | Millipore | AB5320 |

TABLE 1-continued

Antibodies Employed for Detecting Cells and Gene Expression

| Antigen | Antibody Type | Company | Cat No. |
|---|---|---|---|
| a-p75 NGF receptor FITC | mouse IgG2a | Abcam | ab62122-100ug |
| mouse IgG2a isotype control FITC | mouse IgG2a | Abcam | ab81197 |
| Pax6 | Rabbit | Covance | PRB-278P |
| H3K27ac | mouse IgG1 | Millipore | 17-683 |
| H3K27me3 | Rabbit polyclonal serum | Millipore | 17-622 |
| H3K4me3 | rabbit monoclonal purified IgG | Millipore | 17-614 |
| H3K4me1 | rabbit polyclone | Abcam | ab8895 |
| Gli2 | Rabbit | Abcam | ab167389 |
| Elk1 | rabbit monoclonal | Epitomics | 1277-1 |
| BrdU | mouse IgG1, k | BD | 347583 |

Alkaline Phosphatase Activity Assay

Alkaline phosphatase activity was evaluated according to the Alkaline Phosphatase Detection Kit (Sigma).

Neural Differentiation

Approximately 5000 ciNSLCs were seeded onto the laminine/poly-orthinine-coated glass cover slips in 24-well plates containing NSC medium for first 24 hours. After 24 hours, for neuron differentiation, the medium was switched to neuron differentiation medium (NSC medium without bFGF and EGF, with addition of 200 μM ascorbic acid, 2 μM db-cAMP, 25 ng/ml BDNF, 25 ng/ml NT3 and 50 ng/ml GDNF). Half of the medium was changed every 2 days. Specific neuron markers were analyzed by day 10 to day 20 after differentiation using methods described by 2, 4-6 Kim et al. (*Proc Natl Acad Sci USA* 108: 7838-7843 (2011)); Ring et al. (*Cell Stem Cell* 11, 100-109 (2012)); Zhu et al. (*Cell Res* 24: 126-129 (2014)); and Li et al (*Proc Natl Acad Sci USA* 108: 8299-8304 (2011)). To differentiate the cells into oligodendrocytes, the differentiation medium contained 10 ng/ml PDGF-AA, 10 ng/ml bFGF, 10 ng/nl SHE, and 40 ng/ml T3, and the cells were cultured for 8-12 days (Najm et al., *Nat. Biotechnol,* 31: 426-433 (2013)). To differentiate the cells into astrocytes, BMP4 (50 ng/ml) was applied into differentiation medium for 8-12 days (Kim et al., *Proc Natl Acad Sci USA* 108: 7838-7843 (2011); Najm et al., *Nat. Biotechnol.* 31: 426-433 (2013); Ring et al., *Cell Stem Cell* 11, 100-109 (2012); Zhu et al., *Cell Res* 24: 126-129 (2014)).

Neurosphere Culture

Monolayer cultured ciNSLCs were trypsinized to generate single cells and incubated at a density of 10,000 cells per ml in neural stem cell medium. Cells were cultured within ultralow attachment 6-well plates. The medium was changed every day by spinning down the cells at 1,000 rpm for 5 min and re-suspending the cells into fresh neural stem cell medium (Ring et al., *Cell Stem Cell* 11, 100-109 (2012)).

Electrophysiological Analysis

Whole-cell patch-clamp recordings were taken from ciNSLC-derived neurons 10-20 days after co-culturing with rat cortical neurons on differentiation condition. Cultured neurons were transferred to a perfusion stage on an Olympus BX51W1 upright microscope and perfused at 2.5 ml min$^{-1}$ at room temperature with artificial cerebral spinal fluid (aCSF) containing (in mM): NaCl at 119 mM, KCl at 2.5 mM, $NaH_2PO_4$ at 1 mM, $NaHCO_3$ at 26.2 mM, glucose at 11 mM, $CaCl_2$ at 2.5 mM, and $MgSO_4$ at 1.3 mM, with the osmolality adjusted to 300 osm L$^{-1}$. The artificial cerebral spinal fluid was bubbled with 95% $O_2$ and 5% $CO_2$ throughout the recordings. Data were gathered through a Multi-Clamp 700B amplifier (Axon Instruments), filtered at 2 kHz, and digitized at 10 kHz. Offline analysis was carried out in Igor Pro (Wavemetrics). Action potentials were recorded under the current-clamp whole-cell configuration. The pipette solution for current-clamp experiments contained (in mM): K-gluconate at 123 mM, KCl at 10 mM, $MgCl_2$ at 1 mM, HEPES at 10 mM, EGTA at 1 mM, $CaCl_2$ at 0.1 mM, $K_2ATP$ at 1 mM, $Na_4GTP$ at 0.2 mM, and glucose at 4 mM, with the pH adjusted to 7.2 using KOH. Membrane potential was held around −70 mV and step currents of −20 to 50 pA were introduced at 10-pA intervals. Whole-cell currents were recorded at a holding potential of −70 mV with voltage steps ranging from −70 mV to +30 mV that were delivered at 20-mV increments. Spontaneous postsynaptic currents were recorded in the whole-cell voltage-clamp mode. The whole-cell pipette solution for synaptic current recordings contained (in mM): CsCl at 135 mM, HEPES at 10 mM, EGTA at 1 mM, Mg-ATP at 4 mM, $Na_4GTP$ at 0.4 mM, and QX-314 at 10 mM, pH 7.4. To sample the excitatory and inhibitory current, 1 mM glutamate and 100 μM GABA were puffed under 10 p.s.i. for 100 ms, and the holding voltages were −70 41 mV and 0 mV, respectively.

RNA Preparation and PCR

Total RNA was extracted using RNeasy Plus mini kit (Qiagen). Reverse transcription and PCR were performed as described by Zhang et al., *Nat Struct Mol Bio* 17, 202-209 (2010)). In brief, 1 μg total RNA was used for reverse transcription reaction employing an iScript cDNA synthesis kit (Bio-Rad), and the resulting cDNA was diluted five times in $H_2O$ for PCR. For the semi-quantitative PCR, 1 μl of 1/5 diluted cDNA was used as template for PCR program: 95° C. for 5 min, and 35 cycles of 95° C. for 30 seconds, 60° C. for 30 seconds, and 72° C. for 30 seconds, followed by 72° C. for 10 min. Quantitative PCR was performed following the protocol of FAST SYBR Green Master Mix (ABI). All PCR was performed in triplicate, and the expression of individual genes was normalized to that of Gapdh. The primer sequences employed are listed in Table 2.

TABLE 2

Quantitative PCR Primers

| Gene | Primer type | Sequence | SEQ ID NO: |
|---|---|---|---|
| Oct4 | forward primer | ACATCGCCAATCAGCTTGG | 3 |
|  | reverse primer | AGAACCATACTCGAACCACATCC | 4 |
| Nanog | forward primer | CCTCCAGCAGATGCAAGAACTC | 5 |
|  | reverse primer | CTTCAACCACTGGTTTTTCTGCC | 6 |
| Gapdh | forward primer | CATGGCCTTCCGTGTTCCTA | 7 |
|  | reverse primer | GCCTGCTTCACCACCTTCTT | 8 |
| Sox2 | forward primer | GAACGCCTTCATGGTATGGT | 9 |
|  | reverse primer | TTGCTGATCTCCGAGTTGTG | 10 |
| Sox1 | forward primer | GGCCGAGTGGAAGGTCATGT | 11 |
|  | reverse primer | TCCGGGTGTTCCTTCATGTG | 12 |
| Gfap | forward primer | CGGAGACGCATCACCTCTG | 13 |
|  | reverse primer | AGGGAGTGGAGGAGTCATTCG | 14 |
| Olig2 | forward primer | GGCGGTGGCTTCAAGTCATC | 15 |
|  | reverse primer | TAGTTTCGCGCCAGCAGCAG | 16 |
| Hes5 | forward primer | AGTCCCAAGGAGAAAACCGA | 17 |
|  | reverse primer | GCTGTGTTTCAGGTAGCTGAC | 18 |

TABLE 2-continued

Quantitative PCR Primers

| Gene | Primer type | Sequence | SEQ ID NO: |
|---|---|---|---|
| Aash1 | forward primer | AGGGATCCTACGACCCTCTTA | 19 |
|  | reverse primer | ACCAGTTGGTAAAGTCCAGCAG | 20 |
| Sox3 | forward primer | CACAACTCCGAGATCAGCAA | 21 |
|  | reverse primer | TCCGGGTACTCCTTCATGTG | 22 |
| Zic2 | forward primer | AGTGTGAGTTCGAGGGCTGT | 23 |
|  | reverse primer | GGGATGCGTGTAGGACTTGT | 24 |
| Oct6 | forward primer | TCGAGGTGGGTGTCAAAGG | 25 |
|  | reverse primer | GGCGCATAAACGTCGTCCA | 26 |
| Pax6 | forward primer | AGGGGGAGAGAACACCAACT | 27 |
|  | reverse primer | CATTTGGCCCTTCGATTAGA | 28 |
| Elk1 | forward primer | AGGGTTGTGCAAAGCAAGTG | 29 |
|  | reverse primer | TGGCTCACACAATCAGCTTC | 30 |
| Gli2 | forward primer | ATGCTGGTTGTTCACATGCG | 31 |
|  | reverse primer | AGGCATTGGAGAAGGCTTTG | 32 |

RNA-Seq Library Preparation

RNA-seq libraries were prepared with ovation RNA-seq system v2 kit (NuGEN). In this method, the total RNA (50 ng) is reverse-transcribed to synthesize the first-strand cDNA with a combination of random hexamers and a poly-T chimeric primer. The RNA template is then partially degraded by heating and the second-strand cDNA is synthesized using DNA polymerase. The double-stranded DNA is then amplified using single primer isothermal amplification (SPLA). SPIA is a linear cDNA amplification process in which RNase H degrades RNA in DNA/RNA heteroduplex at the 5'-end of the double-stranded DNA, after which the SPIA primer binds to the cDNA and the polymerase starts replication at the 3'-end of the primer by displacement of the existing forward strand. Random hexamers are then used to amplify the second-strand cDNA linearly. Finally, libraries from the SPIA amplified cDNA were made using an Ultralow V2 library kit (NuGEN). The RNA-seq libraries were analyzed by Bioanalyzer and quantified by QPCR (KAPA). Three RNA-seq libraries were pooled per lane of paired-end 100 bp sequencing on HiSeq 2500 instrument (Illumina).

RNA-Seq Data Processing

Trimming of known adapters and low quality regions of reads was performed using Fastq-mcf (see website at code-.google.com/p/ea-utils). Sample QC was assessed using FastQC (see website at www.bioinformatics.babraham.ac.uk/projects/fastqc/). Reads were aligned to the mouse reference assembly mm9 using Tophat 2.0.13 (Kim et al., *Genome Biology* 14 (2011)). Gene-level expression was tallied by SubreadfeatureCounts (Liao et al., *Bioinformatics* 30, 923-930 (2014)) using Ensembl's gene annotation for mm9. The differential expression P-values were calculated using edgeR (Robinson et al., *Bioinformatics* 26, 139-140 (2010)). The built-in R function "p.adjust" was used to calculate the FDR using Benjamini-Hochberg method (Benjamini, & Hochberg, *Journal of the Royal Statistical Society Series* B 57: 289-300 (1995)). Gene ontology analyses were completed through DAVID Bioinformatics Resources 6.7 or ToppGene.

Chromatin Immunoprecipitation

Chromatin immunoprecipitation was performed according to the instructions of an EZ-ChIP kit. In brief, 1-10 million cells were fixed with 1° 6 paraformaldehyde at room temperature for 10 min. The fixation reaction was then quenched by incubation in 0.125 M glycine for 5 min at room temperature. After twice washing with pre-chilled 1×PBS, the cells were suspended into 1 ml of chilled nuclei buffer (5 mM PIPES (pH 8), 85 mM KCl, 1% NP-40, with freshly added Protease Inhibitor Cocktail II, Millipore Cat #20-283). Cell nuclei were released by homogenizing the tissue in a Dounce Homogenizer (Wheaton, 1 ml, tight, Cat #357538) for 20 strokes and centrifugation at 430 rcf for 5 min. Nuclei were resuspended into cell lysis buffer (1% SDS, 10 mM EDTA and 50 mM Tris pH 8.1). The released chromatin was sheared by Covaris S2 sonicator into fragment sizes of about 200-500 bp. For each sample, 20 μl of solubilized chromatin was used as input DNA to normalize sequencing results and the remaining chromatin was precleaned with 50 μl Protein-G beads at 4° C. for 2 hours before being subjected to immunoprecipitation. For each chromatin immunoprecipitation, 2 μg of antibody against histone markers, or 5 μg of antibody against Elk 1 or Gli2, were used. The antibodies employed are listed in Table 1 above. Immunoprecipitation was performed at 4° C. overnight, and the antibody-chromatin complexes were pulled down with 50 μl Protein-G beads at 4° C. for 2 hours. After seven washes using (1) one wash with low salt buffer (0.1% SDS, 1% Triton X-100, 2 mM EDTA, 20 mM Tris-HCl, pH 8.1, 150 mM NaCl), (2) one wash with high salt buffer (0.1% SDS, 1% Triton X-100, 2 mM EDTA, 20 mM Tris-HCl, pH 8.1, 500 mM NaCl), (3) one wash with LiCl Immune Complex wash buffer (0.25 M LiCl, 1% IGEPAL CA630, 1% deoxycholic acid (sodium salt), 1 mM EDTA, 10 mM Tris, pH 8.1), (4) one wash with high salt buffer, (5) one wash with low salt buffer, and (6) two washes with TE buffer, the chromatin was eluted, reverse cross-linked at 65° C. overnight and subjected to RNase A/proteinase K treatment. The purified DNA fragments were used for quantitative PCR.

In Vivo Injection and Brain Sections

All handling of animals was according to animal policy in University of California, San Francisco. To study the survival and differentiation of ciNSLCs in vivo, ciNSLCs labeled with tdTomato were microinjected into the cortices of P4-P5 pups with a beveled micropipette and a Nanoject by Drummond on a stereotaxic frame. Two injections of about 20,000 cells per injection site were made in the right hemisphere between bregma and lambda at a 25° angle towards the midline to a depth of about 0.30 mm. The pups were anesthetized on ice and held stable in a head mold during the procedure. At 2, or 4 weeks post-transplantation, the mice were perfused with saline and 4% paraformaldehyde. The brains were fixed for 24-48 h, washed with PBS, cryopreserved in 30% sucrose, and sectioned using a sliding microtome into 30-μm coronal sections, and immunostained with the following primary antibodies: monoclonal mouse anti-NeuN (1:2000; Millipore MAB377), polyclonal rabbit anti-GFAP (1:500; Dako), and polyclonal rabbit anti-Olig2 (1:500; Millipore AB9610). Alexa-488 or -647 (1:1000; Life Technology) secondary antibodies were used for immunofluorescence. Sections were mounted in Prolong Gold antifade reagent with DAPI (Life Technology). Images were taken on Zeiss LSM 700 confocal laser scanning microscope.

FACS Cytometry

For the tdMEF or tdTTF preparation, the fibroblasts with desired genotype were culture in MEF medium until 80% confluence. The cells were washed with 1×PBS and detached by Accutase treatment at 37° C. for 5 min. After harvesting, the cells were passed through 70-pin filter, washed twice with and resuspended into pre-cold F ACS buffer (1×PBS, 1.5% FBS, 0.5% BSA), The cells were incubated with either FITC-conjugated p75 antibody (abeam) or isotype control (BD) with suggested concentrations on ice for 45 min, followed by six washes with FACS buffer. Cells were then resuspended into FACS buffer and sorted by BD FACSAris II.

Inhibitor Assay

When performing the reprogramming, small molecule inhibitors, including 0.5 μM PD0325901, 10 μM SP 600125, 5 μM SB203580, 5 μM LY294002, or 2 μM LDE 225, was added in the freshly made M9 culture medium. DMSO was used in basal medium as control. The medium was changed every 2 days, and the Sox2+/Nestin+ cells were analyzed by immunostaining by day 10 after treatment.

shRNA Knockdown Assay

The shRNA constructs targeting Elk1 or Gli2 were purchased from Origene (eat #TR500594 for mouse Elk1 shRNA constructs in retroviral untagged vector pRS, and TR517874 for mouse Gli2 shRNA constructs in retroviral untagged vector pRS). The virus was packed and collected according to manual. The tdMEFs treated with M9 were infected by the retrovirus at the indicated time points twice, and immunostaining was performed at day 10 after chemical treatment to analyze the Sox2+/Nestin+ cells by InCell Analyzer 2000, and quantified by In Cell Developer.

Overexpression of Elk1 and Gli2

The overexpression plasmid carrying Elk1 (addgene 27156) or Gli2 (addgene 37671) was purchased from Addgene. The plasmid was transfected into tdMEF cells with Neon transfection system (Invitrogen) at 1450 V, 20 ms, and two pulses.

Example 2: Defining Starting Fibroblasts Via Lineage Tracing

This Example describes how fibroblasts can be identified and traced using a genetic lineage tracing strategy.

Primary MEFs contain heterogeneous populations of non-fibroblast precursor cells. The origin/identity of the starting fibroblasts can unambiguously be defined using fibroblast-specific protein 1 (Fsp1, also known as S100α4), which have been validated as specific markers tor fibroblasts, and Fsp1-Cre, which has been used to lineage-trace fibroblast origin (Qian et al., Nature 485, 593-598 (2012)).

Figure 1B:
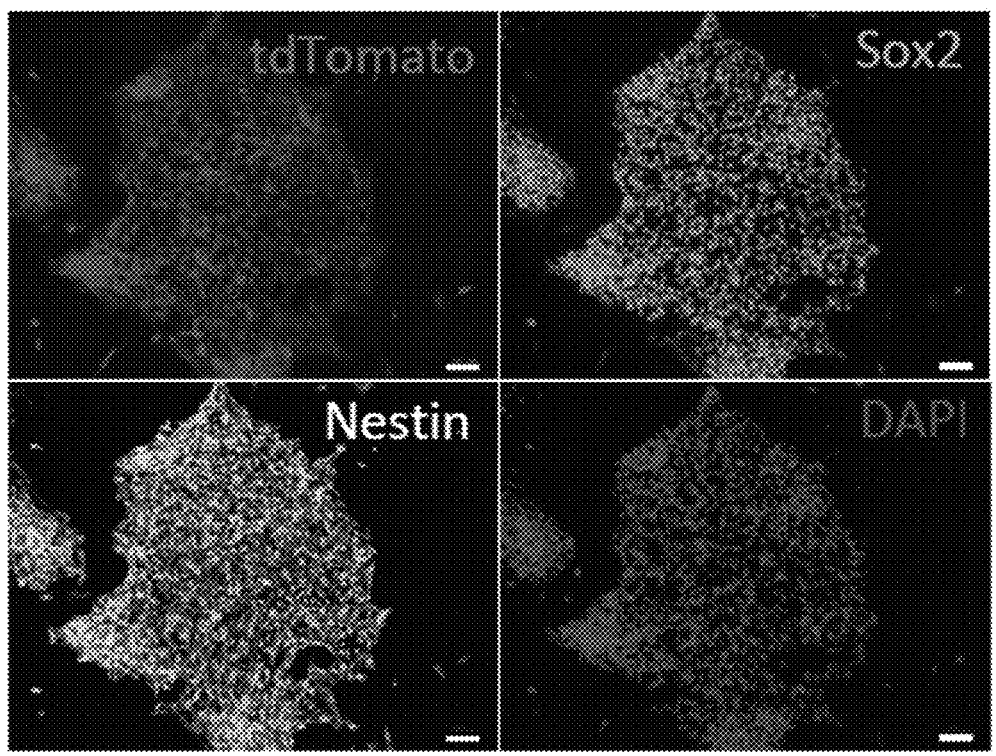
Figure 1C:
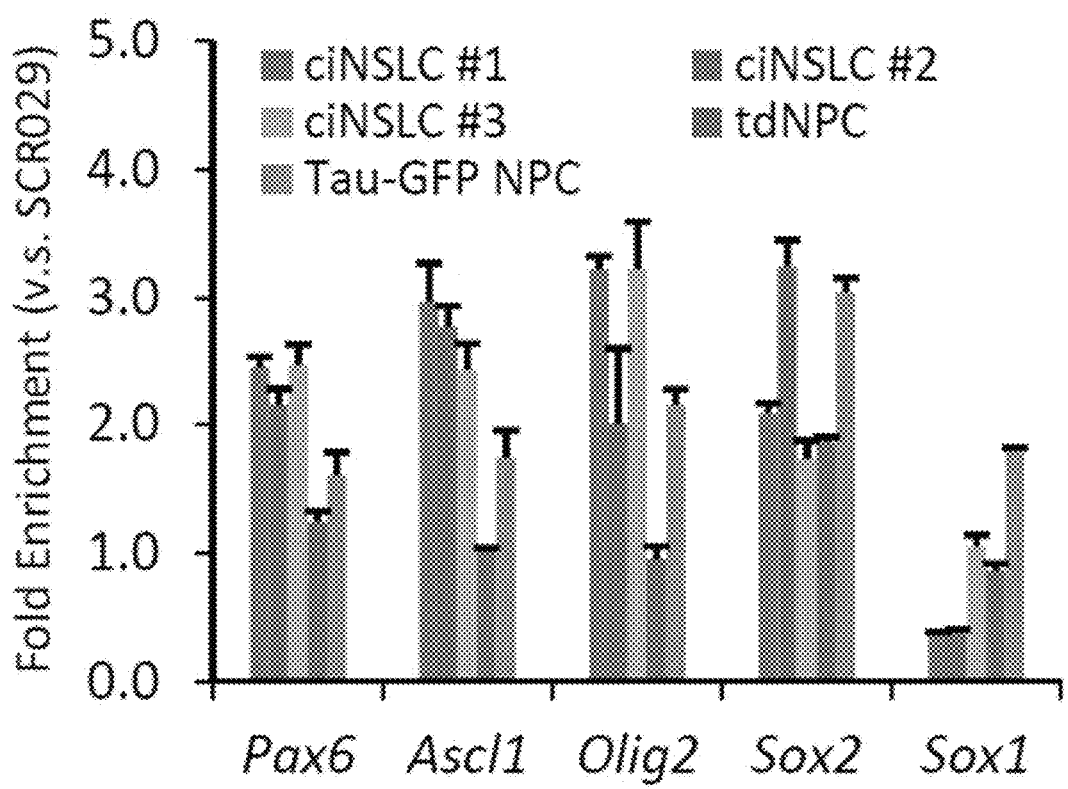
Figure 1D:
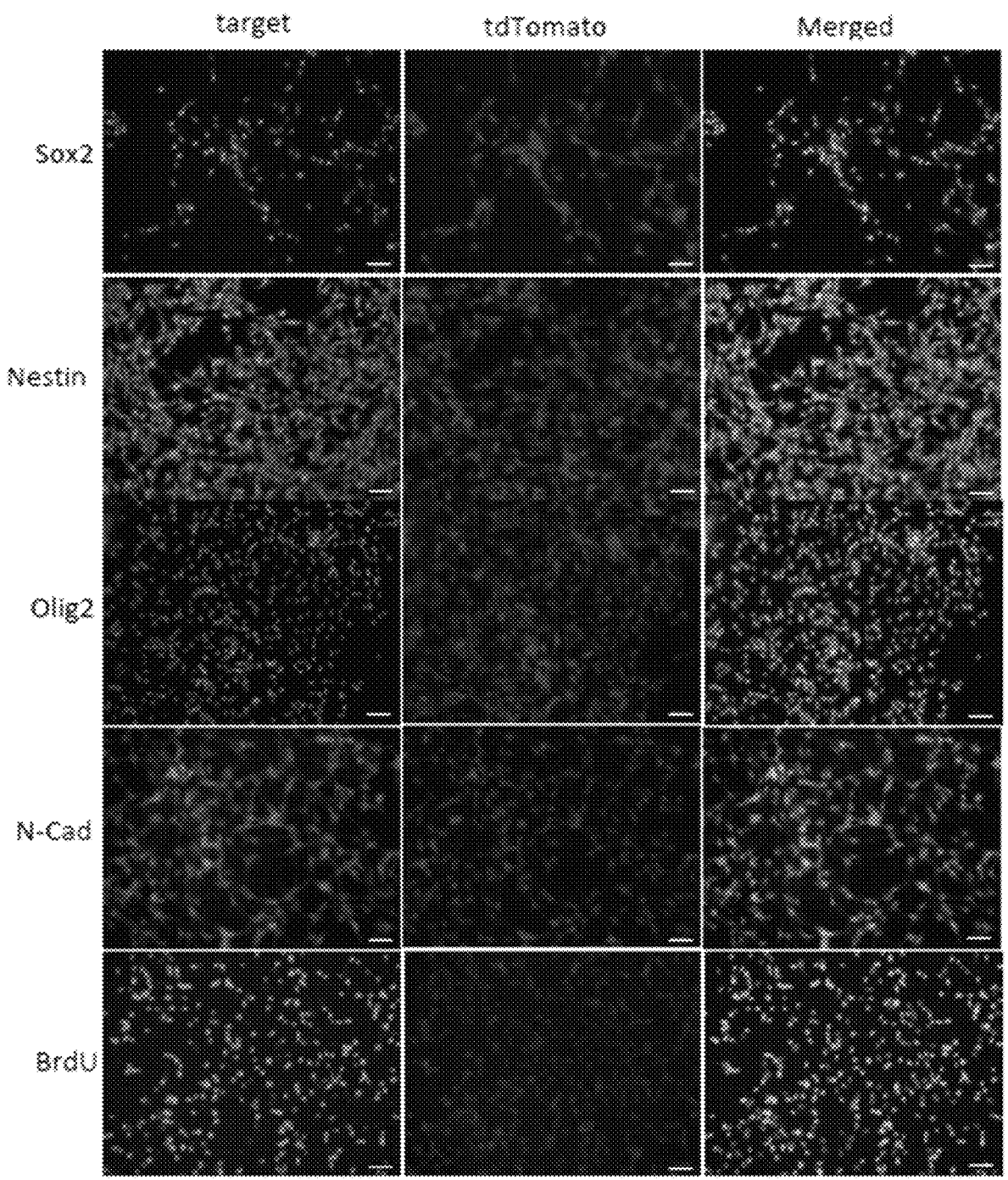
Figure 1E:
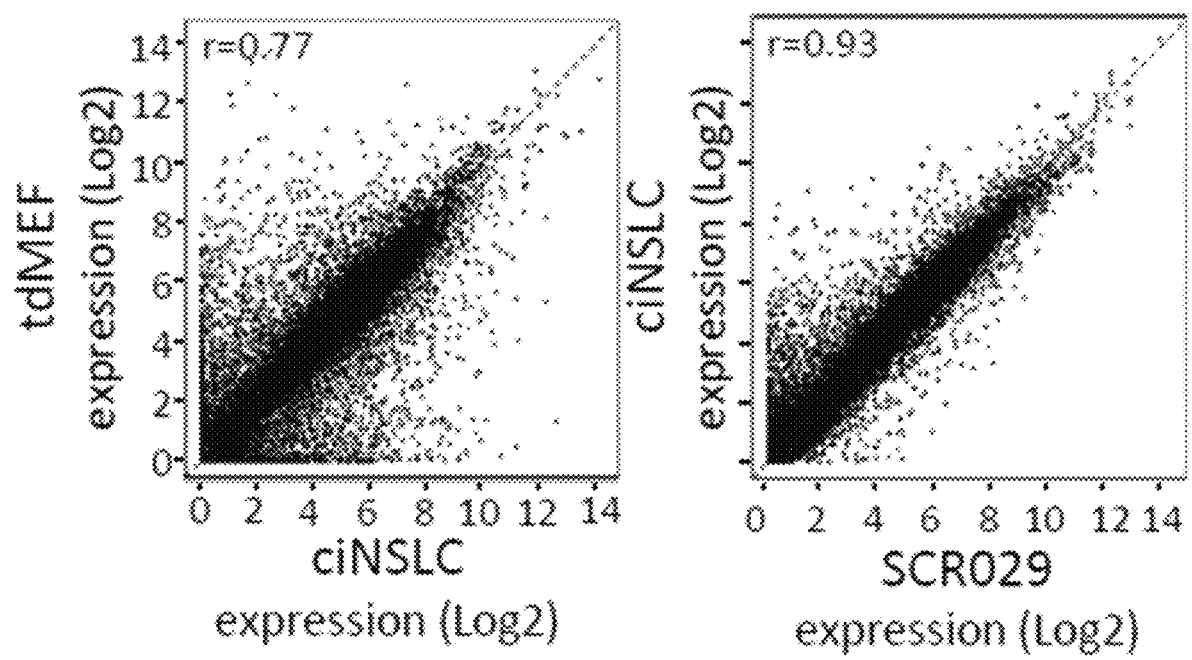
Figure 1F:
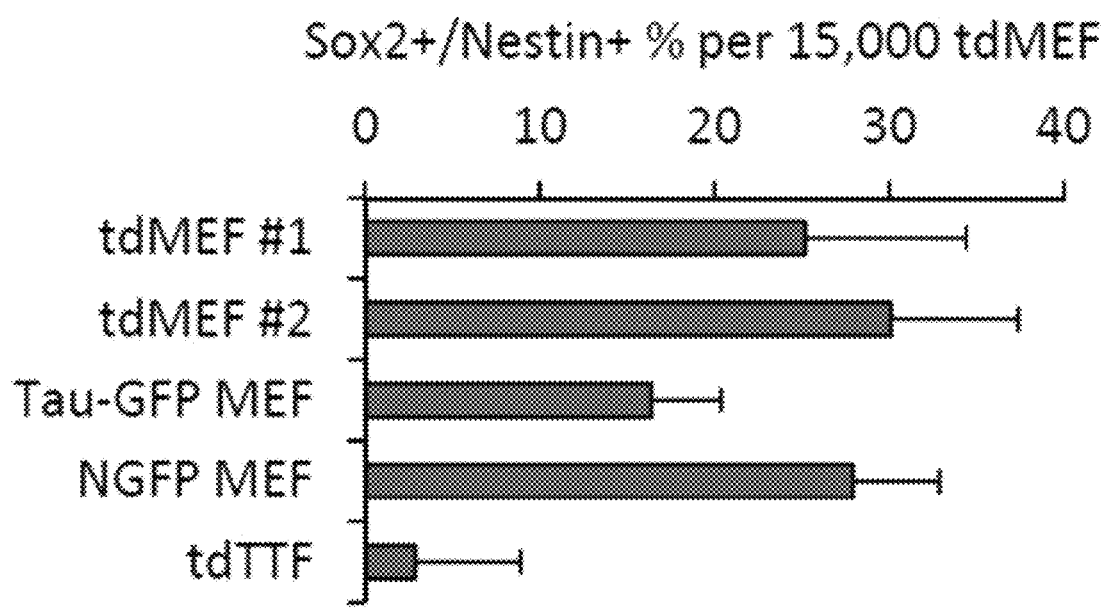
Figure 1G:
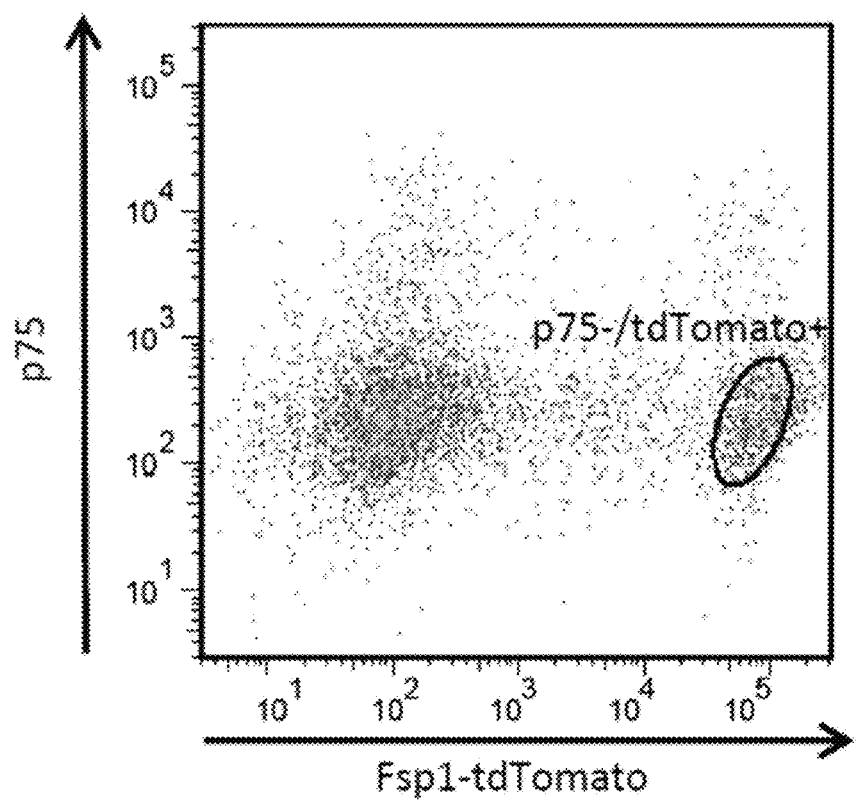
Figure 1H:
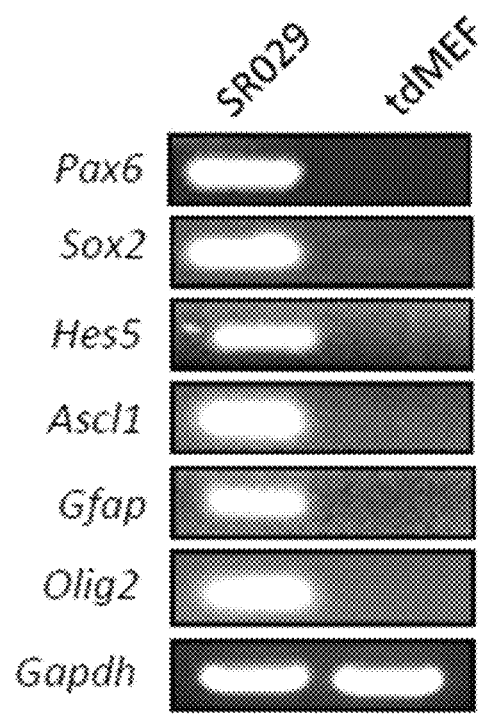
Figure 1I:
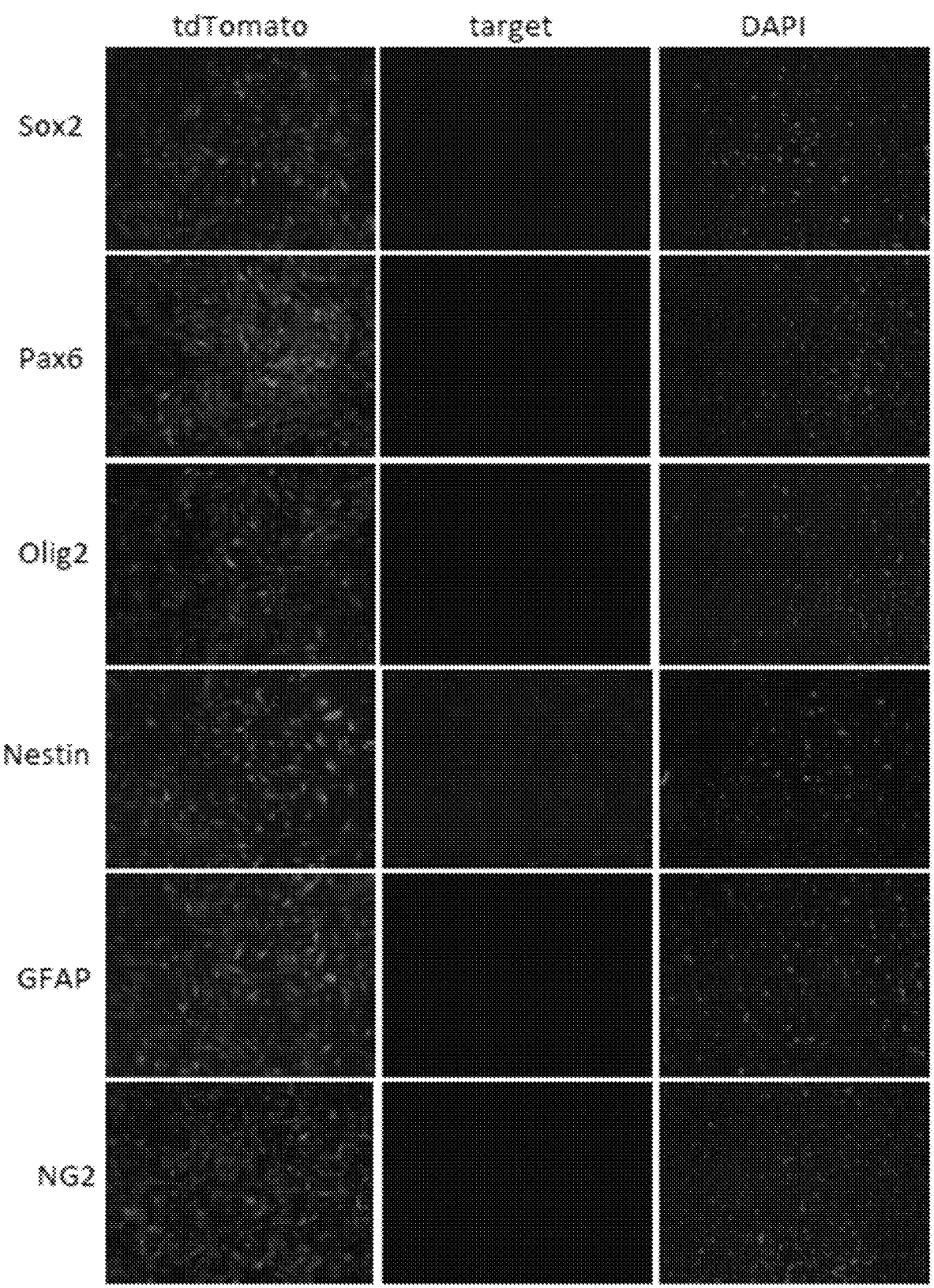

Cells were isolated from transgenic mice carrying Fsp 1-Cre/ROSA26$^{tdTomato}$ at E13.5, and the fibroblast population was permanently marked with tdTomato expression. Besides removing neural tissues from the MEF preparations, FACS sorting was performed to collect the tdTomato-positive/p75-negative population to exclude any neural crest progenitors (hereafter named tdMEF, FIGS. 1A and 1G). These tdMEF cells were negative for typical NSC markers, including Sox2, Pax6 and Olig2 (FIG. 1I). The tdMEF cells showed very low-level expression of Nestin, but the pattern was quite different from that of primary NSCs (FIG. 1I). In addition, the tdMEF cells were negative for GFAP and NG2, markers for astrocytes/radial glia cells and oligodendrocyte progenitor cells, respectively, that have the potential to become NSCs (FIG. 1I). The absence of several neural gene transcripts was also confirmed, including Pax6, Sox2, Hes5, Aash1, Gfap and Olig2, in tdMEF by RT-PCR (FIG. 1H). To further confirm the absence of neuron-producing cells, the tdMEF cells were cultured under extended neuronal differentiation condition. No Tuj1-positive neurons were detected from $10^5$ starting tdMEFs after a 15-day differentiation (data not shown). Consequently, these tdMEF cells were established as suitable starting cells for chemical-based neural reprogramming studies.

Example 3: Identification of Chemical Conditions for Reprogramming Fibroblasts into Neural Stem Cells This Example describes experiments designed to define small molecules that target and modulate epigenetic functions and neuro-developmental signaling to induce a neural transcriptional program in fibroblasts.

To begin a combinatorial chemical screening, LDN193189 (LDN, an inhibitor of BMP type I receptor ALK2/3) and A83-01 (A83, an inhibitor of TGF-type 1 receptor ALK4/5/7), which inhibit mesoderm and endoderm specification, and CHIR99021 (OUR, a GSK3 inhibitor) and basic fibroblasts growth factor (bFGF), which favor neural development, were combined as a neural induction basal condition in a chemically defined medium, on top of which other individual small molecules were screened for induction of neural reprogramming of tdMEFs. Briefly, tdMEFs were plated into neural reprogramming basal medium at 15,000 cells per well in 24-well plate, and after an overnight culture, individual small molecules from a focused chemical collection, including epigenetic modifiers, metabolism regulators, and signaling modulators, were added. Ten days post-treatment, cells were fixed, immune-stained, and analyzed for co-expression of Sox2 and Nestin, two typical NSC markers (FIG. 1A-1B).

From such primary screening, Hh-Ag 1.5 (Hh, a potent Smo agonist) and retinoic acid (RA) were found to induce the generation of 3.68% and 1.26% Sox2/Nestin double-positive cells, respectively, while DMSO-treated control wells had no Sox2/Nestin double-positive cells. These two chemicals were subsequently included in the basal condition.

Additional small molecules were screened to further supplement the six-molecule condition and that could further improve the neural induction efficiency. Notably, RG108 (RG, a DNA methyltransferase inhibitor), Parnate (Par, a histone demethylase inhibitor), and SMER28 (SR, an autophagy modulator) further enhanced the generation of Sox2/Nestin double-positive cells. These three small molecules were included in the neural induction cocktail, resulting in a nine-molecule combination of CHIR, LDN, A83, RA, Hh, RG, Par, SR and bFGF shown in Table 3 below that robustly induced Sox2/Nestin double-positive cells at percentage of about 25.62% to 30.04% (FIG. 1F).

TABLE 3

Chemicals Employed

| Chemical | Function | Structure | Working Concentration |
|---|---|---|---|
| CHIR99021 (CHIR; M.W. 465.34) | Highly potent and selective GSK-3β inhibitor | 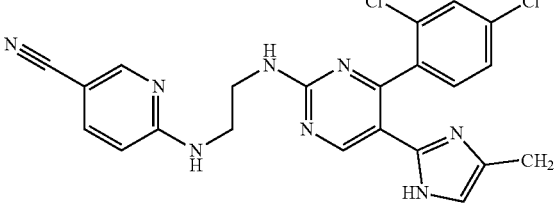 | 3 μM |
| LDN193189 (LDN; M.W. 406.48) | Cell permeable BMP type I receptor ALK2/ALK3 inhibitor | 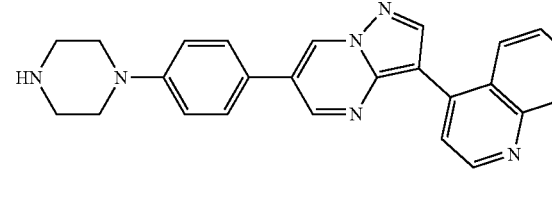 | 100 nM |
| A83-01 (A83; M.W. 421.52) | Potent inhibitor of TGF-β type I receptor ALK5 kinase, type I Activin/Nodal receptor ALK4 and type I nodal receptor ALK7 | 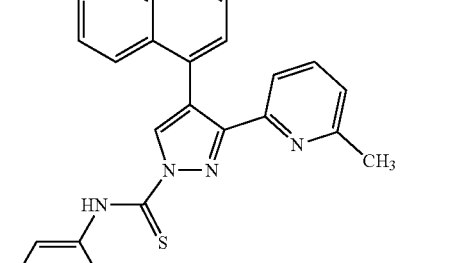 | 0.5 μM |

TABLE 3-continued

Chemicals Employed

| Chemical | Function | Structure | Working Concentration |
|---|---|---|---|
| Parnate (Par; M.W. 169.65) | Irreversible inhibitor of lysine-specific demethylase 1 and monoamine oxidase | 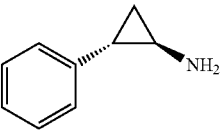 | 2 μM |
| RG108 (RG; M.W. 334.3) | Non-nucleoside DNA methyltransferase inhibitor | 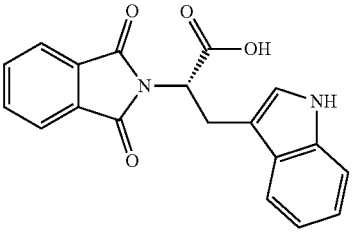 [SMILES: O=C(O)[C@H](Cc1c[nH]c2ccccc12)N1C(=O)c2ccccc2C1=O] | 10 μM |
| Retinoic Acid (RA; M.W. 300.44) | Endogenous agonist for retinoic acid receptors | 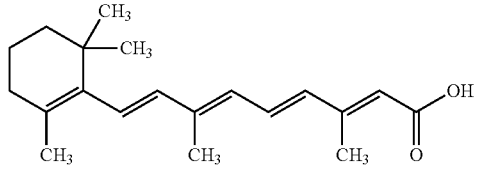 [SMILES: CC1=C(/C=C/C(C)=C/C=C/C(C)=C/C(=O)O)C(C)(C)CCC1] | 1 μM |
| SMER28 (SR; M.W. 264.12) | Positive regulator of autophagy | 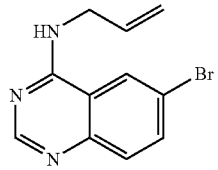 | 10 μM |
| Hg-Ag 1.5 (Hh; M.W. 526.04) | Potent Hedgehog pathway Smo agonist | 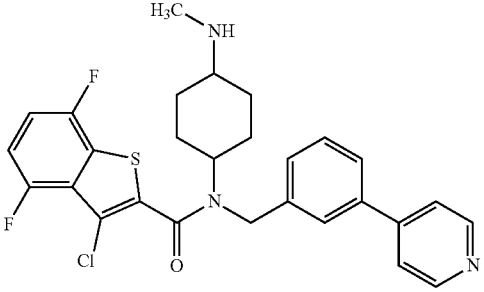 [SMILES: CNC1CCC(N(Cc2cccc(-c3ccncc3)c2)C(=O)c2sc3c(F)ccc(F)c3c2Cl)CC1] | 0.5 μM |

Figure 2A:
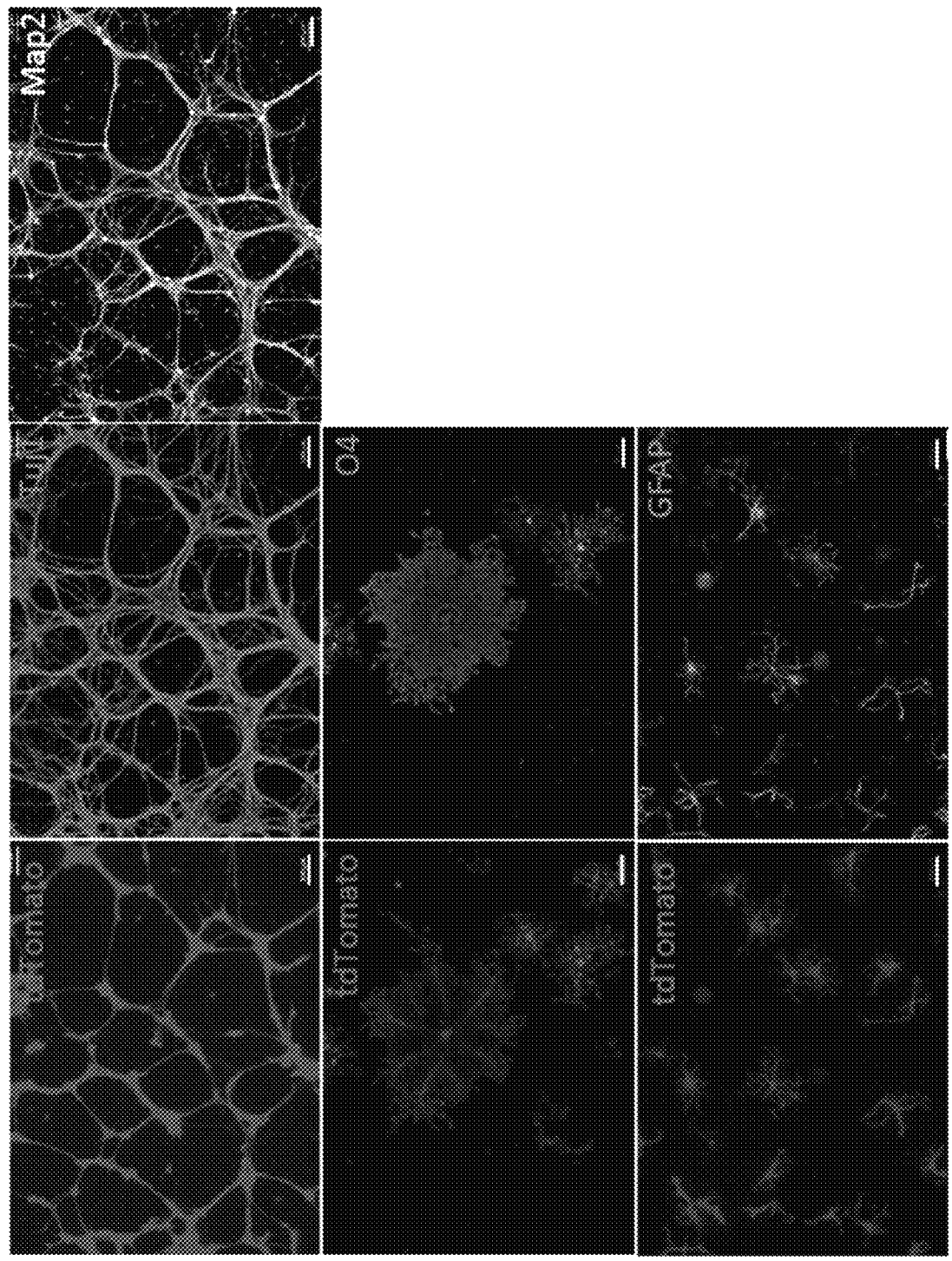
FIG. 2A-2L illustrate that ciNSLCs are tripotent in vitro and in vivo.
Figure 2B:
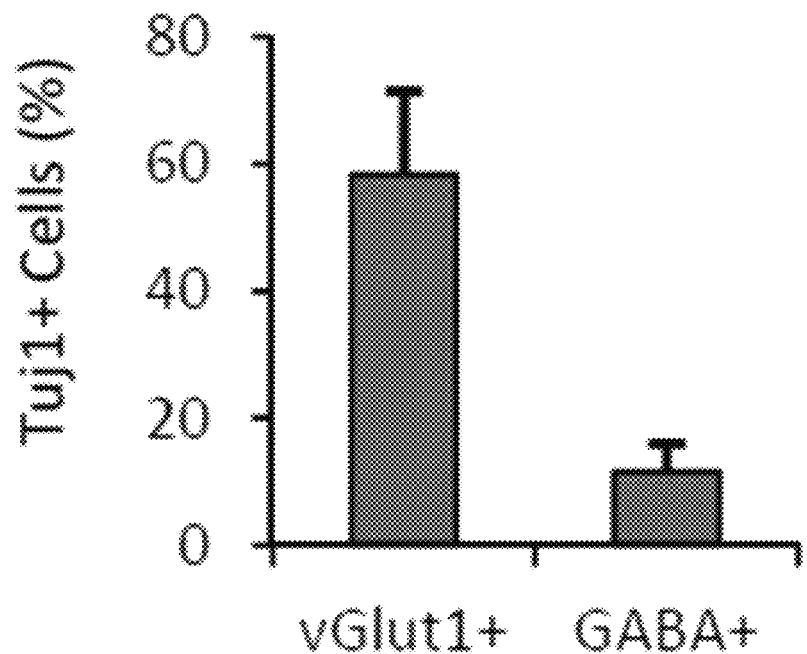
Figure 2C:
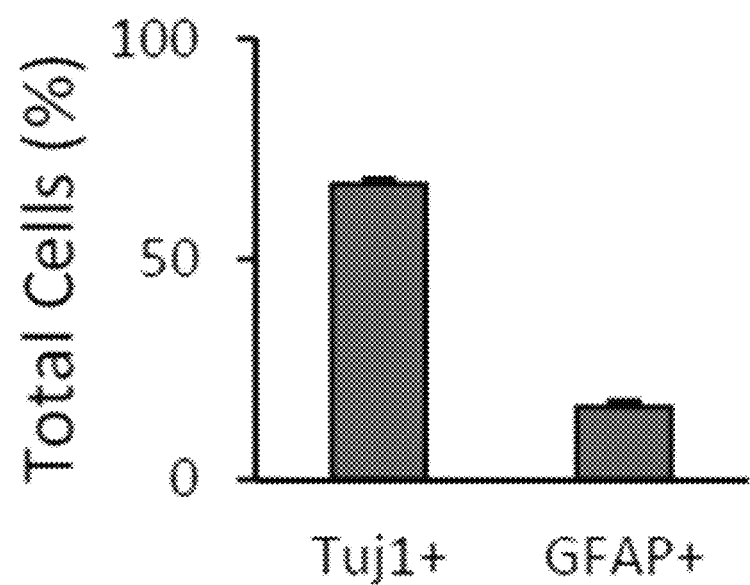
Figures 2D, 2E:
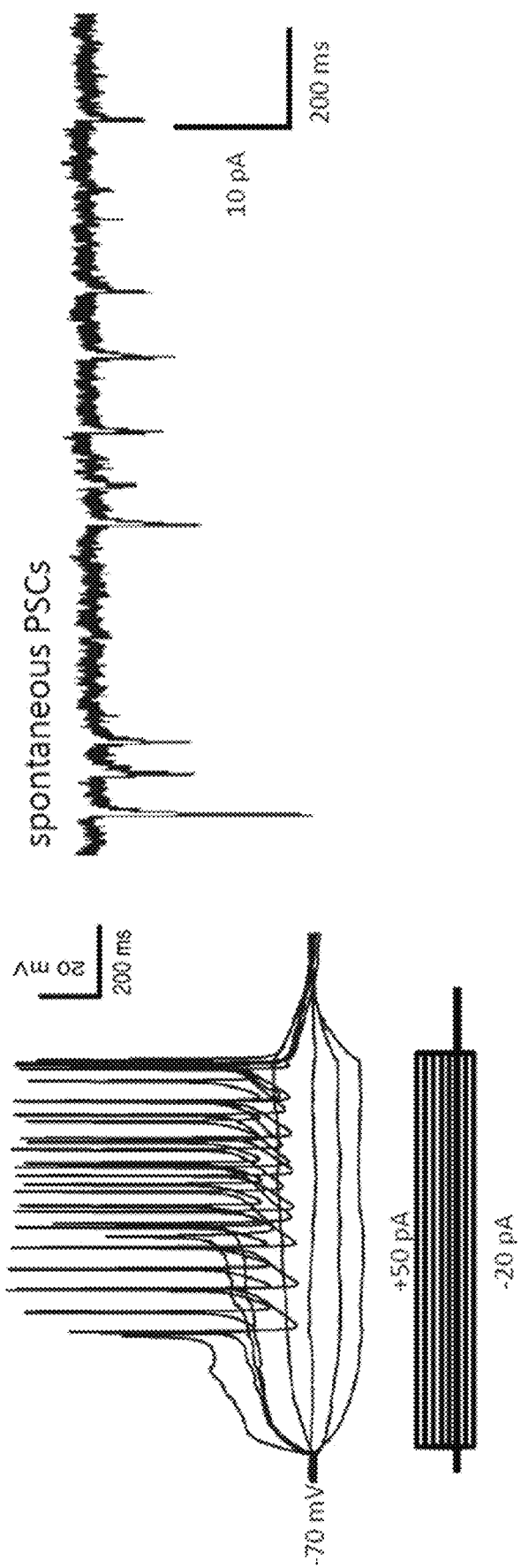
Figure 2F:
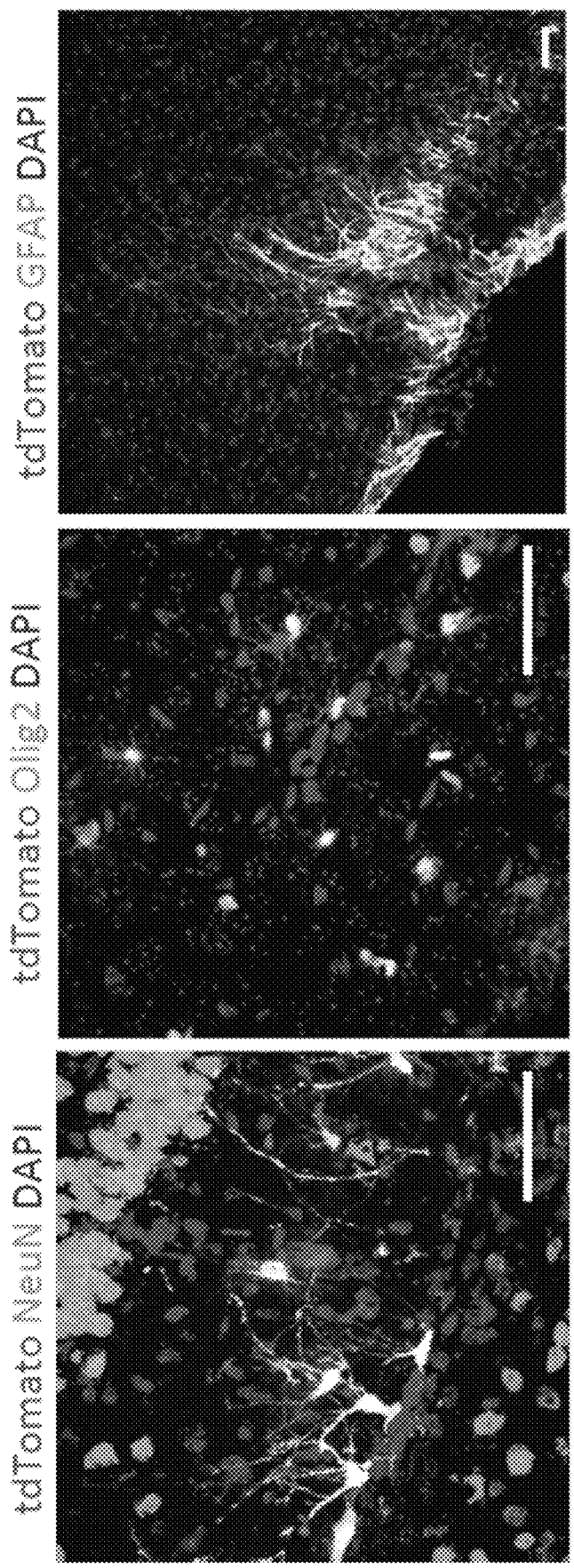
Figure 2G:
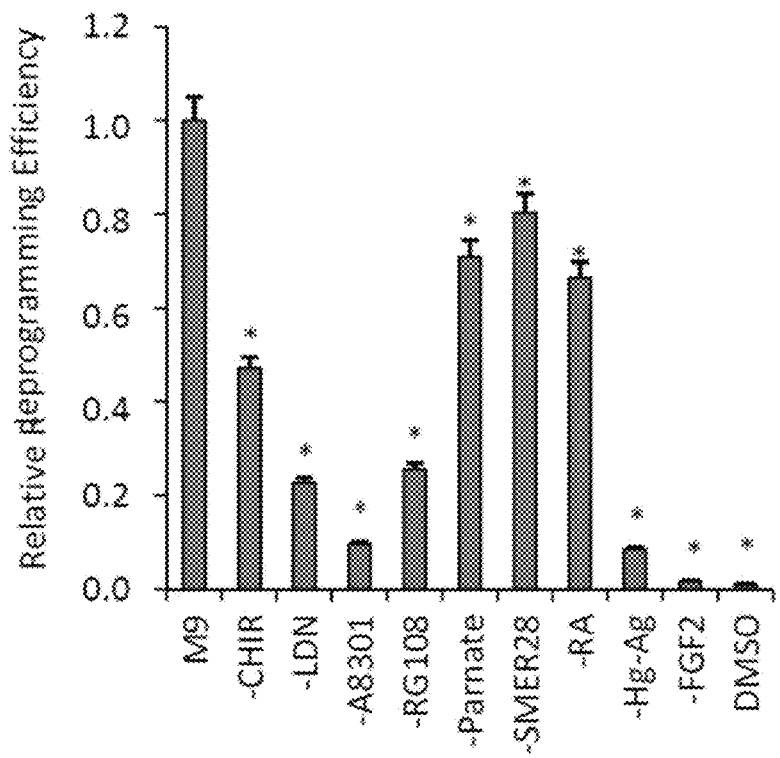

To identify key molecules, each component was individually removed from the cocktail and the neural reprogramming efficiency was evaluated (FIG. 2G). Removal of any of the nine molecules significantly compromised the reprogramming efficiency (FIG. 2G). This combination of nine molecules (named as M9 hereafter) was used in subsequent assays after optimization of dosage.

Figure 2H:
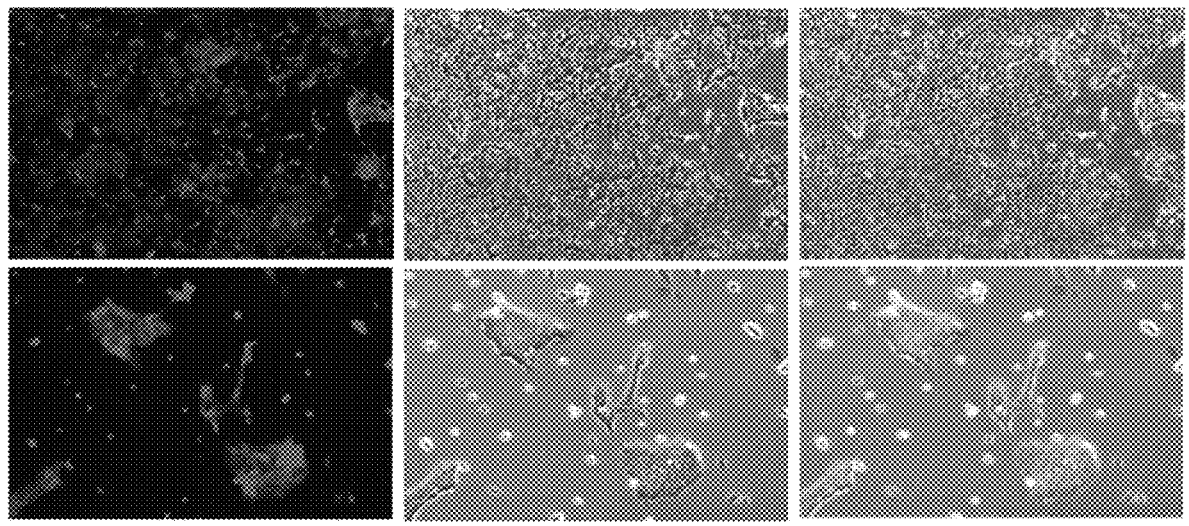
Figure 2I:
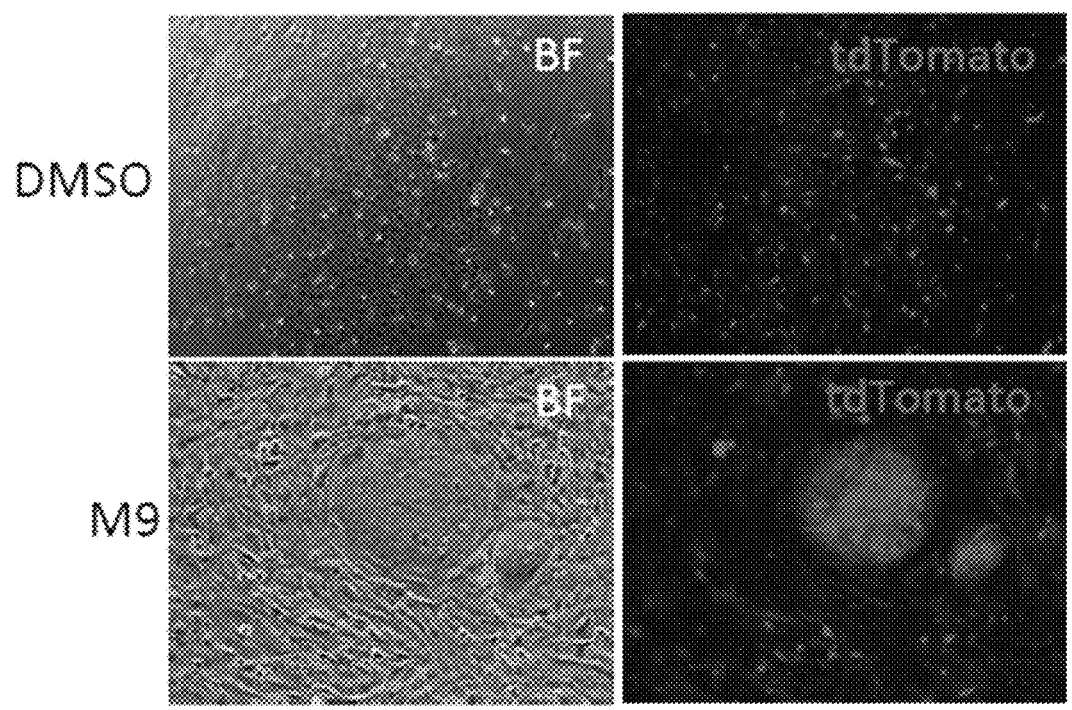
Figure 2J:
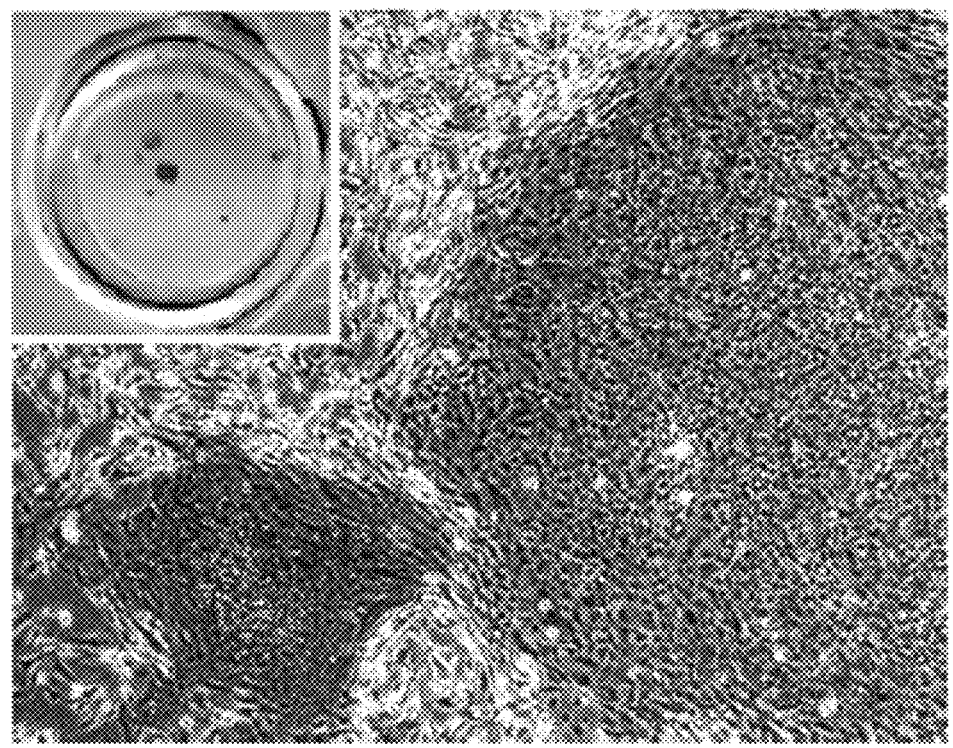
Figure 2K:
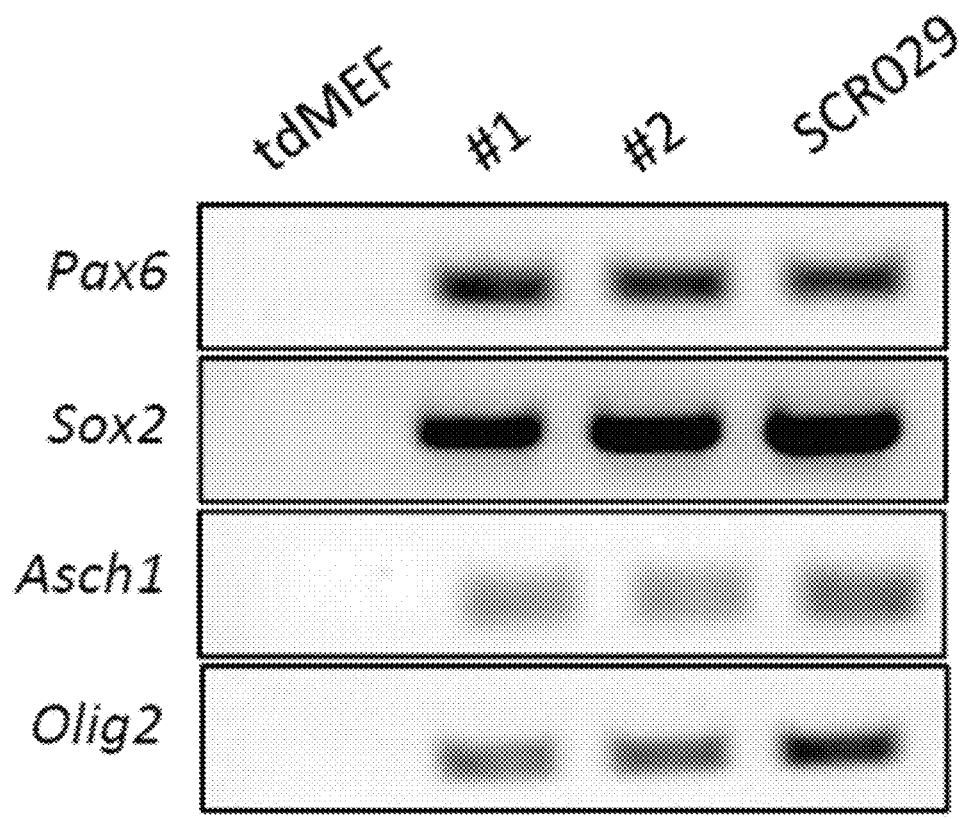
Figure 2L:
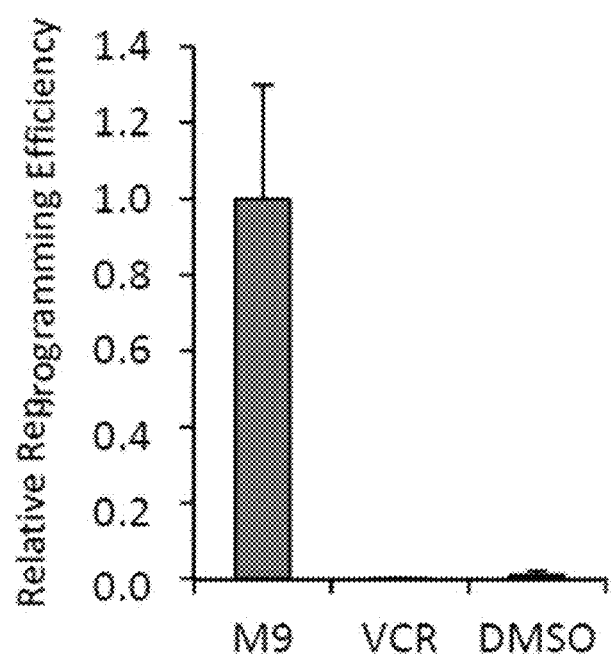

To further characterize the reprogramming process, it was observed that the M9-treated tdMEF cells morphologically underwent a characteristic mesenchymal-to-epithelial transition (MET) and small clusters/colonies gradually emerged at about day 6 (FIG. 2H-2I). These METed cell colonies were positive for alkaline phosphatase, a typical marker for NSCs (FIG. 2J), Remarkably, during day 6 to day 10, induction of the Sox2, the master transcriptional factor for NSCs, was observed in cell colonies. By day 10, the percentage of Sox2/Nestin double-positive cells reached approximately 25% (FIG. 1B, IF) Semi-quantitative RT-PCR confirmed the expression of other neural stem cell genes, including Pax6, Sox2, Ascl1, and Olig2, in this population (FIG. 2K). In contrast, tdMEFs cultured either without M9 (DMSO control), or with a cocktail of valproic acid, CHIR99021, and RepSox as reported (Cheng et al., *Cell Research* 24, 665-679 (2014)), failed to give rise to Sox2+/Nestin+ colonies, indicating the functional importance of M9 (FIG. 2G). Notably, all cells in Sox2+/Nestin+ colonies expressed tdTomato, demonstrating a conversion from fibroblasts (FIG. 1B).

Figure 3A:
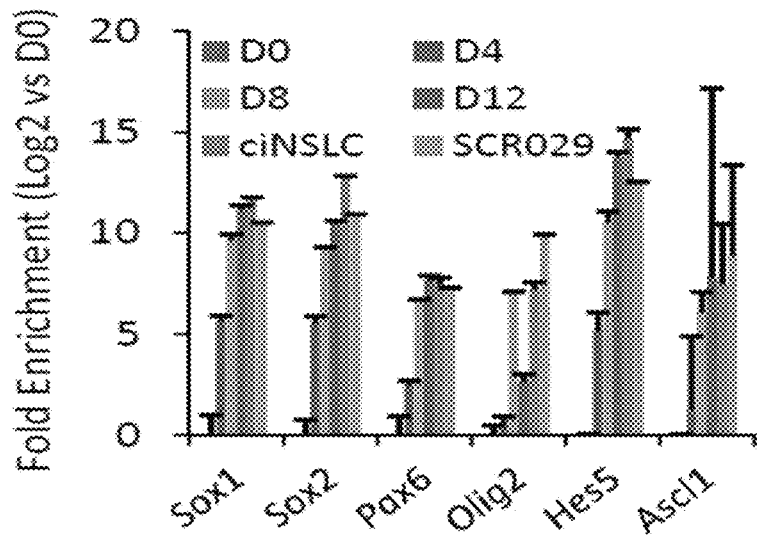
FIG. 3A-3H illustrate expression patterns of cells during neural reprogramming.

To further characterize the tdTomato+/Sox2+/Nestin+ cells, they were isolated and serially passaged in conventional NSC expansion medium containing bFGF and epidermal growth factor (EGF). Notably, they could robustly proliferate and form neurospheres over ten passages (FIG. 3G-3H), maintained typical morphology of NSCs, and expressed multiple NSC markers, including Sox2, Nestin, Olig2, and N-cadherin, by quantitative PCR and by immunostaining (FIG. 1C-ID). The expression levels of these genes were comparable to those in primary NSCs and a NSC line SCR029 (Ring et al., Cell Stem Cell 11, 100-109 (2012). Transcriptome analysis showed that ciNSLC resembled SCR029, but was distinct from tdMEF (FIG. 1E). Those fibroblast-originated, highly proliferative, and self-renewable Sox2 and Nestin double-positive cells are thereafter referred to as chemical induced neural stem cell-like cells (ciNSLCs).

Example 4: ciNSLC are Tripotent In Vitro and In Vivo

Figure 4H:
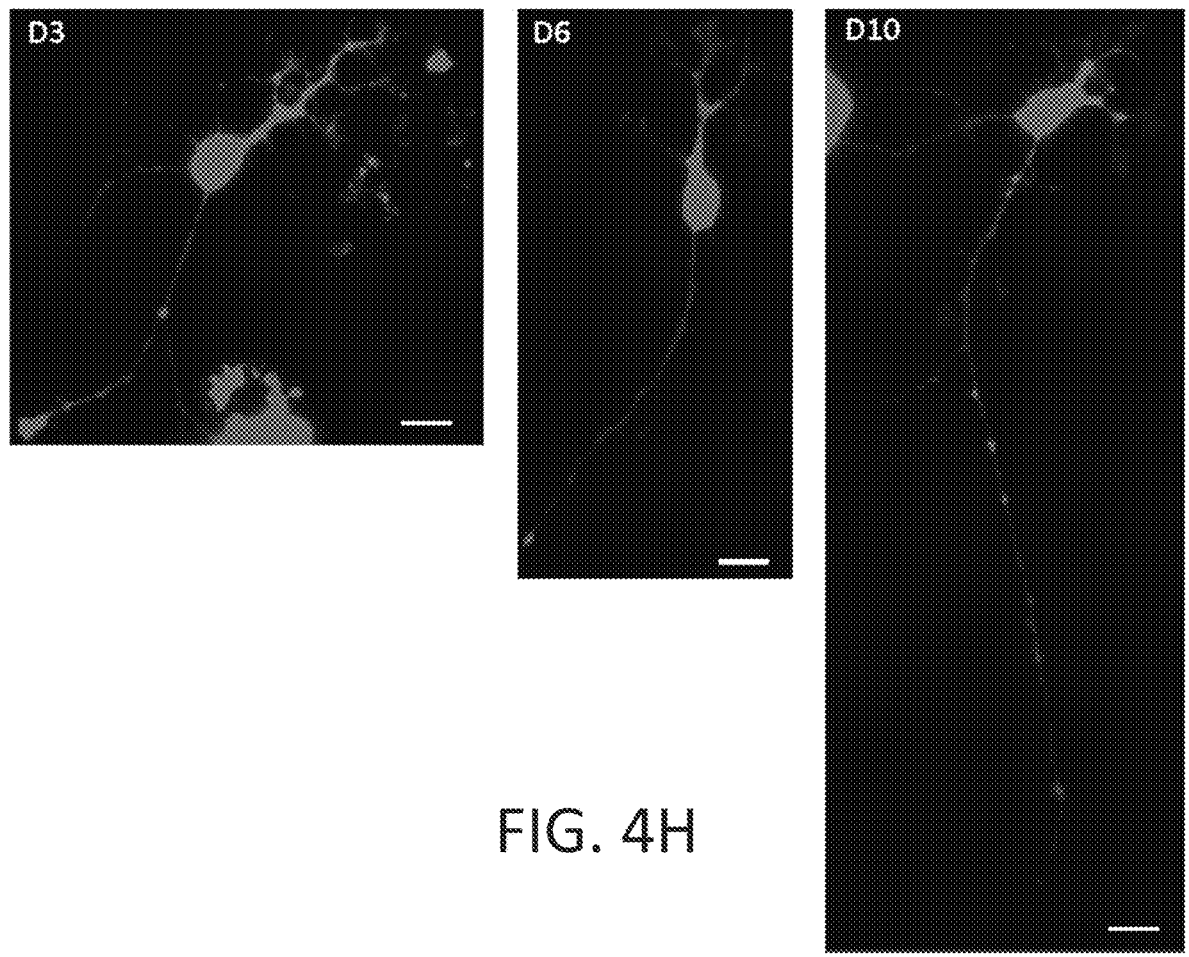
Figure 4I:
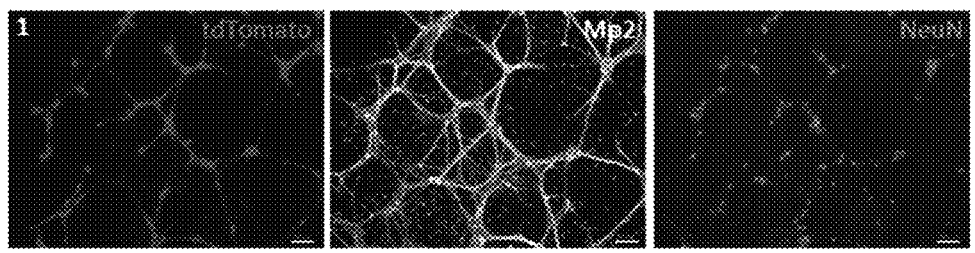
Figure 4J:
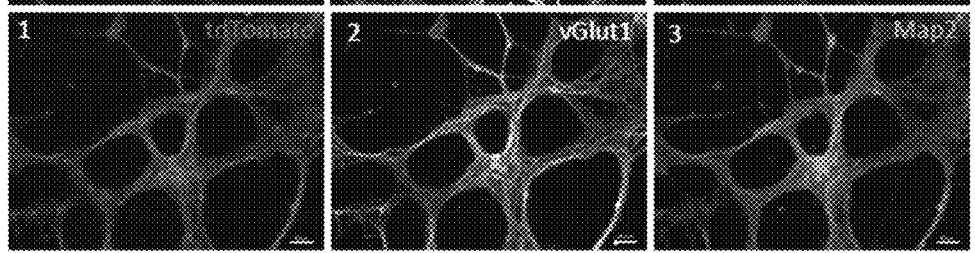
Figure 4K:
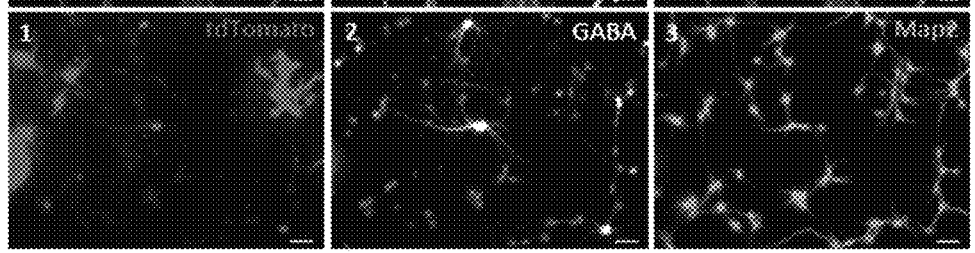
Figure 4L:
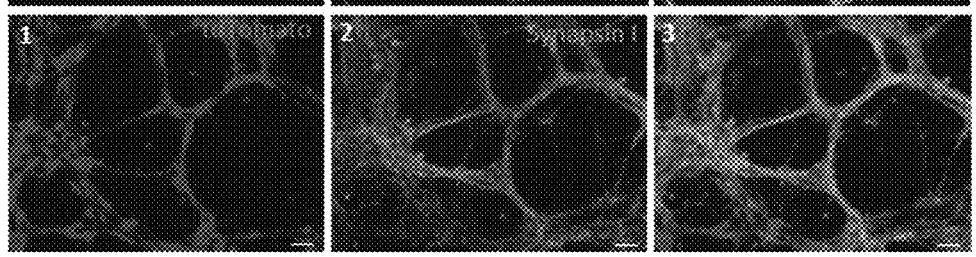
Figure 5A:
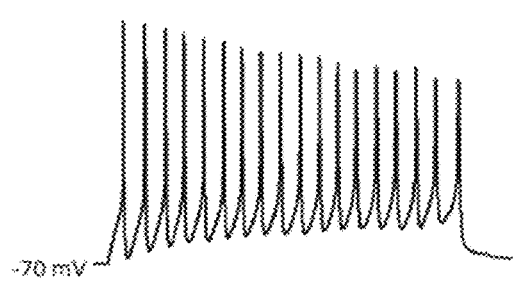
FIG. 5A-5E illustrates the membrane properties and synaptic responses of ciNSLC-derived neurons.
Figure 5B:
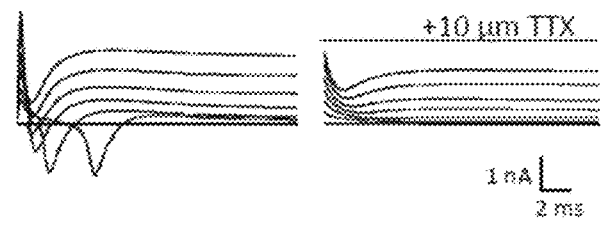
Figure 5C:
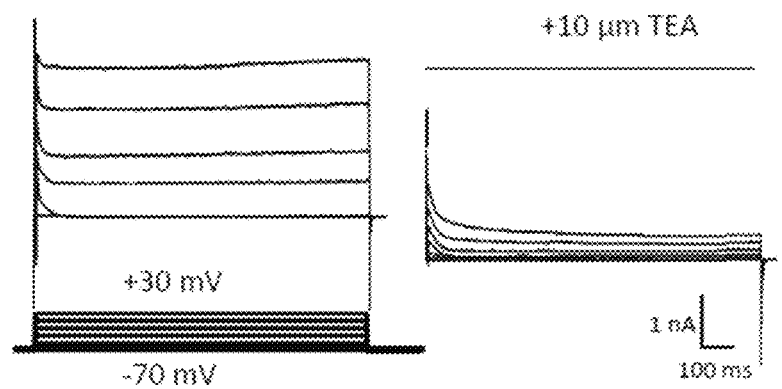
Figure 5D:
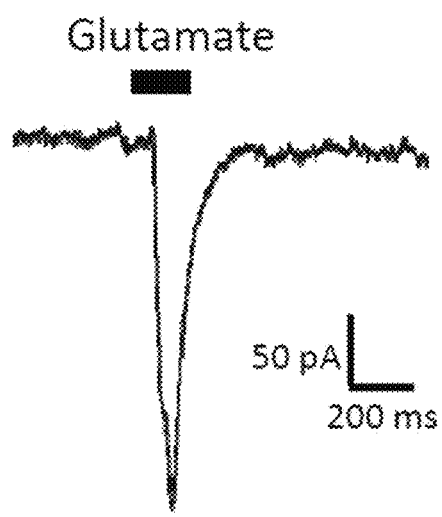
Figure 5E:
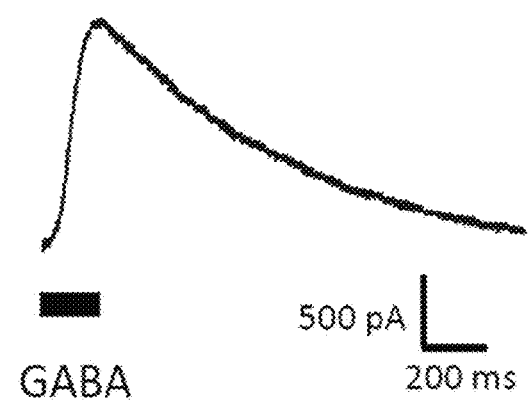

To characterize their differentiation potential, expanded ciNSLCs were first differentiated in vitro under the typical neuronal differentiation condition (Kim et al. Proc Natl Acad Sci USA 108: 7838-7843 (2011). The tdTomato-positive cells with immature neuronal morphology were observed as early as day 3 (FIG. 4H). Upon further differentiation, mature neurons with elaborate processes that expressed a panel of typical neuronal markers, including P-III tubulin, Map2, NeuN, and Synapsin 1, were readily detected at day 10 onwards (FIG. 2A, and FIG. 4I-L). As illustrated in FIG. 2A, ciNSLCs can differentiate into neurons that express Tuj1 and Map2, as well as into oligodendrocytes that express O4 and astrocytes that express GFAP. Subsequent analysis revealed that the majority of the neurons were vGlut1-positive, indicating an excitatory glutamatergic phenotype, while the percentage of GABA-positive inhibitory neurons was about 8.6~14.7% (FIG. 28 and FIG. 4J-4K). To more rigorously characterize these differentiated neurons, their electrophysiological properties were examined. As expected, the neurons generated repetitive trains of action potentials elicited by depolarizing the membrane in the current-clamp mode (FIG. 2D and FIG. 5A). In addition, the inactivating inwards and persistent outwards currents were observed in the voltage-clamp mode, which could be blocked by tetrodotoxin (TTX) or tetraethylammonium (TEA), respectively, indicating the presence of functional sodium-channels or potassium-channels (FIG. 5B-5C). Furthermore, the ciNSLC-derived neurons exhibited strong spontaneous synaptic network activities (FIG. 2E), indicating that functional synapses had formed, which is consistent with Synapsin 1 expression at the synaptic puncta along dendrites (FIG. 4I). Moreover, these neurons responded to direct activation of excitatory (Glutamate) or inhibitory neurotransmitter receptors (GABA, FIGS. 5D-5E), and exhibited postsynaptic currents. Collectively, these results demonstrate that these ciNSLCs can generate functional neurons in vitro.

In addition to neuronal differentiation, ciNSLC can differentiate into O4-positive oligodendrocytes with typical multi-branching morphology with the treatment of PDGF-AA, Shh, bFGF and T3, and characteristic GFAP-positive astrocytes when treated with BMP422 (FIG. 2A). Thus, the expanded ciNSLCs are tripotent and can robustly generate neurons, astrocytes, and oligodendrocytes under appropriate differentiation cues in vitro.

To determine their differentiation potential in vivo, ciNSLCs were microinjected into the cortex of postnatal mouse pups, and their survival and differentiation were evaluated 2-4 weeks after injection. Remarkably, tdTomato-marked ciNSLCs survived in the mouse cortex and efficiently differentiated into NeuN-positive mature neuronal cells, Olig2-positive oligodendrocytes, and GF AP-positive astrocytes (FIG. 2F). No tumors were found in the animals at four-weeks post-injection (data not shown). The ciNSLC in vivo differentiation potential was validated by two independent lines. Taken together, these data show that the expanded ciNSLCs resemble primary NSCs by marker expression and in by their abilities to self-renew and differentiate in wire and in vivo.

Finally, in addition to reproducible results with different batches of tdMEF cells (n=4), MEFs with different genetic backgrounds were also tested with the M9 neural induction condition. The neural reprogramming efficiency at day 10 after M9 treatment was about 16.4% for Tau-GFP MEF cells, and 27.95% for NGFP MEF cells (FIG. 1F). Furthermore, mouse tail-tip fibroblasts could be induced into ciNSLC by M9 albeit at a lower reprogramming efficiency (about 0.6 to 2.9%, FIG. 1F). To determine if the tdTomato-positive population exhibited any preferential response to M9 treatment, Fsp1-Cre/ROSA26$^{tdTomato}$ MEFs were sorted by FACS into p75−/tdTomato+ and p75−/tdTomato− populations, and the cells were treated with the M9 condition. About 26.7% tdTomato+ cells and about 31% tdTomato− cells became Sox2+/Nestin+ ciNSLCs after M9 treatment, demonstrating a comparable neural conversion (FIG. 6). These results collectively demonstrated that the M9 cocktail has a robust and general effect on reprogramming fibroblasts into NSCs.

Figure 7A:
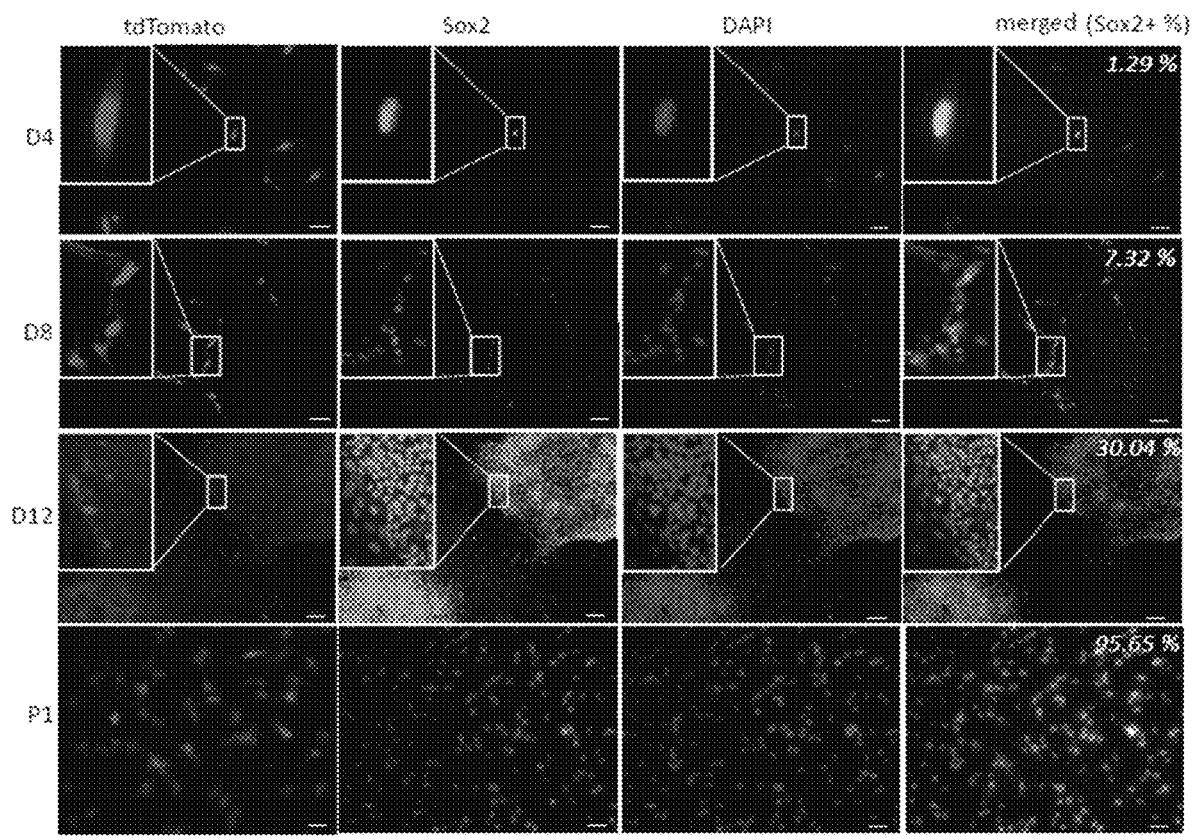
FIG. 7A-7C illustrate activation of master neural genes by the M9 cocktail composition.
Figure 7B:
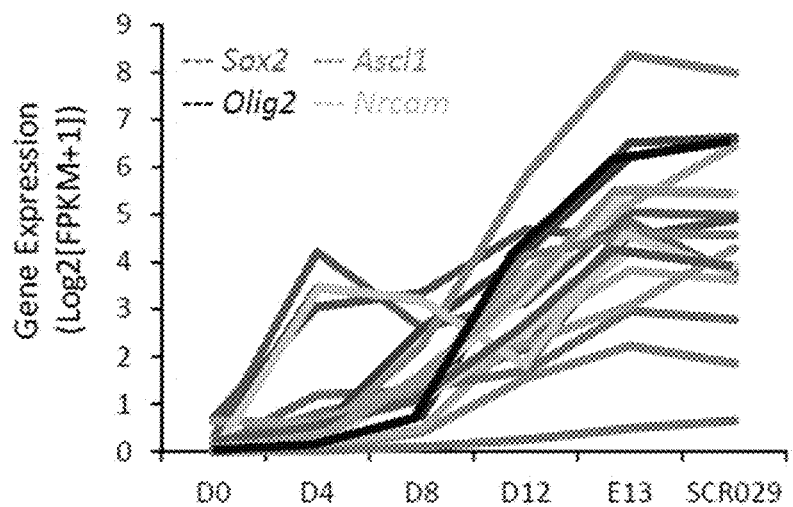

Example 5: Transcriptional Roadmap of Chemical-Induced Neural Stem Cell Reprogramming To monitor the activation of endogenous master transcriptional regulators of NSCs, Sox2 was initially examined by immunostaining (FIG. 7A). Induction of endogenous Sox2 protein expression in individual cells could be observed as early as day 4 after M9 treatment, at which time 1.29% of the cells exhibited Sox2 expression, and the number of Sox2-positive cells increased significantly by around day 8 in those that had undergone mesenchymal-to-epithelial transition and formed small clusters/colonies (7.32%). By day 12, robust expression of Sox2 was detected in cells within the large and flat colonies (30.04%). In addition to Sox2, similar kinetics of gene activation for other neural genes, such as Pax6, Olig2, Hes5 and Ascl1, was also detected by quantitative PCR or RNA-seq (FIG. 3A and FIG. 7B), indicating that M9 effectively activated the intrinsic neural transcriptional program.

Figure 3B:
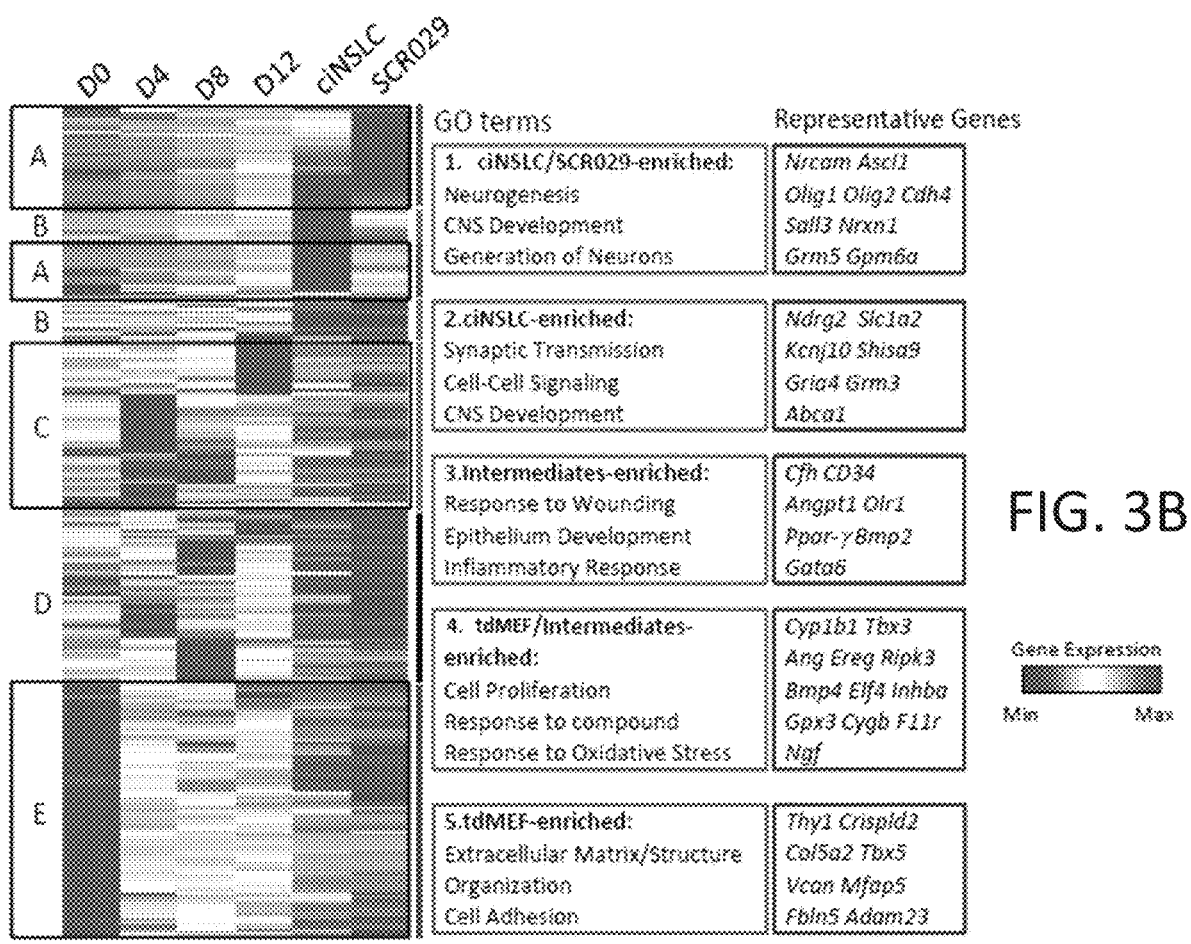
Figure 3C:
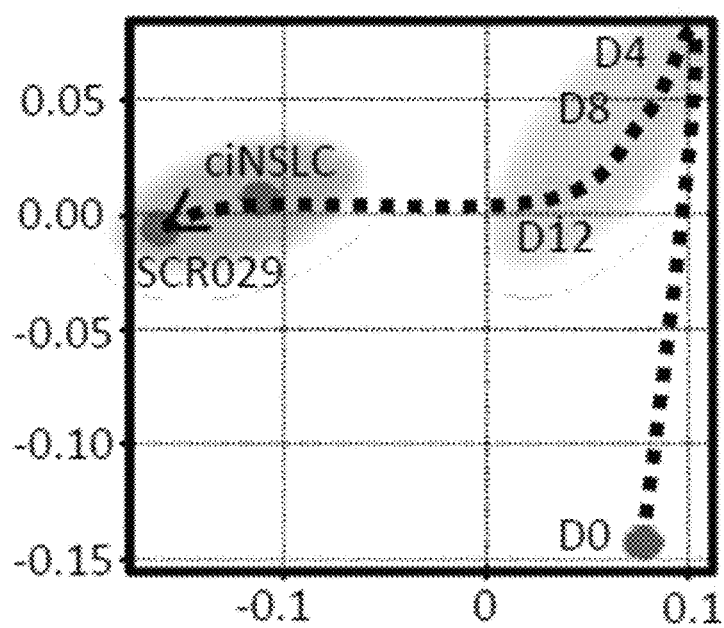
Figure 3D:
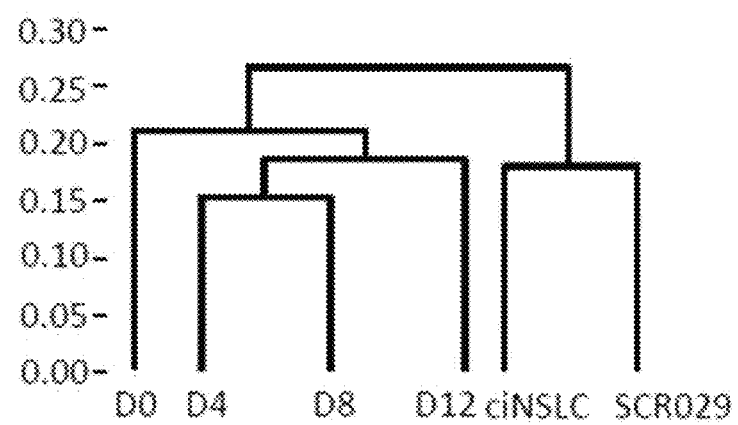
Figure 8A:
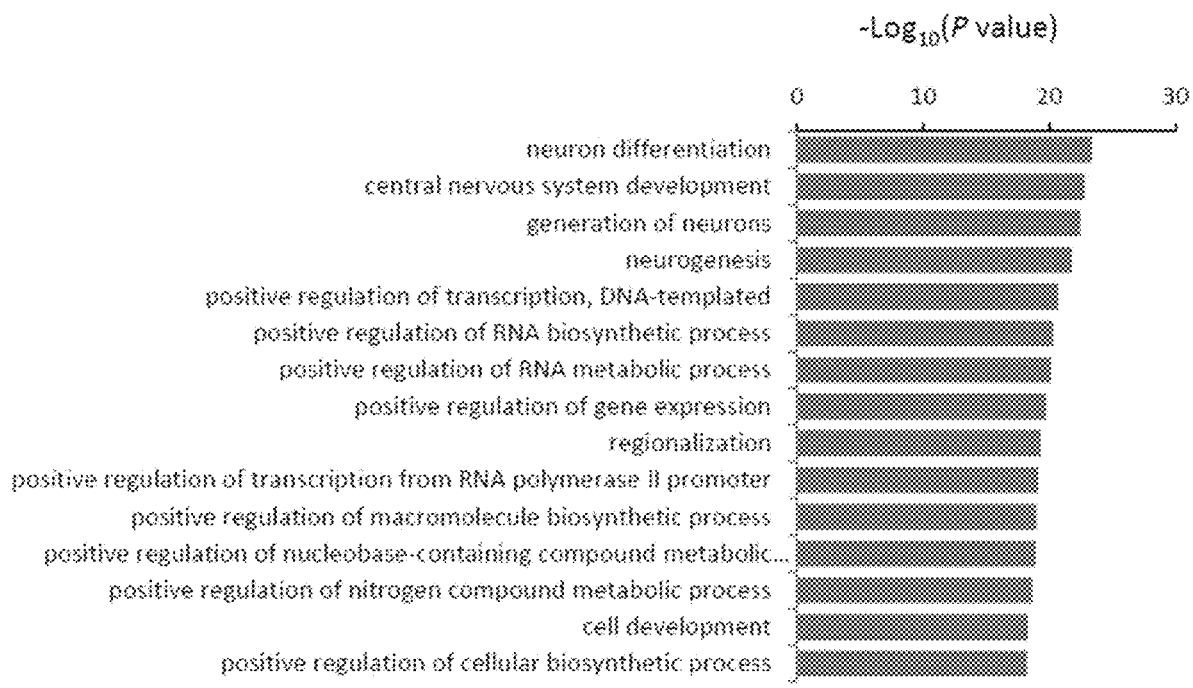
FIG. 8A-8B illustrate the gene ontology of the ciNSLC transcriptome.

To elucidate the reprogramming route, transcriptome analysis of the ciNSLC induction process was performed by RNA-seq (FIG. 3B). Principle components analysis revealed that all intermediates, upon M9 treatment, were distinct from starting tdMEFs (D0), indicating M9 treatment led to dramatic transcriptional changes (FIG. 3C). Paired scatter plots and hierarchical cluster analysis showed that ciNSLCs and control NSCs were similar in transcriptional profile, but clearly differed from tdMEF (FIG. 1E, FIG. 3D), demonstrating a NSC identity. By analyzing the differentially expressed genes, a gradual transition from fibroblasts towards NSCs was identified. The genes differentially expressed in both ciNSLCs and control. NSCs fell into the categories of neural development related biological processes, confirmed an acquisition of NSCs identity (FIG. 3B and FIG. 8A), whereas genes that were down-regulated from day 4 onwards were involved in fibroblast function, such as extracellular matrix/structure organization and cell adhesion. Interestingly, genes showing transient activation in reprogramming intermediates were determined to be involved in inflammatory responses/wound healing, as well as epithelium development, which is consistent with previous studies showing that the activation of innate immunity and the mesenchymal-to-epithelial transition process are important for efficient reprogramming (Li et al., *Cell Stem Cell* 7: 51-63 (2010); Lee et al., *Cell* 151, 547-558 (2012)).

Figures 3E, 3F:
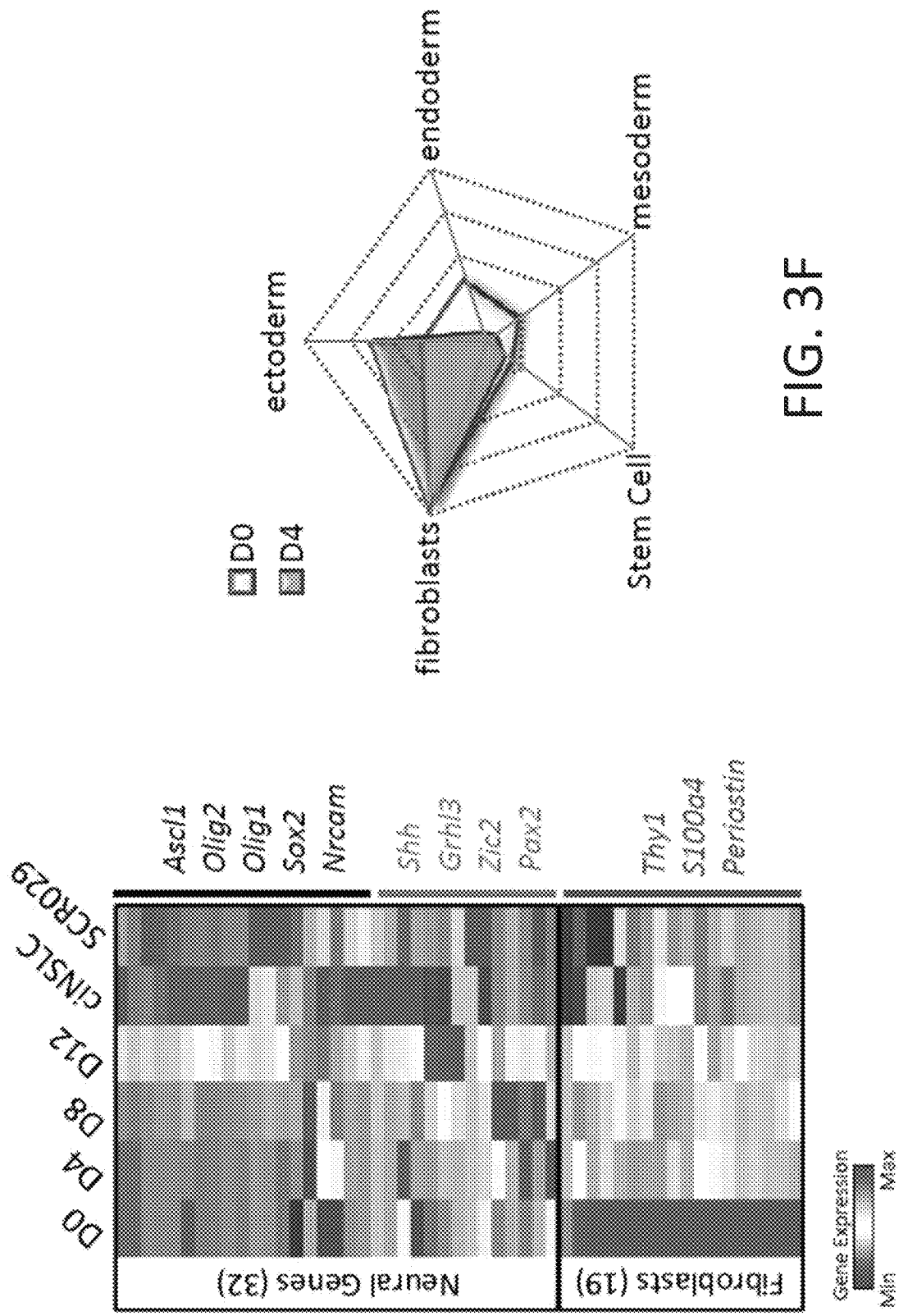
Figure 3G:
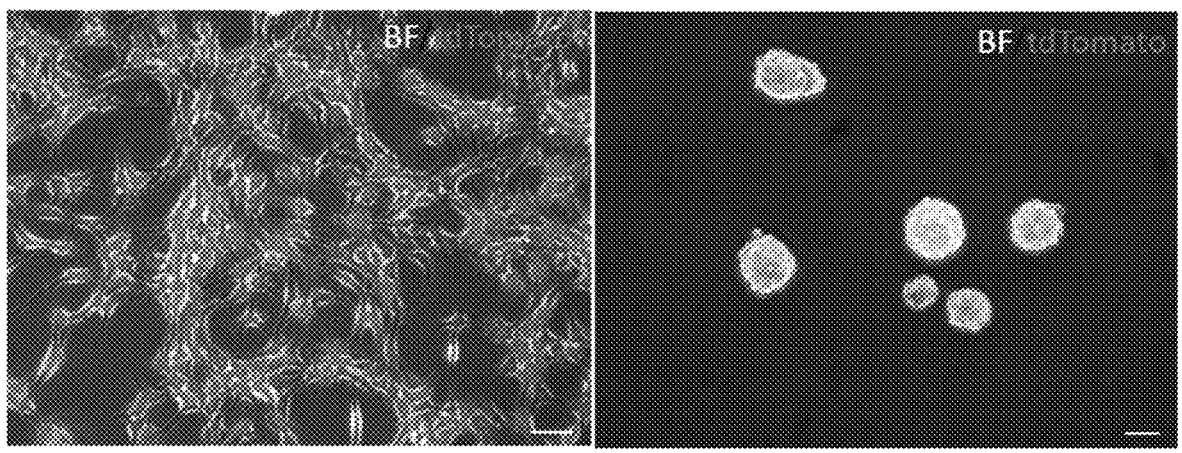
Figure 3H:
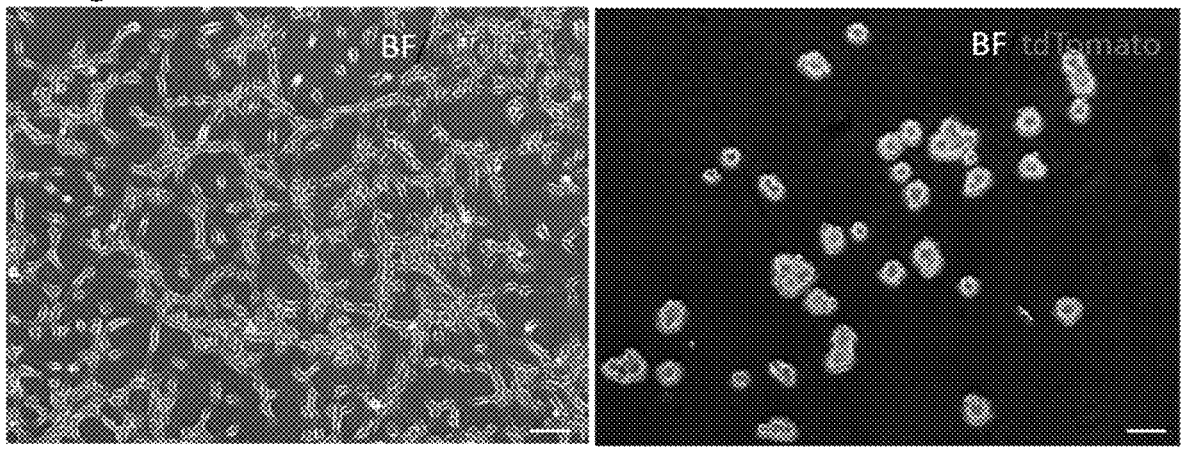
Figure 8B:
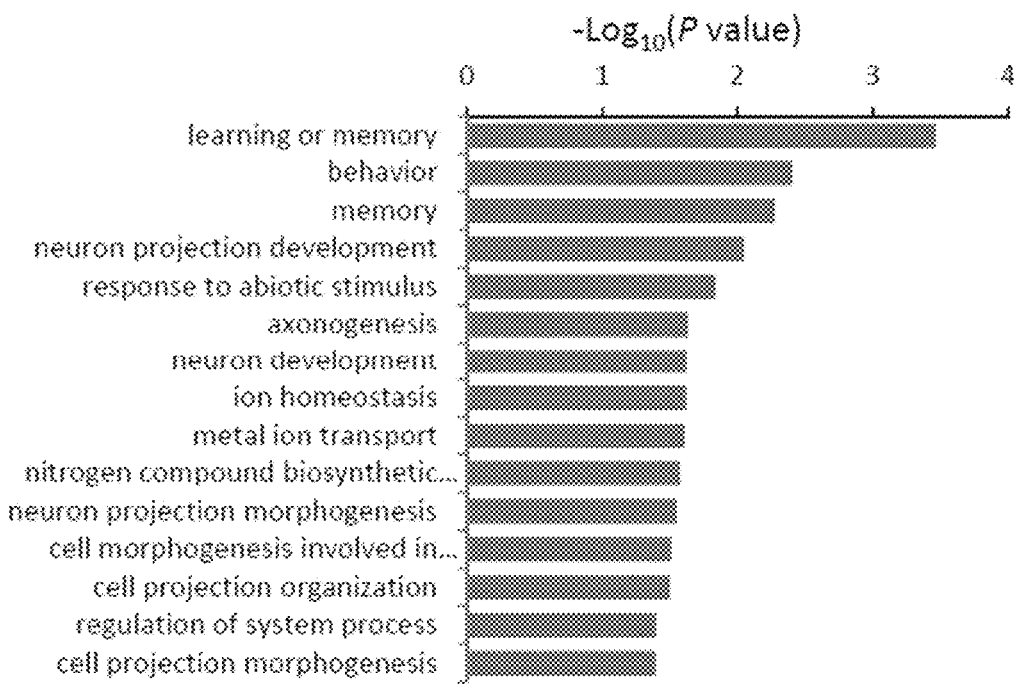

To confirm this fibroblast-to-NSC transition, the expression of nineteen fibroblast- and 32 NSC-enriched genes were evaluated. As shown in FIG. 3E fibroblast genes, such as Thy1, S100α4, Periostin, and Snail, were significantly downregulated; whereas a panel of NSC genes was gradually upregulated during the ciNSLC induction process. As shown in FIG. 8B, although there was a gradual acquisition of neural genes, the transcripts of other lineage-specific genes, such as Nanog and Oct4 (pluripotency), T and Mesp1 (mesoderm), and Sox17 and Foxa2 (endoderm) could not be detected. These data indicate that the M9 composition and the methods described herein are a specific program for activation of NSC.

To confirm neural induction specificity, the expression of a cohort of genes was analyzed, where the genes were under the GO terms of ectoderm development, mesoderm development, endoderm development, fibroblasts, and stem cell maintenance, at day 4 after M9 treatment. As shown in FIG. 3F, the observed transcriptional activation was predominantly towards ectoderm, rather than other lineages.

Figure 7C:
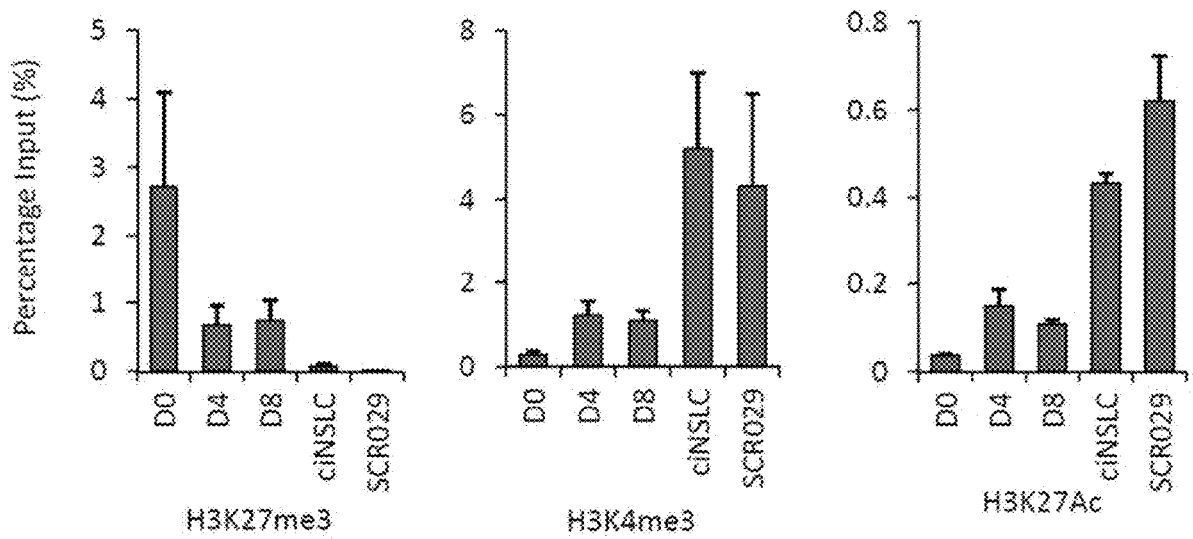

To investigate how transcriptional rewiring was achieved at the epigenetic level, histone modifications were examined, including expression of H3K4me3, H3K27me3, and H3K27Ac at the Sox2 promoter. In agreement with the transcriptional profile, M9 treatment dramatically reduced H3K27me3 expression, while concomitantly increasing expression of H3K4me3 and H3K27Ac (FIG. 7C). These data indicate that the cells had undergone a transition from repressive to active chromatin status upon M9 treatment. This epigenetic pattern was firmly established in ciNSLCs, and resembled the epigenetic pattern of primary NSCs.

Example 6: Transcriptional Activation Downstream of bFGF and Hh Contributes to Neural Specificity in Reprogramming While withdrawal of any of the nine molecules significantly reduced the reprogramming efficiency, omitting bFGF or Hg—Ag 1.5 affected the ciNSLC induction most (FIG. 2G). To confirm the function of bFGF and Hg—Ag 1.5 on the reprogramming, the inhibition of these pathways was examined to ascertain how downstream signaling and ciNSLC induction was affected.

To dissect the function of bFGF signaling, the major downstream pathways triggered by bFGF, including mitogen-activated protein kinase (MAPK) pathways, and phosphatidylinositol 3-kinase (PI3K) pathway, were individually blocked by the following specific small molecule inhibitors: PD0325901 (a MEK inhibitor), SP600125 (a JNK inhibitor), SB203580 (a p38 inhibitor), or LY294002 (an inhibitor of PI3K kinases), under the M9 induction condition. As shown in FIG. 4A, the reprogramming efficiency was dramatically reduced about 9-fold by addition of PD0325901, 6-fold by addition of SP600125, 5-fold by addition of SB203580, and 4-fold by addition of LY294002. These data indicate that bFGF has a variety of contributions to downstream signaling pathways that affect its reprogramming inducing activities.

Inhibition of the Hg—Ag 1.5 pathway by LDE-225 (a Smo antagonist) also significantly reduced the reprogramming efficiency about 6-fold (FIG. 4B).

Given the functional importance of bFGF and Hg—Ag 1.5 in ciNSLC reprogramming, the inventors hypothesized that the immediate downstream transcription factors of the bFGF and Hg—Ag 1.5 pathways may directly participate in transcriptional activation of endogenous master NSC genes, such as Sox2. Elk1 and Gli2 are the major direct transcription factors downstream of the bFGF pathway and the Hg—Ag 1.5 pathway, respectively.

To establish whether Elk1 and Gli2 directly participated in the activation of endogenous Sox2, the binding of Elk1 and Gli2 to Sox2 promoter was analyzed by ChIP-qPCR. Sox2 is expressed at high levels in neuroepithelial stem cells and persists in neural stem/progenitor cells throughout adulthood. Sox2 has at least two regulatory regions in addition to the core promoter, the Sox2 regulatory region 1 (SRR1) and the Sox2 regulatory region 2 (SRR2; FIG. 4C), which drive strong expression in these cells.

Remarkably, M9 treatment significantly triggered the recruitment and binding of Elk1 and Gli2 to the Sox2 promoter by as early as day 4 of M9 treatment (FIG. 4C), confirming that Elk1 and Gli2 participate in Sox2 gene activation. This recruitment of Elk 1 and Gli2 to Sox2 promoter also coincided with the acquisition of active chromatin status (FIG. 7C) and the activation of neural program (FIG. 3).

To confirm their regulatory role, individual knock-down of Elk1 and Gli2 was examined by shRNA to ascertain how such knock-down affected ciNSLC induction under the M9 condition. Consistent with the above results (FIGS. 4A-4B and FIG. 2G), knocking down either of these genes reduced the reprogramming efficiency. Hence, these transcription factors do have a positive regulatory role of in reprogramming (FIG. 4D-4E).

To test whether they primed neural fate at an early stage, the reprogramming efficiency of Elk1 and Gli2 was evaluated when they were knocked down at different time points. Early-stage Elk1 or Gli2 knockdown (D0 and D4 versus D8) resulted in a more serious reduction on the reprogramming efficiency. For example, a 5-fold reduction was observed when Elk1-shRNA was transduced at D0, and a 12-fold reduction was observed when Elk1-shRNA was transduced at D4, but a 3-fold reduction was observed when Elk1-shRNA was transduced at D8. For Gli2, a 7-fold reduction was observed when Gli2-shRNA was transduced at D0, and a 5-fold reduction was observed when Gli2-shRNA was transduced at D4, but only a 1-fold reduction was observed when Gli2-shRNA was transduced at D8 (FIG. 4D-4E).

On the other hand, overexpression of Elk1 or Gli2 further enhanced reprogramming efficiency in the presence of M9, by 3-fold and 5-fold, respectively (FIG. 4F). Collectively, these results demonstrate that Elk1 and Gli2 (especially under M9 conditions) are direct transcription factors inducing neural fate and these transcription factors play an role at the early stage of chemically induced neural reprogramming.

Therefore, the foregoing experiments demonstrate that the M9 mixture of small molecules enables efficient and specific reprogramming of mouse fibroblasts into ciNSLCs. The ciNSLCs resemble primary NSCs in several key aspects, including their molecular profiles, their ability to self-renew long-term, and their ability to differentiate into functional neurons, astrocytes, and oligodendrocytes in vitro and in vivo.

Importantly, genetic lineage tracing unambiguously defined the origin of reprogrammed cells as differentiated fibroblasts, supporting a bona fide reprogramming process rather than other possible inductive routes to neural lineage. Furthermore, in-depth functional studies demonstrate the post-synaptic potential for the ciNSLC-derived mature neurons and in vivo engraftment of ciNSLCs established the full potentials of ciNSLC. Hence, the data shown herein authenticates the chemical reprogramming approach.

REFERENCES

Lujan, E., Chanda, S., Ahlenius, H. Sudhot: T. C. & Wernig, M. Direct conversion of mouse fibroblasts to self-renewing, tripotent neural precursor cells. *Proc Natl Acad Sci USA* 109, 2527-2532 (2012).

Lu, J. et al. Generation of integration-free and region-specific neural progenitors from primate fibroblasts. *Cell Rep* 3, 1580-1591 (2013).

Han, D. W. et al. Direct Reprogramming of Fibroblasts into Neural Stem Cells by Defined Factors. *Cell Stem Cell* (2012).

Thier, M. el al. Direct Conversion of Fibroblasts into Stably Expandable Neural Stem Cells. *Cell Stem Cell* (2012).

Kim, J. et al. Direct reprogramming of mouse fibroblasts to neural progenitors. *Proc Natl Acad Sci USA* 108: 7838-7843 (2011).

Zhu, S., Wang, H. & Ding, S. Reprogramming fibroblasts toward cardiomyocytes, neural stem cells and hepatocytes by cell activation and signaling-directed lineage conversion. *Nat Protoc* 10: 959-973 (2015).

Zhu, S. et al. Small molecules enable OCT4-mediated direct reprogramming into expandable human neural stem cells. *Cell Res* 24: 126-129 (2014).

Wang, L. et al. Generation of integration-free neural progenitor cells from cells in human urine. *Nat Methods* 10, 84-89 (2013).

Zhang, M., Li, K., Xie, M. & Ding, S. Chemical Approaches to Controlling Cell Fate. *Principles of Developmental Genetics, 2nd Edition* (2014).

Xu, T., Zhang, M., Laurent, T., Xie, M. & Ding, S. Chemical Approaches for Modulating Lineage-Specific Stem Cells and Progenitors. *Stem Cells Translational Medicine* 2, 355-361 (2013).

Ring, K. L. et al. Direct reprogramming of mouse and human fibroblasts into multipotent neural stem cells with a single factor. *Cell Stem Cell* 11: 100-109 (2012).

Cassady, J. P. et al. Direct lineage conversion of adult mouse liver cells and B lymphocytes to neural stem cells. *Stem Cell Reports* 3, 948-956 (2014).

Cheng, L. et at Generation of neural progenitor cells by chemical cocktail and hypoxia. *Cell Research* 24, 665-679 (2014).

Qian, L. et al. In vivo reprogramming of murine cardiac fibroblasts into induced cardiomyocytes. *Nature* 485, 593-598 (2012).

Kondo, T. & Raft: M. Oligodendrocyte precursor cells reprogrammed to become multipotential CNS stem cells. *Science* 289, 1754-1757 (2000).

Doetsch, F., Caille, I., Lim, D. A., Garcia-Verdugo, J. M. & Alvarez-Buylla, A. Subventricular zone astrocytes are neural stem cells in the adult mammalian brain. *Cell* 97, 703-716 (1999).

Smith, W. C. & Harland, R. M. Expression cloning of noggin, a new dorsalizing factor localized to The Spemann organizer in Xenopus embryos. *Cell* 70, 829-840 (1992).

Smith, J R. el al. Inhibition of Activin/Nodal signaling promotes specification of human embryonic stem cells into neuroectoderm. *Dev Biol* 313, 107-117 (2008), Chambers, S. M. et al. Highly efficient neural conversion of human ES and iPS cells by dual inhibition of SMAD signaling. *Nat Biotechnol* 27, 275-280 (2009).

Li, W. et al. Rapid induction and long-term self-renewal of primitive neural precursors from human embryonic stem cells by small molecule inhibitors. *Proc Natl Acad Sci USA* 108: 8299-8304 (2011).

Gritti, A. et al. Multipotential stem cells from the adult mouse brain proliferate and self-renew in response to basic fibroblast growth factor. *J Neurosci* 16: 1091-1100 (1996).

Najm, F. J. et al. Transcription factor-mediated reprogramming of fibroblasts to expandable, myelinogenic oligodendrocyte progenitor cells. *Nat Biotechnol* 426-433 (2013).

Li, R. et al. A mesenchymal-to-epithelial transition initiates and is required for the nuclear reprogramming of mouse fibroblasts. *Cell Stem Cell* 7: 51-63 (2010).

Lee, J. et al. Activation of innate immunity is required for efficient nuclear reprogramming. *Cell* 151, 547-558 (2012).

Fang, R. et al. Generation of Naive Induced Pluripotent Stem Cells from Rhesus Monkey Fibroblasts. *Cell Stem Cell* 15 (2014).

Takanaga, H. et al. Gli2 is a novel regulator of Sox2 expression in telencephalic neuroepithelial cells. *Stem Cells* 27: 165-174 (2009).

Lai, K., Kaspar, B. K., Gage, F. H & Schaffer, D. V. Sonic hedgehog regulates adult neural progenitor proliferation in vitro and in vivo. *Nat Neurosci* 6: 21-27 (2003).

Machold, R. et al. Sonic hedgehog is required for progenitor cell maintenance in telencephalic stem cell niches. *Neuron* 39, 937-950 (2003), Besnard, A., Galan-Rodriguez, B., Vanhoutte, P. & Caboche, J, Elk-1 a transcription factor with multiple facets in the brain. *Front Neurosci* 5: 35 (2011).

Wernig, M. et al. A drug-inducible transgenic system for direct reprogramming of multiple somatic cell types. *Nat Biotechnol* 26: 916-924 (2008).

Zhang, M. L. et al. Yeast telomerase subunit Estlp has guanine quadruplex-promoting activity that is required for telomere elongation. *Nat Struct Mol Biol* 17: 202-209 (2010).

Kim, D. et al. TopHat 2: accurate alignment of transcriptomes in the presence of insertions, deletions and gene fusions. *Genome Biology* 14 (2011).

Liao, Y., Smyth, G. K. & Shi, W. FeatureCounts: an efficient general-purpose program for assigning sequence reads to genomic features. *Bioinformatics* 30: 923-930 (2014).

Robinson, M. D., McCarthy, D. J. & Smyth, G. K. edgeR: a Bioconductor package for differential expression analysis of digital gene expression data. *Bioiriformatics* 26: 139-140 (2010).

Benjamini, Y. & Hochberg, Y. Controlling the false discovery rate: a practical and powerful approach to multiple testing. *Journal of the Royal Statistical Society* Series B 57: 289-300 (1995).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:
1. A composition comprising at least four of the following active agents: a BMP type I receptor ALK2/3 inhibitor, a TGF-beta inhibitor, a WNT inhibitor, a neuronal differentiation enhancer, a SMO agonist, a retinoic acid receptor γ agonist, a DNA methyltransferase inhibitor, a histone demethylase inhibitor, an autophagy regulator, or any combination thereof.
2. The composition of statement 1, containing at least five of the active agents, or at least six of the active agents, or at least seven of the active agents, or at least eight of the active agents.
3. The composition of statement 1 or 2, with active agents consisting of BMP type I receptor ALK2/3 inhibitor, a TGF-beta inhibitor, a WNT inhibitor, a neuronal differentiation enhancer, a SMO agonist, a retinoic acid receptor γ agonist, a DNA methyltransferase inhibitor, a histone demethylase inhibitor, and an autophagy regulator.
4. The composition of any of statements 1-3, comprising or consisting of active agents: a BMP type I receptor ALK2/3 inhibitor (LDN-193189), an inhibitor of TGF-type I receptor ALK4/5/7 (A8301), a neuronal differentiation enhancer (bFGF) and a SMO agonist (Hg—Ag 1.5).
5. The composition of any of statements 1-4, without the autophagy regulator.
6. The composition of any of statements 1-5, without the histone demethylase inhibitor.
7. The composition of any of statements 1-6, without the retinoic acid receptor γ agonist.
8. The composition of any of statements 1-7, wherein the BMP type I receptor ALK2/3 inhibitor is:
   4-(6-(4-(piperazin-1-yl)phenyl)pyrazolo[1,5-a]pyrimidin-3-yl)quinoline (LDN-193189);
   6-[4-[2-(1-piperidinyl)ethoxy]phenyl]-3-(4-pyridinyl)-pyrazolo[1,5-a]pyrimidine dihydrochloride (Dorsomorphin dihydrochloride);
   3-(6-amino-5-(3,4,5-trimethoxyphenyl)pyridin-3-yl) phenol (K02288), available from Tocris Bioscience or a combination thereof.
9. The composition of any of statements 1-8, wherein the ALK2/3 inhibitor is 4-(6-(4-(piperazin-1-yl)phenyl) pyrazolo[1,5-a]pyrimidin-3-yl)quinoline (LDN-193189).
10. The composition of any of statements 1-9, wherein TGF-beta inhibitor is.
    3-(6-Methyl-2-pyridinyl)-N-phenyl-4-(4-quinolinyl)-1H-1-pyrazole-1-carbothioamide (A83-01);
    4-[4-(1,3-benzodioxol-5-yl)-5-(2-pyridinyl)-1H-imidazol-2-yl]benzamide (SB 431542);
    2-(3-(6-Methylpyridine-2-yl)-1H-pyrazol-4-yl)-1,5-naphthyridine (SJN 2511);
    4-[4-(2,3-Dihydro-1,4-benzodioxin-6-yl)-5-(2-pyridinyl)-1H-imidazol-2-yl]benzamide (D 4476);
    4-[3-(2-Pyridinyl)-1H-1-pyrazol-4-yl]-quinoline (LY 364947);
    2-(4-(benzo[d][1,3]dioxol-5-yl)-2-tert-butyl-1H-imidazol-5-yl)-6-methylpyridine (SB505124);
    6-[2-(1,1-Dimethylethyl)-5-(6-methyl-2-pyridinyl)-1H-imidazol-4-yl]quinoxaline (SB 525334);
    2-(5-Chloro-2-fluorophenyl)-4-[(4-pyridyl)amino]pteridine (SD 208); or
    any combination thereof.
11. The composition of any of statements 1-10, wherein TGF-beta inhibitor is 3-(6-Methyl-2-pyridinyl)-N-phenyl-4-(4-quinolinyl)-1H-pyrazole-1-carbothioamide (A83-01).
12. The composition of any of statements 1-11, wherein the WNT inhibitor is:
    CHIR99021 (6-(2-(4-(2,4-dichlorophenyl)-5-(4-methyl-1H-imidazol-2-yl)pyrimidin-2-ylamino)ethylamino)nicotinonitrile);
    1-azakenpaullone (9-Bromo-7,12-dihydro-pyrido[3',2':2,3]azepino[4,5-b]indol-6(5H)-one), BIO ((2'Z,3'E)-6-Bromoindirubin-3'-oxime);
    AR-A014418 (N-(4-Methoxybenzyl)-N'-(5-nitro-1,3-thiazol-2-yl)urea);
    Indirubin-3'-monoxime;
    5-Iodo-indirubin-3'-monoxime;
    kenpaullone (9-Bromo-7,12-dihydroindolo-[3,2-d][1]benzazepin-6(5H)-one),
    SB-415286 (3-[(3-Chloro-4-hydroxyphenyl)amino]-4-(2-nitro-phenyl)-1H-pyrrole-2,5-dione);
    SB-216763 (3-(2,4-Dichlorophenyl)-4-(1-methyl-1H-indol-3-yl)-1H-pyrrole-2,5-dione);
    Maybridge SEW00923SC phenyl-1,3,4-oxadiazole);
    (Z)-5-(2,3-Memylenedioxyphenyl)imidazolidine-2,4-dione,
    TWS119 (3-(6-(3-aminophenyl)-7H-pyrrolo[2,3-d]pyrimidin-4-yloxy)phenol);
    CHIR98014 (N2-(2-(4-(2,4-dichlorophenyl)-5-(1H-imidazol-1-yl)pyrimidin-2-ylamino)ethyl)-5-nitropyridine-2,6-diamine);
    SB415286 (3-(3-chloro-4-hydroxyphenylamino)-4-(2-nitrophenyl)-1H-pyrrole-2,5-dione);
    Tideglusib (also known as NP031112, or NP-12; 1,2,4-Thiadiazolidine-3,5-dione, 2-(1-naphthalenyl)-4-(phenylmethyl)),
    LY2090314 (1H-Pyrrole-2,5-dione, 3-imidazo[1,2-a]pyridin-3-yl-4-[1,2,3,4-tetrahydro-2-(1-piperidinylcarbonyl)pyrrolo[3,2,1-jk][1,4]benzodiazepin-7-yl]);
    lithium salt (e.g., LiCl), or
    any combination thereof.
13. The composition of any of statements 1-12, wherein the WNT inhibitor is CHIR99021.
14. The composition of any of statements 1-13, wherein the neuronal differentiation enhancer is:
    basic fibroblast growth factor (bFGF, also called FGF2);
    KHS2;
    fibroblast growth factor-8;
    brain-derived neurotrophic factor (BDNF);
    Sonic Hedgehog (SHH);
    supplement containing recombinant human insulin, human transferrin (iron-saturated), sodium selenite, putrescine and progesterone in Phosphate Buffered Saline); or
    any combination thereof.
15. The composition of any of statements 1-14, wherein the neuronal differentiation enhancer is basic fibroblast growth factor (bFGF);
16. The composition of any of statements 1-15, wherein the SMO agonist is:
    3-chloro-4,7-difluoro-N-(4-(methylamino)cyclohexyl)-N-(3-(pyridin-4-yl)benzyl)benzo[b]thiophene-2-carboxamide (also called Hh-Ag1.5);
    (3β)-Cholest-5-ene-3,20-diol;

3-Chloro-N-[trans-4-(methylamino)cyclohexyl]-N-[[3-(4-pyridinyl)phenyl]methyl]benzo[h]thiophene-2-carboxamide (SAG); or
any combination thereof.
17. The composition of any of statements 1-16, wherein the SMO agonist is Hh-Ag1.5.
18. The composition of any of statements 1-17, wherein the retinoic acid receptor γ agonist is:
retinoic acid;
4-(6-hydroxy-7-tricyclo[3.3.1.13,7]dec-1-yl-2-naphthalenyl)benzoic acid (CD1530);
4-[(E)-3-hydroxy-3-(5,5,8,8-tetramethyl-6,7-dihydronaphthalen-2-yl)prop-1-enyl]benzoic Acid (CD666);
4-((1E,3E)-3-(hydroxyimino)-3-(5,5,8,8-tetramethyl-5,6,7,8-tetrahydronaphthalen-2-yl)prop-1-en-1-yl) benzoic acid (NRX204647);
all-trans retinoic acid (ATRA);
9-cis retinoic acid;
all-trans 3-4 didehydro retinoic acid
4-oxo retinoic acid;
retinol;
4-[(E)-2-(5,6,7,8-tetrahydro-5,5,8,8-tetramethyl-2-naphthalenyl)-1-propenyl]benzoic acid;
4-(5-methoxymethyl-5-methyl-2,3,4,5-tetrahydro-1-benzo[b]oxepin-8-yl-ethynyl)-benzoic acid;
4-(5-ethoxymethyl-5-methyl-2,3,4,5-tetrahydrobenzo[b]oxepin-8-ylethynyl)-benzoic acid;
4-(5-methyl-5-propoxymethyl-2,3,4,5-tetrahydrobenzo[b]oxepin-8-ylethynyl)-benzoic acid;
(E)-4-[2-(5-methoxymethyl-5-propyl-2,3,4,5-tetrahydrobenzo[b]oxepin-8-yl)-vinyl]-benzoic acid;
(E)-4-[2-(5-methoxymethyl-5-methyl-2,3,4,5-tetrahydrobenzo[b]oxepin-8-yl)-vinyl]-benzoic acid;
(E)-4-[2-(5-methyl-5-propoxymethyl-2,3,4,5-tetrahydrobenzo[b]oxepin-8-yl)-vinyl]-benzoic acid;
4-(5-methoxymethyl-5-methyl-2,3,4,5-tetrahydrobenzo[b]thiepin-8-ylethynyl)-benzoic acid;
4-(5-ethoxymethyl-5-methyl-2,3,4,5-tetrahydrobenzo[b]thiepin-8-ylethynyl)-benzoic acid;
(E)-4-[2-(5-ethoxymethyl-5-methyl-2,3,4,5-tetrahydrobenzo[b]thiepin-8-yl)-vinyl]-benzoic acid;
(E)-4-[2-(5-methoxymethyl-5-propyl-2,3,4,5-tetrahydrobenzo[b]thiepin-8-yl)-vinyl]-benzoic acid;
4-(4-methoxymethyl-4-methyl-chroman-6-ylethynyl)-benzoic acid;
(E)-4-[2-(4-methoxymethyl-4-methyl-chroman-6-yl)-vinyl]-benzoic acid; or
any combination thereof
19. The composition of any of statements 1-18, wherein the retinoic acid receptor γ agonist is retinoic acid.
20. The composition of any of statements 1-19, wherein the DNA methyltransferase inhibitor is:
RG108 (N-Phthalyl-L-tryptophan);
5-azacitidine (also called azacitidine),
an antibody that binds to DNA methyltransferase;
a siRNA and antisense nucleic acids that suppress expression of DNMT
a siRNA that suppress expression or translation of DNMT;
an antisense nucleic acid that suppress expression or translation of DNMT;
5-aza-2'-deoxycytidine;
decitabine;
doxorubicin;
(−)-epigallocatechin-3-gallate (EGCG),
zebularine; or
any combination thereof.

21. The composition of any of statements 1-20, wherein the histone demethylase inhibitor is RG108.
22. The composition of any of statements 1-21, wherein the autophagy regulator is SMER28, apigenin, berberine, beta-elemene, capsaicin, curcumin, genistein, kaempferol, oridonin, paclitaxel, quercetin, resveratrol, silybin, triptolide, ursolic acid, or any combination thereof.
23. The composition of any of statements 1-22, wherein the autophagy regulator is SMER28
24. The composition of any of statements 1-23, further comprising a physiologically acceptable excipient or carrier.
25. The composition of any of statements 1-24, wherein the composition is a cell reprogramming composition
26. The composition of any of statements 1-25, wherein each of the agents is present in an amount sufficient to reprogram a starting cell into a neuronal cell type.
27. The composition of any of statements 1-26, wherein each of the agents is present in an amount sufficient to induce a cell to express is Pax6, Sox2, Ascl1, Olig2, Nestin, Tuj1, Tau, NeuN, MAP2, synapsin, Syt1, Sty4, Sytl3, Sytl6, NeuroD, Is11, cholineacetyltransferase (ChAT, e.g., vascular ChAT (VChAT)), or any combination thereof
28. The composition of statement 26 or 27, wherein the cell is a non-neuronal cell.
29. The composition of any of statements 26-28, wherein the cell is a differentiated cell.
30. The composition of any of statements 26-29, wherein the cell is a somatic cell.
31. The composition of any of statements 26-30, wherein the cell is an adult cell.
32. The composition of any of statements 26-31, wherein the cell is a multipotent, unipotent, or progenitor cell.
33. The composition of any of statements 26-32, wherein the cell is a newborn cord blood cell, or a newborn stem cell.
34. The composition of any of statements 26-33, wherein the cell is an allogenic or autologous cell
35. The composition of any of statements 26-34, wherein the cell is a heterogeneous or homogeneous mixture of cells.
36. A method of generating a reprogrammed progenitor neuronal cell or a reprogrammed neuronal cell comprising contacting a selected cell with the composition of any of statements 1-35, to thereby generate a reprogrammed neuronal progenitor cell or a reprogrammed neuronal cell.
37. The method of statement 36, wherein the selected cell is a population of cells contacted with the composition.
38. The method of statement 36 or 37, wherein the selected cell (or population of cells) is incubated with the composition.
39. The method of any of statements 36-38, wherein the selected cell (or population of cells) is incubated with the composition for at least 4 days.
40. The method of any of statements 36-39, wherein the selected cell (or population of cells) is incubated with the composition for at least 5 days, for at least 6 days, for at least 7 days, for at least 8 days, for at least 9 days, or for at least 10 days.
41. The method of any of statements 36-40, wherein the selected cell (or population of cells) is incubated with the composition for about 4 days to about 30 days.

42. The method of any of statements 36-41, wherein the selected cell is a differentiated cell.
43. The method of any of statements 36-42, wherein the selected cell is a non-neuronal cell.
44. The method of any of statements 36-43, wherein the selected cell is a somatic cell.
45. The method of any of statements 36-44, wherein the selected cell is a heterogeneous or homogeneous mixture of cells.
46. The method of any of statements 36-45, wherein the selected cell is an adult cell.
47. The method of any of statements 36-46, wherein the selected cell is a multipotent, unipotent, or progenitor cell.
48. The method of any of statements 36-47, wherein the selected cell is a newborn cord blood cell, or a newborn stem cell.
49. The method of any of statements 36-48, wherein the selected cell is an allogenic or autologous cell
50. The method of any of statements 36-49, wherein the selected cell is an in vivo cell.
51. The method of any of statements 36-49, wherein the selected cell is maintained in vitro.
52. The method of any of statements 36-51, wherein the selected cell is contacted with the composition for a time and/or with an amount of each agent sufficient to induce the selected cell to express is Pax6, Sox2, Ascl1, Olig2, Nestin, Tuj1, Tau, NeuN, MAP2, synapsin, Syt1, Syt4, Sytl3, Sytl6, NeuroD, Is11, cholineacetyltransferase (ChAT, e.g., vascular ChAT (VChAT)), or any combination thereof
53. The method of any of statements 36-52, further comprising expressing Elk1 and/or Gli2 in the selected cell.
54. The method of statement 53, where the Elk1 and/or Gli2 is expressed from a transgene or an expression cassette comprising a promoter operably linked to a nucleic acid segment encoding the Elk1 and/or Gli2 protein,
55. The method of any of statements 36-54, furthering comprising administering the neuronal cell to a subject.
56. The method of any of statements 36-55, furthering comprising administering at least about 100 of the reprogrammed neuronal cells to a subject.
57. The method of any of statements 36-56, comprising administering at least about 1000, or at least about 10,000, or at least about 100,000, or at least about 1,000,000, or at least about 10,000,000, or at least about 100,000,000 of the neuronal cells to a subject.
58 The method of any of statements 36-57, wherein the neuronal cell(s) is/are allogenic or autologous cell(s).
59. The method of any of statements 36-58, wherein the neuronal cell(s) is/are neuronal progenitor cells.
60. The method of any of statements 36-59, wherein the neuronal cell(s) is/are mature neuronal cells.
61. The method of any of statements 36-60, wherein the subject suffers or is suspected of suffering from Amyotrophic lateral sclerosis (ALS), Alzheimer's disease, Parkinson's disease, multiple sclerosis, Primary lateral sclerosis (PLS), Progressive bulbar palsy, Pseudobulbar palsy, Primary lateral sclerosis (PLS), Progressive muscular atrophy, Spinal muscular atrophy (SMA), including Type I (also called Werdnig-Hoffmann disease), Type II, Type III (Kugelberg-Welander disease), Fazio-Londe disease, Huntington's disease. Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, stroke, head trauma, spinal cord injury, or a combination thereof
62. A method comprising administering the composition of any of statements 1-35, to a subject.
63. The method of statement 62, wherein the composition contains one or more neuronal progenitor cells and/or one or more mature neuronal cells.
64. The method of statement 62 or 63, wherein the composition contains one or more allogenic or autologous cell.
65. The method of any of statements 62-64, wherein the composition contains one or more, or at least about 1000, cells that express Pax6, Sox2, Ascl1, Olig2, Nestin, Tuj1, Tau, NeuN, MAP2, synapsin, Syt1, Syt4, Sytl3, Sytl6, NeuroD, Is11, cholineacetyltransferase (ChAT, e.g., vascular ChAT (VChAT)), or a combination thereof
66. The method of any of statements 62-65, wherein the composition contains at least about 1000, or at least about 10,000, or at least about 100,000, or at least about 1,000,000, or at least about 10,000,000, or at least about 100,000,000 neuronal cells,
67, The method of any of statements 62-66, wherein the subject is in need of administration of the composition.
68. The method of any of statements 62-67, wherein the subject is in need of neuronal progenitor cells or mature neuronal cells.
69. The method of any of statements 62-68, wherein the composition is administered for a time and/or with an amount of each agent sufficient to reduce the symptoms of a neuronal condition or disease.
70. The method of any of statements 62-69, wherein the subject suffers or is suspected of suffering from Amyotrophic lateral sclerosis (ALS), Alzheimer's disease, Parkinson's disease, multiple sclerosis, Primary lateral sclerosis (PLS), Progressive bulbar palsy, Pseudobulbar palsy, Progressive muscular atrophy, Spinal muscular atrophy (SMA), including Type I (also called Werdnig-Hoffmann disease), Type II, Type III (Kugelberg-Welander disease), Fazio-Londe disease, Huntington's disease, Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, stroke, head trauma, spinal cord injury, or a combination thereof.
71. A kit comprising the composition of any of statements 1-35, and instructions for using the composition.
72. The kit of statement 71, further comprising components for in vitro cell culture of a selected cell,
73. The kit of statement 71 or 72, further comprising one or more cell collection devices (e.g., one or more sterile cell collection devices).
74. The kit of any of statements 71-73, further comprising cell culture medium, or a supplementary factor.
75. The kit of any of statement 71-74, further comprising a population of neuronal cells generated by contacting the cells with the composition
76. The kit of any of statements 71-75, further comprising a diluent, a pharmaceutically acceptable carrier, a syringe, a catheter, or a device for delivery of cells or of the composition.

77. The kit of any of statements 71-76, further comprising antibodies, probes, or primers for detection of a neuronal progenitor cell marker or a neuronal cell marker.
78. The kit of statement 77, wherein the marker is Pax6, Sox2, Ascl1, Olig2, Nestin, Tuj1, Tau, NeuN, MAP2, synapsin, Sytl, Syt4, Sytl3, Sytl6, NeuroD, Is11, cholineacetyltransferase (ChAT, e.g., vascular ChAT (VChAT)), or any combination thereof.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed:

1. A method of generating a neuronal cell or a neuronal progenitor cell, comprising contacting a selected differentiated, non-neuronal cell with a composition comprising active agents CHIR99021; LDN193189; A83-01; Hh-Ag1.5; retinoic acid; SMER28; RG108, parnate, and bFGF, in an amount sufficient to reprogram the selected cell to thereby generate a neuronal progenitor cell.

2. The method of claim 1, wherein the selected cell contacted with the composition is a somatic cell, a population of cells, a heterogeneous mixture of cells, a population of non-neuronal cells, or a combination thereof.

3. The method of claim 1, wherein the selected cell is a newborn cord blood cell.

4. The method of claim 1, wherein the selected cell is an allogenic or autologous cell.

5. The method of claim 1, wherein the agents are present in an amount sufficient to induce the selected cell to express Pax6, Sox2, Ascl1, Olig2, Nestin, Tuj1, Tau, NeuN, MAP2, synapsin, Syt1, Syt4, Sytl3, Syt16, NeuroD, Is11, cholineacetyltransferase, or any combination thereof.

6. The method of claim 1, further comprising administering the neuronal cell, the neuronal progenitor cell, or a combination thereof to a subject.

7. The method of claim 6, wherein the subject suffers or is suspected of suffering from Amyotrophic lateral sclerosis (ALS), Alzheimer's disease, Parkinson's disease, multiple sclerosis, Primary lateral sclerosis (PLS), Progressive bulbar palsy, Pseudobulbar palsy, Primary lateral sclerosis (PLS), Progressive muscular atrophy, Spinal muscular atrophy (SMA), including Type I (also called Werdnig-Hoffmann disease), Type II, Type III (Kugelberg-Welander disease), Fazio-Londe disease, Huntington's disease, Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, stroke, head trauma, spinal cord injury, or a combination thereof.

* * * * *

SEQUENCE LISTING

```
<160> NUMBER OF SEQ ID NOS: 32

<210> SEQ ID NO 1
<211> LENGTH: 1586
<212> TYPE: PRT
<213> ORGANISM: Homo sapiens

<400> SEQUENCE: 1

Met Glu Thr Ser Ala Ser Ala Thr Ala Ser Glu Lys Gln Glu Ala Lys
1               5                   10                  15

Ser Gly Ile Leu Glu Ala Ala Gly Phe Pro Asp Pro Gly Lys Lys Ala
            20                  25                  30

Ser Pro Leu Val Val Ala Ala Ala Ala Ala Ala Val Ala Ala Gln
        35                  40                  45

Gly Val Pro Gln His Leu Leu Pro Pro Phe His Ala Pro Leu Pro Ile
    50                  55                  60

Asp Met Arg His Gln Glu Gly Arg Tyr His Tyr Glu Pro His Ser Val
65                  70                  75                  80

His Gly Val His Gly Pro Pro Ala Leu Ser Gly Ser Pro Val Ile Ser
                85                  90                  95

Asp Ile Ser Leu Ile Arg Leu Ser Pro His Pro Ala Gly Pro Gly Glu
            100                 105                 110

Ser Pro Phe Asn Ala Pro His Pro Tyr Val Asn Pro His Met Glu His
        115                 120                 125

Tyr Leu Arg Ser Val His Ser Ser Pro Thr Leu Ser Met Ile Ser Ala
    130                 135                 140

Ala Arg Gly Leu Ser Pro Ala Asp Val Ala Gln Glu His Leu Lys Glu
145                 150                 155                 160

Arg Gly Leu Phe Gly Leu Pro Ala Pro Gly Thr Thr Pro Ser Asp Tyr
                165                 170                 175

Tyr His Gln Met Thr Leu Val Ala Gly His Pro Ala Pro Tyr Gly Asp
            180                 185                 190

Leu Leu Met Gln Ser Gly Gly Ala Ala Ser Ala Pro His Leu His Asp
        195                 200                 205
```

```
Tyr Leu Asn Pro Val Asp Val Ser Arg Phe Ser Ser Pro Arg Val Thr
    210                 215                 220
Pro Arg Leu Ser Arg Lys Arg Ala Leu Ser Ile Ser Pro Leu Ser Asp
225                 230                 235                 240
Ala Ser Leu Asp Leu Gln Arg Met Ile Arg Thr Ser Pro Asn Ser Leu
                245                 250                 255
Val Ala Tyr Ile Asn Asn Ser Arg Ser Ser Ala Ala Ser Gly Ser
            260                 265                 270
Tyr Gly His Leu Ser Ala Gly Ala Leu Ser Pro Ala Phe Thr Phe Pro
        275                 280                 285
His Pro Ile Asn Pro Val Ala Tyr Gln Gln Ile Leu Ser Gln Gln Arg
290                 295                 300
Gly Leu Gly Ser Ala Phe Gly His Thr Pro Pro Leu Ile Gln Pro Ser
305                 310                 315                 320
Pro Thr Phe Leu Ala Gln Gln Pro Met Ala Leu Thr Ser Ile Asn Ala
                325                 330                 335
Thr Pro Thr Gln Leu Ser Ser Ser Asn Cys Leu Ser Asp Thr Asn
                340                 345                 350
Gln Asn Lys Gln Ser Ser Glu Ser Ala Val Ser Ser Thr Val Asn Pro
            355                 360                 365
Val Ala Ile His Lys Arg Ser Lys Val Lys Thr Glu Pro Glu Gly Leu
        370                 375                 380
Arg Pro Ala Ser Pro Leu Ala Leu Thr Gln Gly Gln Val Ser Gly His
385                 390                 395                 400
Gly Ser Cys Gly Cys Ala Leu Pro Leu Ser Gln Glu Gln Leu Ala Asp
                405                 410                 415
Leu Lys Glu Asp Leu Asp Arg Asp Asp Cys Lys Gln Glu Ala Glu Val
                420                 425                 430
Val Ile Tyr Glu Thr Asn Cys His Trp Glu Asp Cys Thr Lys Glu Tyr
        435                 440                 445
Asp Thr Gln Glu Gln Leu Val His Ile Asn Asn Glu His Ile His
450                 455                 460
Gly Glu Lys Lys Glu Phe Val Cys Arg Trp Gln Ala Cys Thr Arg Glu
465                 470                 475                 480
Gln Lys Pro Phe Lys Ala Gln Tyr Met Leu Val Val His Met Arg Arg
                485                 490                 495
His Thr Gly Glu Lys Pro His Lys Cys Thr Phe Glu Gly Cys Ser Lys
            500                 505                 510
Ala Tyr Ser Arg Leu Glu Asn Leu Lys Thr His Leu Arg Ser His Thr
        515                 520                 525
Gly Glu Lys Pro Tyr Val Cys Glu His Glu Gly Cys Asn Lys Ala Phe
530                 535                 540
Ser Asn Ala Ser Asp Arg Ala Lys His Gln Asn Arg Thr His Ser Asn
545                 550                 555                 560
Glu Lys Pro Tyr Ile Cys Lys Ile Pro Gly Cys Thr Lys Arg Tyr Thr
                565                 570                 575
Asp Pro Ser Ser Leu Arg Lys His Val Lys Thr Val His Gly Pro Asp
            580                 585                 590
Ala His Val Thr Lys Lys Gln Arg Asn Asp Val His Leu Arg Thr Pro
        595                 600                 605
Leu Leu Lys Glu Asn Gly Asp Ser Glu Ala Gly Thr Glu Pro Gly Gly
610                 615                 620
```

-continued

```
Pro Glu Ser Thr Glu Ala Ser Ser Thr Ser Gln Ala Val Glu Asp Cys
625                 630                 635                 640

Leu His Val Arg Ala Ile Lys Thr Glu Ser Ser Gly Leu Cys Gln Ser
            645                 650                 655

Ser Pro Gly Ala Gln Ser Ser Cys Ser Ser Glu Pro Ser Pro Leu Gly
        660                 665                 670

Ser Ala Pro Asn Asn Asp Ser Gly Val Glu Met Pro Gly Thr Gly Pro
        675                 680                 685

Gly Ser Leu Gly Asp Leu Thr Ala Leu Asp Thr Pro Pro Gly Ala
690                 695                 700

Asp Thr Ser Ala Leu Ala Ala Pro Ser Ala Gly Gly Leu Gln Leu Arg
705                 710                 715                 720

Lys His Met Thr Thr Met His Arg Phe Glu Gln Leu Lys Lys Glu Lys
                725                 730                 735

Leu Lys Ser Leu Lys Asp Ser Cys Ser Trp Ala Gly Pro Thr Pro His
            740                 745                 750

Thr Arg Asn Thr Lys Leu Pro Pro Leu Pro Gly Ser Gly Ser Ile Leu
        755                 760                 765

Glu Asn Phe Ser Gly Ser Gly Gly Gly Pro Ala Gly Leu Leu Pro
770                 775                 780

Asn Pro Arg Leu Ser Glu Leu Ser Ala Ser Glu Val Thr Met Leu Ser
785                 790                 795                 800

Gln Leu Gln Glu Arg Arg Asp Ser Ser Thr Ser Val Ser Ser Ala
                805                 810                 815

Tyr Thr Val Ser Arg Arg Ser Ser Gly Ile Ser Pro Tyr Phe Ser Ser
            820                 825                 830

Arg Arg Ser Ser Glu Ala Ser Pro Leu Gly Ala Gly Arg Pro His Asn
835                 840                 845

Ala Ser Ser Ala Asp Ser Tyr Asp Pro Ile Ser Thr Asp Ala Ser Arg
        850                 855                 860

Arg Ser Ser Glu Ala Ser Gln Cys Ser Gly Gly Ser Gly Leu Leu Asn
865                 870                 875                 880

Leu Thr Pro Ala Gln Gln Tyr Ser Leu Arg Ala Lys Tyr Ala Ala Ala
                885                 890                 895

Thr Gly Gly Pro Pro Pro Thr Pro Leu Pro Gly Leu Glu Arg Met Ser
            900                 905                 910

Leu Arg Thr Arg Leu Ala Leu Leu Asp Ala Pro Glu Arg Thr Leu Pro
        915                 920                 925

Ala Gly Cys Pro Arg Pro Leu Gly Pro Arg Arg Gly Ser Asp Gly Pro
930                 935                 940

Thr Tyr Gly His Gly His Ala Gly Ala Ala Pro Ala Phe Pro His Glu
945                 950                 955                 960

Ala Pro Gly Gly Gly Ala Arg Arg Ala Ser Asp Pro Val Arg Arg Pro
                965                 970                 975

Asp Ala Leu Ser Leu Pro Arg Val Gln Arg Phe His Ser Thr His Asn
            980                 985                 990

Val Asn Pro Gly Pro Leu Pro Pro Cys Ala Asp Arg Arg Gly Leu Arg
        995                 1000                1005

Leu Gln Ser His Pro Ser Thr Asp Gly Gly Leu Ala Arg Gly Ala Tyr
            1010                1015                1020

Ser Pro Arg Pro Pro Ser Ile Ser Glu Asn Val Ala Met Glu Ala Val
1025                1030                1035                1040

Ala Ala Gly Val Asp Gly Ala Gly Pro Glu Ala Asp Leu Gly Leu Pro
```

-continued

```
            1045                1050                1055
Glu Asp Asp Leu Val Leu Pro Asp Val Val Gln Tyr Ile Lys Ala
                1060                1065                1070
His Ala Ser Gly Ala Leu Asp Glu Gly Thr Gly Gln Val Tyr Pro Thr
            1075                1080                1085
Glu Ser Thr Gly Phe Ser Asp Asn Pro Arg Leu Pro Ser Pro Gly Leu
            1090                1095                1100
His Gly Gln Arg Arg Met Val Ala Ala Asp Ser Asn Val Gly Pro Ser
1105                1110                1115                1120
Ala Pro Met Leu Gly Gly Cys Gln Leu Gly Phe Gly Ala Pro Ser Ser
                1125                1130                1135
Leu Asn Lys Asn Asn Met Pro Val Gln Trp Asn Glu Val Ser Ser Gly
                1140                1145                1150
Thr Val Asp Ala Leu Ala Ser Gln Val Lys Pro Pro Pro Phe Pro Gln
            1155                1160                1165
Gly Asn Leu Ala Val Val Gln Gln Lys Pro Ala Phe Gly Gln Tyr Pro
            1170                1175                1180
Gly Tyr Ser Pro Gln Gly Leu Gln Ala Ser Pro Gly Gly Leu Asp Ser
1185                1190                1195                1200
Thr Gln Pro His Leu Gln Pro Arg Ser Gly Ala Pro Ser Gln Gly Ile
            1205                1210                1215
Pro Arg Val Asn Tyr Met Gln Gln Leu Arg Gln Pro Val Ala Gly Ser
            1220                1225                1230
Gln Cys Pro Gly Met Thr Thr Thr Met Ser Pro His Ala Cys Tyr Gly
            1235                1240                1245
Gln Val His Pro Gln Leu Ser Pro Ser Thr Ile Ser Gly Ala Leu Asn
            1250                1255                1260
Gln Phe Pro Gln Ser Cys Ser Asn Met Pro Ala Lys Pro Gly His Leu
1265                1270                1275                1280
Gly His Pro Gln Gln Thr Glu Val Ala Pro Asp Pro Thr Thr Met Gly
            1285                1290                1295
Asn Arg His Arg Glu Leu Gly Val Pro Asp Ser Ala Leu Ala Gly Val
            1300                1305                1310
Pro Pro Pro His Pro Val Gln Ser Tyr Pro Gln Gln Ser His His Leu
            1315                1320                1325
Ala Ala Ser Met Ser Gln Glu Gly Tyr His Gln Val Pro Ser Leu Leu
            1330                1335                1340
Pro Ala Arg Gln Pro Gly Phe Met Glu Pro Gln Thr Gly Pro Met Gly
1345                1350                1355                1360
Val Ala Thr Ala Gly Phe Gly Leu Val Gln Pro Arg Pro Pro Leu Glu
                1365                1370                1375
Pro Ser Pro Thr Gly Arg His Arg Gly Val Arg Ala Val Gln Gln Gln
                1380                1385                1390
Leu Ala Tyr Ala Arg Ala Thr Gly His Ala Met Ala Ala Met Pro Ser
            1395                1400                1405
Ser Gln Glu Thr Ala Glu Ala Val Pro Lys Gly Ala Met Gly Asn Met
    1410                1415                1420
Gly Ser Val Pro Pro Gln Pro Pro Gln Asp Ala Gly Gly Ala Pro
1425                1430                1435                1440
Asp His Ser Met Leu Tyr Tyr Tyr Gly Gln Ile His Met Tyr Glu Gln
                1445                1450                1455
Asp Gly Gly Leu Glu Asn Leu Gly Ser Cys Gln Val Met Arg Ser Gln
                1460                1465                1470
```

```
Pro Pro Gln Pro Gln Ala Cys Gln Asp Ser Ile Gln Pro Gln Pro Leu
         1475                1480                1485

Pro Ser Pro Gly Val Asn Gln Val Ser Thr Val Asp Ser Gln Leu
1490                1495                1500

Leu Glu Ala Pro Gln Ile Asp Phe Asp Ala Ile Met Asp Asp Gly Asp
1505                1510                1515                1520

His Ser Ser Leu Phe Ser Gly Ala Leu Ser Pro Ser Leu Leu His Ser
                1525                1530                1535

Leu Ser Gln Asn Ser Ser Arg Leu Thr Thr Pro Arg Asn Ser Leu Thr
            1540                1545                1550

Leu Pro Ser Ile Pro Ala Gly Ile Ser Asn Met Ala Val Gly Asp Met
        1555                1560                1565

Ser Ser Met Leu Thr Ser Leu Ala Glu Glu Ser Lys Phe Leu Asn Met
    1570                1575                1580

Met Thr
1585

<210> SEQ ID NO 2
<211> LENGTH: 428
<212> TYPE: PRT
<213> ORGANISM: Homo sapiens

<400> SEQUENCE: 2

Met Asp Pro Ser Val Thr Leu Trp Gln Phe Leu Leu Gln Leu Leu Arg
1               5                   10                  15

Glu Gln Gly Asn Gly His Ile Ile Ser Trp Thr Ser Arg Asp Gly Gly
            20                  25                  30

Glu Phe Lys Leu Val Asp Ala Glu Val Ala Arg Leu Trp Gly Leu
        35                  40                  45

Arg Lys Asn Lys Thr Asn Met Asn Tyr Asp Lys Leu Ser Arg Ala Leu
    50                  55                  60

Arg Tyr Tyr Tyr Asp Lys Asn Ile Ile Arg Lys Val Ser Gly Gln Lys
65                  70                  75                  80

Phe Val Tyr Lys Phe Val Ser Tyr Pro Glu Val Ala Gly Cys Ser Thr
                85                  90                  95

Glu Asp Cys Pro Pro Gln Pro Glu Val Ser Val Thr Ser Thr Met Pro
            100                 105                 110

Asn Val Ala Pro Ala Ala Ile His Ala Ala Pro Gly Asp Thr Val Ser
        115                 120                 125

Gly Lys Pro Gly Thr Pro Lys Gly Ala Gly Met Ala Gly Pro Gly Gly
    130                 135                 140

Leu Ala Arg Ser Ser Arg Asn Glu Tyr Met Arg Ser Gly Leu Tyr Ser
145                 150                 155                 160

Thr Phe Thr Ile Gln Ser Leu Gln Pro Gln Pro Pro His Pro Arg
                165                 170                 175

Pro Ala Val Val Leu Pro Asn Ala Pro Ala Gly Ala Ala Pro
            180                 185                 190

Pro Ser Gly Ser Arg Ser Thr Ser Pro Ser Pro Leu Glu Ala Cys Leu
        195                 200                 205

Glu Ala Glu Glu Ala Gly Leu Pro Leu Gln Val Ile Leu Thr Pro Pro
    210                 215                 220

Glu Ala Pro Asn Leu Lys Ser Glu Glu Leu Asn Val Glu Pro Gly Leu
225                 230                 235                 240

Gly Arg Ala Leu Pro Pro Glu Val Lys Val Glu Gly Pro Lys Glu Glu
```

```
                    245                 250                 255
Leu Glu Val Ala Gly Glu Arg Gly Phe Val Pro Glu Thr Thr Lys Ala
            260                 265                 270

Glu Pro Glu Val Pro Pro Gln Glu Gly Val Pro Ala Arg Leu Pro Ala
        275                 280                 285

Val Val Met Asp Thr Ala Gly Gln Ala Gly Gly His Ala Ala Ser Ser
    290                 295                 300

Pro Glu Ile Ser Gln Pro Gln Lys Gly Arg Lys Pro Arg Asp Leu Glu
305                 310                 315                 320

Leu Pro Leu Ser Pro Ser Leu Leu Gly Gly Pro Gly Pro Glu Arg Thr
                325                 330                 335

Pro Gly Ser Gly Ser Gly Ser Gly Leu Gln Ala Pro Gly Pro Ala Leu
            340                 345                 350

Thr Pro Ser Leu Leu Pro Thr His Thr Leu Thr Pro Val Leu Leu Thr
        355                 360                 365

Pro Ser Ser Leu Pro Pro Ser Ile His Phe Trp Ser Thr Leu Ser Pro
    370                 375                 380

Ile Ala Pro Arg Ser Pro Ala Lys Leu Ser Phe Gln Phe Pro Ser Ser
385                 390                 395                 400

Gly Ser Ala Gln Val His Ile Pro Ser Ile Ser Val Asp Gly Leu Ser
                405                 410                 415

Thr Pro Val Val Leu Ser Pro Gly Pro Gln Lys Pro
            420                 425

<210> SEQ ID NO 3
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 3
acatcgccaa tcagcttgg                                                    19

<210> SEQ ID NO 4
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 4
agaaccatac tcgaaccaca tcc                                               23

<210> SEQ ID NO 5
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 5
cctccagcag atgcaagaac tc                                                22

<210> SEQ ID NO 6
<211> LENGTH: 23
<212> TYPE: DNA
<213> ORGANISM: Artificial Sequence
<220> FEATURE:
<223> OTHER INFORMATION: A synthetic oligonucleotide
```

-continued

```
<400> SEQUENCE: 6
cttcaaccac tggttttttct gcc                                            23

<210> SEQ ID NO 7
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 7
catggccttc cgtgttccta                                                 20

<210> SEQ ID NO 8
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 8
gcctgcttca ccaccttctt                                                 20

<210> SEQ ID NO 9
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 9
gaacgccttc atggtatggt                                                 20

<210> SEQ ID NO 10
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 10
ttgctgatct ccgagttgtg                                                 20

<210> SEQ ID NO 11
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 11
ggccgagtgg aaggtcatgt                                                 20

<210> SEQ ID NO 12
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 12
tccgggtgtt ccttcatgtg                                                 20

<210> SEQ ID NO 13
<211> LENGTH: 19
```

```
<212> TYPE: DNA
<213> ORGANISM: Artificial Sequence
<220> FEATURE:
<223> OTHER INFORMATION: A synthetic oligonucleotide

<400> SEQUENCE: 13
cggagacgca tcacctctg                                                    19

<210> SEQ ID NO 14
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 14
agggagtgga ggagtcattc g                                                 21

<210> SEQ ID NO 15
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 15
ggcggtggct tcaagtcatc                                                   20

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 16
tagtttcgcg ccagcagcag                                                   20

<210> SEQ ID NO 17
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 17
agtcccaagg agaaaaaccg a                                                 21

<210> SEQ ID NO 18
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 18
gctgtgtttc aggtagctga c                                                 21

<210> SEQ ID NO 19
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 19
```
agggatccta cgaccctctt a								21

<210> SEQ ID NO 20
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 20
accagttggt aaagtccagc ag							22

<210> SEQ ID NO 21
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 21
cacaactccg agatcagcaa								20

<210> SEQ ID NO 22
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 22
tccgggtact ccttcatgtg								20

<210> SEQ ID NO 23
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 23
agtgtgagtt cgagggctgt								20

<210> SEQ ID NO 24
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 24
gggatgcgtg taggacttgt								20

<210> SEQ ID NO 25
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 25
tcgaggtggg tgtcaaagg								19

<210> SEQ ID NO 26
<211> LENGTH: 19
<212> TYPE: DNA
<213> ORGANISM: Artificial Sequence

```
<220> FEATURE:
<223> OTHER INFORMATION: A synthetic oligonucleotide

<400> SEQUENCE: 26
ggcgcataaa cgtcgtcca                                                  19

<210> SEQ ID NO 27
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 27 aggggagag aacaccaact                                                  20

<210> SEQ ID NO 28
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 28
catttggccc ttcgattaga                                                 20

<210> SEQ ID NO 29
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 29
agggttgtgc aaagcaagtg                                                 20

<210> SEQ ID NO 30
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 30
tggctcacac aatcagcttc                                                 20

<210> SEQ ID NO 31
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 31
atgctggttg ttcacatgcg                                                 20

<210> SEQ ID NO 32
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 32
aggcattgga gaaggctttg                                                 20
```